US011007274B2

(12) United States Patent
Jin et al.

(10) Patent No.: US 11,007,274 B2
(45) Date of Patent: May 18, 2021

(54) COMPOUNDS FOR MEDICINAL APPLICATIONS

(71) Applicant: Ausvir Therapeutics Pty LTD, Melbourne (AU)

(72) Inventors: Betty Jin, Victoria (AU); Ee-Ling Seah, Victoria (AU); Paul Arthur Jones, Victoria (AU); Peter James Jenkins, Victoria (AU); Henry Kenneth Windle, Victoria (AU); Wen Yang Wu, Victoria (AU)

(73) Assignee: Ausvir Therapeutics Pty LTD, Melbourne (AU)

( * ) Notice: Subject to any disclaimer, the term of this patent is extended or adjusted under 35 U.S.C. 154(b) by 40 days.

(21) Appl. No.: 15/984,029

(22) Filed: May 18, 2018

(65) Prior Publication Data
US 2018/0264128 A1 Sep. 20, 2018

Related U.S. Application Data

(63) Continuation of application No. PCT/AU2016/051100, filed on Nov. 16, 2016.

(30) Foreign Application Priority Data

Nov. 20, 2015 (AU) ................................ 2015904895

(51) Int. Cl.
| | |
|---|---|
| *A61K 47/54* | (2017.01) |
| *A61K 47/64* | (2017.01) |
| *A61K 47/68* | (2017.01) |
| *C07K 5/113* | (2006.01) |
| *C07K 7/06* | (2006.01) |
| *C07K 5/093* | (2006.01) |
| *C07K 5/072* | (2006.01) |
| *C07D 407/14* | (2006.01) |
| *C07D 309/28* | (2006.01) |
| *A61K 45/06* | (2006.01) |
| *A61P 31/16* | (2006.01) |
| *A61K 31/351* | (2006.01) |
| *A61K 39/42* | (2006.01) |
| *C07K 16/10* | (2006.01) |
| *A61K 39/00* | (2006.01) |

(52) U.S. Cl.
CPC .......... *A61K 47/645* (2017.08); *A61K 31/351* (2013.01); *A61K 39/42* (2013.01); *A61K 45/06* (2013.01); *A61K 47/549* (2017.08); *A61K 47/6841* (2017.08); *A61P 31/16* (2018.01); *C07D 309/28* (2013.01); *C07D 407/14* (2013.01); *C07K 5/06104* (2013.01); *C07K 5/0819* (2013.01); *C07K 5/1021* (2013.01); *C07K 7/06* (2013.01); *C07K 16/1018* (2013.01); *A61K 2039/505* (2013.01); *C07K 2317/569* (2013.01); *C07K 2317/622* (2013.01); *C07K 2319/30* (2013.01)

(58) Field of Classification Search
None
See application file for complete search history.

(56) References Cited

U.S. PATENT DOCUMENTS 7,205,333 B2 * 4/2007 Wu ......................... A61P 43/00
514/451

FOREIGN PATENT DOCUMENTS

| | | | |
|---|---|---|---|
| CN | 1343205 | A | 4/2002 |
| CN | 104640540 | A | 5/2015 |
| CN | 105085455 | A | 11/2015 |
| JP | 2002-539204 | | 11/2002 |
| JP | 2004-507564 | | 3/2004 |
| JP | 2005-199718 | | 7/2005 |
| JP | 2013-199446 | | 10/2013 |
| WO | WO 90/05144 | A1 | 5/1990 |
| WO | WO 98/21243 | A1 | 5/1998 |
| WO | WO 2000/055149 | A1 | 9/2000 |
| WO | WO 2002/020514 | A1 | 3/2002 |
| WO | WO 2003/040138 | A1 | 5/2003 |
| WO | WO 2013/155375 | A1 | 10/2013 |
| WO | WO 2015/011441 | A1 | 1/2015 |

OTHER PUBLICATIONS

Abdel-Magid A. F., et al.: Synthesis of Influenza Neuraminidase Inhibitors. *Curr. Opin. Drug Discuss. Dev.*, 4(6): 776-791 (2001).
Abed Y et al.: Generation and Characterization of recombinant influenza A (H1N1) virus harboring amantadine resistance mutation. *Antimicrob. Agents Chemother*. 49(2): 556-559 (2005).
Anderson I, et al.: Measurement of nasal mucocillary clearance. *Eur. J. Respir. Dis.*, 64(supple 127): 37-40 (1983).
Babu Y.S., et al.: Discovery of a Novel, Highly Potent, Orally Active, and Selective Influenza Neuraminidase Inhibitor through Structure-based Drug Design. *J. Med. Chem.*, 43: 3482-3486 (2000).
Baz M, et al.: Emergence of Oseltainivir-resistant pandemic H1N1 virus during prophylaxis. *N. Engl. J Med.*, 361(23): 2296-2297 (2009).
Bright R., et al.: Incidence of admantine resistance among influenza A (H3N2) viruses isolated worldwide from 1994 to 2005: a cause for concern. *Lancet*, 366(9492): 1175-1181 (2005).
Bright R., et al.: Adamantane resistance around influenza A viruses isolated early during the 2005-2006 influenza season in the United States. *JAMA*, 295(8): 891-894 (2006).
Chand P., et al.: Syntheses and Neuraminidase Inhibitory Activity of Multisubstituted Cyclopentane Amide Derivatives. *J. Med. Chem.*, 47: 1919-1929 (2004).

(Continued)

*Primary Examiner* — Traviss C McIntosh, III
(74) *Attorney, Agent, or Firm* — Foley & Lardner LLP

(57) ABSTRACT

The present invention provides compounds for use in treating and/or preventing influenza. The compound comprises a first and second domain in which the first domain comprises at least one anchoring group which binds to the surface of influenza viruses and the second domain comprises at least one anionic group. The first and second domains are covalently linked. Also provided are pharmaceutically acceptable salts, solvates, prodrugs or stereoisomer of the compounds.

19 Claims, 9 Drawing Sheets

(56) References Cited

OTHER PUBLICATIONS

Chen, W., et al.: A novel influenza A virus mitochondrial protein that induces cell death. *Nat. Med.* 7(12): 1306-1312 (2001).
Das K, et al.: Structures of influenza A proteins and insights into antiviral drug targets. *Nature Structural & Molecular Biology*, 17(5): 530-538 (2010).
De Clercq, E.: Toward improved anti-HIV chemotherapy, therapeutic strategies for intervention with HIV infections. *Med. Chem.* . . 38(14): 2491-2517 (1995).
Del Mar C., et al.: Neuraminidase inhibitors for influenza complications. *Lancet.*, 384, 1260-12614 (2014).
Demaine D.A., et al.: Dimeric compounds and their use as anti-viral agents. WO03/040138. *Chem. Abstr.*, 138:354175 (2003).
Fraser, B.H., et al.: Tanaka-M., et al.: Mechanisms of Capsaicin- and Citric-acid-induced cough reflexes in Guinea-Pig. *J. Pharmacol. Sci.*, 99, 77-82 (2005). Synthesis of 1,4-triazole linked zanamivir dimers as highly potent inhibitors of influenza A and B. *Med Chem. Commun.*, 4: 383-386 (2013).
Gao R., et al.: Human infection with a novel avian-origin influenza A (H7N9) virus. *N. Engl. J. Med.*, 368(2Q): 1888-1897 (2013).
Hale BG., et al.: Innate immune evasion strategies of influenza viruses. *Future Microbiol*, 5: 23-41 (2010).
Hagen M., et al.: Recombinant influenza virus polymerase: requirement of both 5' and 3' viral ends for endonuclease activity, *J. Virol.*, 68(3): 1509-1515 (1994).
Hayden F.: Developing new antiviral agents for influenza treatment: what does the future hold? *Clinical Infectious Diseases*, 48 (Suppl 1): S3-13 (2009).
Hayden F.: Newer influenza antivirals, biotherapeutics and combinations. *Influenza and Other Respiratory Viruses* 7(Suppl. 1): 63-75 (2012).
Herfst S., et al.: Airborne transmission of influenza A/H5N1 virus between ferrets. *Science*, 336(6088): 1534-1541 (2012).
Honda T., et al.: Synthesis and Anti-influenza Evaluation of Polyvalent Sialidase Inhibitors bearing 4-Guandino-Neu5Ac2en derivatives. *Bioorg. Med. Chem. Lett.* 12: 1929-1932 (2002).
Honda T., et al.: Synthesis and Anti-influenza Virus Activity of 7-O-Alkylated derivatives Related to Zanamivir. *Bioorg. Med. Chem. Lett.* 12: 1925-1928 (2002).
Hu Y. et al.: Association between adverse clinical outcome in human diseases caused by novel influenza A H7N9 virus and sustained viral shedding and emergences of antiviral resistance. *Lancet*, 381(9885): 2273-2279 (2013).
Imal M., et al.: Experimental adaptation of an influenza H5 HA confers respiratory droplet transmission to reassortant H5 HA/H1N1 virus in ferrets. *Nature*, 486(7403): 420-428 (2012).
International Search Report and Written Opinion for PCT/AU2016/051100 dated Feb. 10, 2017.
Jefferson T., et al.: Neuraminidase inhibitors for preventing and treating influenza in healthy adults and children. *Cochrane Database Syst. Rev.*, 4:CD008965 (2014). International Search Report and Written Opinion for PCT/AU2016/051100 dated Feb. 10, 2017.
Klumpp K.: Recent Advances in the Discovery and Development of Anti-influenza Drugs. *Expert Opin. Ther. Pat.*, 14(8): 1153-1168 (2004).
Laude E.A., et al.: A comparative study of the effect of Citric acid, Capsaicin and, Resiniferatoxin on the cough challenge in Guineapig and man. *Pulmonary Pharmacology*, 6, 171-175 (1993).
Macdonald, S.J.F., et al.: Potent and long-acting dimeric inhibitors of influenza virus neuraminidase are effective at a one-weekly dosing regimen. *Antimicrob. Agents and Chemoth.*, 48(12), 4542-4549 (2004).
Macdonald, S.J.F., et al.: Dimer zanamivir conjugates with various linking group are potent, long-lasting inhibitors of influenza neuraminidase including H5N1 Avian influenza. *J. Med. Chem.*, 48, 2964-2971 (2005).
Metersky M.L., et al.: Epidemiology, microbiology, and treatment considerations for bacterial pneumonia complicating influenza. *Int J infect Dis.*, 16: e321-331 (2012).

Nayak D.P., et al.: Assembly and budding of influenza virus. *Virus Res*, 106: 147-165 (2004).
Nelson M., et al.: The origin and global emergence of adamantine resistant A (H3N2) influenza virus. *Virology*, 388: 270-278 (2009).
Nemeroff, M.E., et al.: Influenza virus NS1 protein interacts with the cellular 30 kDa subunit of CPSF and inhibits 3'end formation of cellular pre-mRNAs. *Mol. Cell.*, 1: 991-1000 (1998).
Neumann G., et al.: Influenza A virus NS2 protein mediates vRNP nuclear export through NES-independent interaction with hCRM1. *EMBO J.*, 19(24): 6751-6758 (2000).
Newcomb, L.L., et al.: Interaction of the influenza a virus nucleocapsid protein with the viral RNA polymerase potentiates unprimed viral RNA replication. *J. Virol.*, 83(1): 29-36 (2009).
Nguyen-Van-Tam J.S., et al.: Antivirals for influenza where now for clinical practice and pandemic preparedness? *Lancet*, 384: 386-387 (2014).
Palese P., et al.: Orthomyxoviridae: the viruses and their replication, *In Fields Virology*, 5 edition. Edited by: Knipe DM, Howley PM, Philadelphia, PA:Lippincott Williams 2007:1647-1689.
Plotch, S.J., et al.: A unique cap(m7GpppXm)-dependent influenza virion endonuclease cleaves capped RNAs to generate the primers that initiate viral RNA transcription. *Cell*, 23, 847-858 (1981).
Rennie P., et al.: Low pH intranasal sprays inactivate influenza viruses in vitro and protect ferrets against influenza infection. *Respiratory Research*, 8, 38 (2007).
Roy, R. et al., "Solid-phase Synthesis of Dendritic Sialoside Inhibitors of Influenza A Virus Haemagglutinin", Journal of the Chemical Society, Chemical Communications, 1993, pp. 1869-1872, Title: scheme 1-2; Experimental; Compounds 8-17; Scheme 1, p. 1871; Fig. 1 and final paragraph, p. 1872.
Roytman, R. et al., "Exploring the self-assembly of glycopeptides using a diphenylalanine scaffold", Organic & Biomolecular Chemistry, 2011, vol. 9, pp. 5755-5761 Compound 5, Fig. 1, p. 5755; Nanostructure sample preparation and imaging, p. 5760.
Russell C.A., et al.: The potential for respiratory droplet-transmissible A/H5N1 influenza virus to evolve in a mammalian host. *Science*, 336(6088): 1541-1547 (2012).
Salomon R., et al.: The influenza virus enigma. *Cell.* 136(3): 402-410 (2009).
Shimizu K., et al.: Influenza virus inhibits cleavage of the HSP70 pre-mRNAs at the polyadenylation site. *Virology*, 254, 213-219 (1999).
Skehel, J.J., et al., Receptor binding and membrane fusion in virus entry; the influenza hemagglutinin. *Annu. Rev. Biochem.* 69; 531-569 (2000).
Tanaka-M., et al.: Mechanisms of Capsaicin- and Citric-acid-induced cough reflexes in Guinea-Pig. *J. Phamacol. Sci.*, 99, 77-82 (2005).
Ulmanen I., et al.: The role of two of the influenza virus core P proteins in recognizing cap 1 structures (m$^7$GpppNm) on RNAs and in initiating viral RNA transcription. *Proc. Natl. Acad. Sci. USA*, 78(12): 7355-7359 (1981).
Von Itzstein, et al.: Rational Design of Potent Sialidase-Based Inhibitors of Influenza Virus Replication. *Nature*, 363: 418-423 (1993).
Wang G. T., et al.: Design, Synthesis, and Structure Analysis of Influenza Neuraminidase Inhibitors Containing Pyrrolidine Cores. *J. Med. Chem.*, 44: 1192-1201 (2001).
Wang, G.: Recent Advances in the Discovery and Development of Anti-influenza Drugs. *Expert Opin. Ther. Pat.*, 12(6): 845-861 (2002).
Watanabe W., et al. *J. of Virological Methods*, 48: 257 (1994).
Wathen M.W., et al.: Antivirals in seasonal and pandemic influenza-future perspectives. *Influenza and Other Respiratory Virus*, 7(Suppl. 1): 76-80 (2012).
Watson K.G., et al.: Highly potent and long-acting trimeric and tetrameric inhibitors of influenza virus neuraminidase. *Bioorg. Med. Chem. Lett.*, 14, 1589-1592 (2004).
Wu W.W., et al.: The directionality of the nuclear transport of the influenza A genome is driven by selective exposure of nuclear localization sequences on nucleoprotein. *Virol. J.*, 6: 68 (2009).

(56) References Cited

OTHER PUBLICATIONS

Zanini, et al., "Synthesis of New Alpha-Thiosialodedrimers and Their Binding Properties to the Sialic Acid Specific Lectin form Limax flavus", Journal of the American Chemical society, 1997, vol. 119, pp. 2088-2095 (abstract only).
Examination Report in IN Patent Application No. 201817018667 dated Mar. 4, 2020 (with English translation) (7 pages).
First Office Action in ON Patent Application No. 201680075964.X dated Nov. 4, 2020 (with English translation) (25 pages).
Notice of Reasons for Rejection in JP Patent Application No. 2018-525746 dated Oct. 13, 2020 (with English translation) (4 pages).

* cited by examiner

COMPOUNDS FOR MEDICINAL APPLICATIONS

FILING DATA

This application is a continuation of PCT/AU2016/051100, filed Nov. 16, 2016, which is associated with and claims priority from Australian patent application no. 2015904895 filed on 20 Nov. 2015 the entire contents of which is incorporated herein by reference.

FIELD OF INVENTION

This application relates to compounds for medicinal use, in particular for the treatment or prophylaxis of viral infections. This application also relates to methods for preparing the compounds.

BACKGROUND

Influenza is a respiratory infection contracted by 5% to 25% of the US population annually, roughly 200,000 of whom are hospitalized and 25,000 die. Influenza infection continues to be a constant threat to human health and a burden on health services. More recently, the emergence of highly pathogenic H5N1 viruses and H7N9 viruses from avian sources, and their potential to acquire human transmissibility have increased the risk associated with influenza infection. Although vaccines remain the cornerstone of prevention, significant time is required to develop an effective vaccine against frequent mutations of any new virus strain. Anti-influenza drugs such as the viral neuraminidase inhibitors (NA inhibitors), including Zanamivir (Relenza) and Oseltamivir (Tamiflu) and M2 ion-channel blockers derived from adamantanes, including amantidine and rimantidine, are available and have been marketed for over 20 years, but their effectiveness is limited by the mechanism of action. Their effectiveness can be further compromised by viral mutation and development of subsequent drug resistance.

For example, M2 ion-channel blockers are currently not recommended for use because almost all circulating season A virus (including H1Nipcim09), carry a S31N point mutation in the M2 gene that imparts resistance to both amantadine and rimantadine. This has resulted in a heavy reliance on alternative NA inhibitors such as Zanamivir, Oseltamivir and Peramivir.

The NA inhibitors affect the assembly and budding of viruses of Influenza A in the viral life cycle. For the progeny virions to be released from the cell, neuraminidase (NA) must cleave the sialic acid group from the host glycoproteins, which is essential for viral spread and reinfection. Thus, blocking the function of neuraminidase with specific inhibitors (NA inhibitors) is a way of treating influenza. However, as such inhibition occurs in the later stage of the viral life cycle (that is, after viral entry, replication, assembly, and budding onto cell surface), much of the damage has already been done to the cell. Moreover, only the budding viruses on the cell surface have been affected. The uninhibited viral progeny may infect new cells. This leads to the progression of disease severity. In order to reduce severity of the disease, the optimum therapeutic window for treatment with NA inhibitor drugs is early in the disease progression. However, as the therapeutic efficacy of a given active agent is generally determined by the mechanism of action, NA inhibitor drugs are considered to be relatively mild and of limited clinical benefit.

There is a need for new approaches to the treatment of influenza.

The life cycle of Influenza A comprises several steps:

(a) Influenza A virus has a lipid bilayer envelope, within which are eight RNA genomic segments, each of which is associated with the trimeric viral RNA polymerase (PB1, PB2, PA) and coated with multiple nucleoproteins (NPs) to form the vRNPs. The outer layer of the lipid envelope is spiked with multiple copies of HA, NA and a small number of M2, whereas the M1 molecules keep vRNPs attached to the inner layer.

(b) The viral surface glycoprotein HA binds to the host cell-surface sialic acid receptors, and the virus is transported into the cell in an endocytic vesicle. The low pH in the endosome triggers a conformational change in the HA protein that leads to fusion of the viral and endosomal membranes. The low pH also triggers the flow of protons into the virus via the M2 ion channel, thereby dissociating the vRNPs from M1 matrix proteins. When the M1 molecules are dissociated, the vRNPs that are released into the cytoplasm are transported into nucleus by recognition of the nuclear localization sequences (NLSs) on nucleoproteins.

(c) In the nucleus, the viral polymerase initiated viral mRNA synthesis with 5'-capped RNA fragments are cleaved from host pre-mRNAs. The PB2 subunit binds the 5'-cap of host pre-mRNAs, and the endonuclease domain in the PA subunit cleaves the pre-mRNA 10 to 13 nucleotide downstream from the cap. Viral mRNA transcription is subsequently initiated from the cleaved 3'-end of the capped RNA segment. This "cap snatching" occurs on nascent pre-mRNAs.

(d) Viral mRNAs are transported to the cytoplasm for translation into viral proteins. The surface proteins HA, M2 and NA are processed in the endoplasmic reticulum (ER), glycosylated in the Golgi apparatus and transported to the cell membrane.

(e) The NS1 protein of the influenza A virus serves a critical role in suppressing the production of host mRNAs by inhibiting the 3'-end processing of host pre-mRNAs, consequently blocking the production of host mRNAs, including interferon-β mRNAs. Unlike host pre-mRNAs, the viral mRNAs do not require 3'-end processing by the host cell machinery. Therefore, the viral mRNAs are transported to the cytoplasm, whereas the host mRNA synthesis is predominantly blocked.

(f) The viral polymerase is responsible for not only capped RNA-primed mRNA synthesis but also unprimed replication of vRNAs as follows:

(−) vRNA→(+) cRNA→(−) vRNA.

Nucleoprotein molecules are required for these two steps of replication and are deposited on the cRNA and vRNA during RNA synthesis. The resulting vRNPs are subsequently transported to the cytoplasm, mediated by M1-NS2 complex that is bound to the vRNPs; NS2 interacts with human CRM1 protein which export the vRNPs from the nucleus.

(g) The vRNPs reach the cell membrane to be incorporated into new viruses that are budded out. The HA and NA proteins in new viruses contain terminal sialic acids that would cause the viruses to clump together and adhere to the cell surface. The NA of newly formed viruses cleaves these sialic acid residues, thereby releasing the virus from the host cell.

During steps (a) and (b) of the influenza viral life cycle, the viral surface glycoprotein Haemagglutinin (HA) binds to sialic acid receptors on the host cell, followed by receptor-mediated endocytosis of the virus into the cell. The low pH in the endosome triggers a conformational change in the HA protein, that leads to fusion of the viral and endosomal membrane. Meanwhile, the low pH also triggers the flow of protons into the virus via the M2 ion channel, thereby releasing of viral genetic material to the nucleus to start the viral infection process in the cell.

It is recognised that the exposure of virus to low pH in the extracellular environment inactivates the virus. Low pH intranasal gel sprays have been shown to suppress influenza viruses in vitro and protect ferrets against influenza infection. However, in such studies the effective concentration of the acids are around 0.15M (approx. pH 3.5). Furthermore, there needs to be contact with the virus to have a viracidal effect. Additionally, the sprays have demonstrated efficacy only during the early stages of viral infection. Although a pH value close to 3.5 can be achieved by administration of a pH 3.5 buffered nasal spray, there is a limitation of this nasal delivery, which provides the relatively short product retention time in the nose due to mucociliary clearance. The normal residence time of nasally administered solution in human is around 12 to 15 minutes.

Furthermore, in the case of treatment for viral infection, an acidic buffer would need to be delivered deep into the air ways. It is likely that the acidic nature of such a buffer will cause irritation and intolerance in humans. Therefore, acidic intranasal sprays would not be suitable as therapeutic agents for the treatment of influenza virus infection since they are essentially limited and nonspecific.

Polyanionic compounds offer attractive features as anti-HIV agents. The antiviral activity spectrum of the polyanions extends to a variety of enveloped viruses including ortho- and para-myxo viruses (influenza virus). Such polyanions have been shown to inhibit viral replication in cell cultures at a concentration of 0.1 to 1 µg/mL. Advantageously, such compounds are not cytotoxic even at concentrations up to 10,000 fold higher. However, these substances suffer from a number of pharmacokinetic and toxicological drawbacks which seem to compromise their clinical utility, for example, in bloodstream they may be retained by various plasma proteins before reaching their site of action. Additionally, some sulphated polysaccharides are notorious for undesired anticoagulant activity.

There is a need for new antiviral agents which are effective against influenza. In particular, there is a need for new antiviral agents which exhibit one or more of the following: i) high potency against influenza viruses, ii) fast action to control the infection, iii) broad spectrum antiviral activity (including influenza A, B, avian flu), iv) efficacy against drug resistant strains, v) low tendency of drug resistance, vi) extended duration of efficacy, vii) high selectivity, viii) improved therapeutic window; ix) low toxicity, x) fewer side effects and/or xi) are suitable for therapeutic and prophylactic application.

SUMMARY

The present invention provides compounds and methods for the treatment and/or prevention of influenza infection.

The compounds of the present invention, also referred to as "surface engineering compounds", are thought to alter the viral surface, converting the surface into a micro acidic/anionic environment to selectively interfere with the viral life cycle, including steps (a) and (b) outlined above.

This is believed to be achieved by the compounds of the present invention which combine a group which binds to the influenza virus and with an acidic or anionic group(s) which act to interfere with the binding of the haemagglutinin to the cell. This provides an advantage as the compounds of the invention act to prevent infection of the cell and exerts its effect extracellularly. This avoids the need for the molecule to invade the cell which should result in lower toxicity and/or fewer side effects.

In one aspect, the present invention provides a compound comprising a first and second domain,
the first domain comprising at least one anchoring group which binds to the surface of influenza viruses; and
a second domain comprising at least one anionic group;
or a pharmaceutically acceptable salt, solvate, prodrug or stereoisomer thereof, wherein the first and second domains are covalently linked.

In another aspect, there is provided compounds wherein the first and second domains are covalently linked via at least one divalent linker.

In still other aspects, the compounds of the invention may further comprise a multivalent backbone group.

In another aspect, there is provided compounds of Formula (I):

$$[A-L^1+_n B+L^2-C]_p \qquad \text{Formula (I)}$$

or a pharmaceutically acceptable salt, solvate, prodrug or stereoisomer thereof,
wherein:
A at each occurrence is an anchoring group;
B is a multivalent backbone group;
C at each occurrence is an anionic group;
$L^1$ and $L^2$ at each occurrence are divalent linkers;
n is an integer from 1 to 4; and
p is an integer from 1 to 3.

In other aspects, there is provided pharmaceutical compositions comprising a compound of the invention or a pharmaceutically acceptable salt, solvate, prodrug or stereoisomer thereof. In further aspects, there is provided the use of a compound of the invention in the or a pharmaceutically acceptable salt, solvate, prodrug or stereoisomer thereof in the manufacture of a medicament for the treatment or prevention of influenza viral infection.

In other aspects, there is provided methods of treating or preventing influenza viral infection, comprising administering to a person in need thereof a therapeutically effective amount of a compound of the invention or a pharmaceutically acceptable salt, solvate, prodrug or stereoisomer thereof.

In some aspects, the influenza viral infection is influenza A, influenza B, avian flu or a drug resistant strain of influenza.

Unless defined otherwise, all technical and scientific terms used herein have the same meanings as commonly understood by one of ordinary skill in the art to which this invention belongs.

The reference to any prior art in this specification is not, and should not be taken as, an acknowledgment or any form of suggestion that that prior art forms part of the common general knowledge.

All documents cited herein are each incorporated by reference in their entirety.

DETAILED DESCRIPTION

Figure 1:
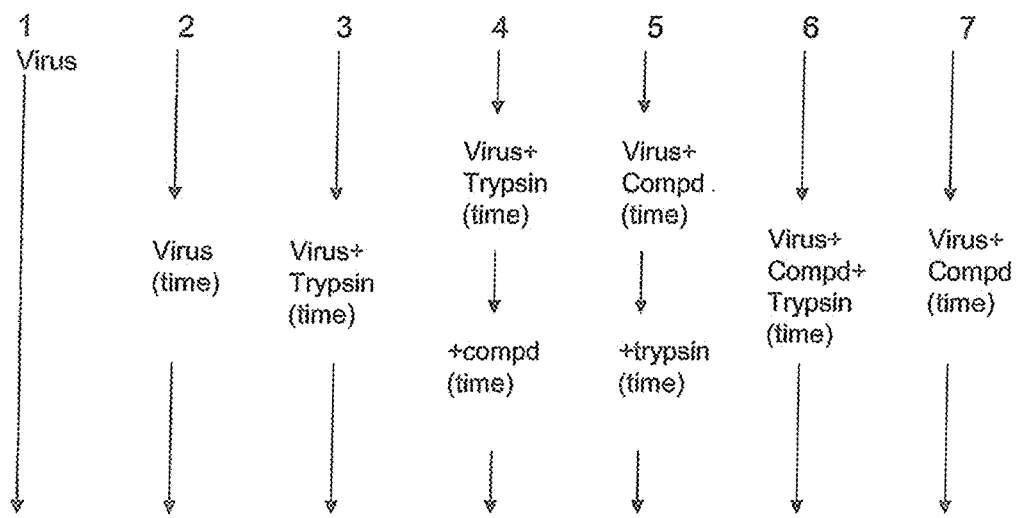
FIG. 1: Summary of variable conditions for pre-treatment of virus (A/Sydney/250/99 or A/Sydney/5/97) with test compounds prior to infection of MDCK cells.

As discussed above the compounds of the present invention are thought to alter the viral surface, converting the surface into a micro acidic/anionic environment to selectively interfere with steps in the viral life cycle.

It is believed that the acidic/anionic groups of the compounds of the present invention convert the viral surface into a micro acidic/anionic environment which reduces or inactivates viral activity. Furthermore, it is believed that these compounds act extracellularly and may therefore be associated with reduced incidence of side effects, reduced toxicity and/or a reduction in the tendency for resistance. More particularly, it is believed that the compounds of the present invention act extracellularly at multiple target points of the viral life cycle, including but not limited to:

Acidic/anionic groups generate a low pH at the viral surface, which triggers premature conformational change in the haemagglutinin (HA) protein, which may subsequently reduce or retard the fusion of the virus and the cells. This is specific to viral life cycle step (b) referred to above.

Additionally, it is believed that the creation of a low pH environment on the viral surface sparks a flow of protons into the virus via M2 ion channel, which may cause the release of genetic material outside of cells. This is specific to viral life cycle step (b) referred to above.

It is believed that the anchor groups of the compounds of the invention may cross link NA/HA and aggregate the virus particles to reduce the mobility and infectivity of viruses. This is specific to viral life cycle steps (a) & (b) referred to above.

It is believed that the anchor groups inhibit the function of neuraminidase (NA) to reduce or prevent the release of new viruses from the cell membrane. This is specific to viral life cycle step (g) referred to above.

It is believed that the disruption of viral life cycle steps (a) and (b) may reduce the potential severity of infection by reducing viral infectivity including viral invasion into cells, viral disruption of normal cell nucleus functions, and/or viral replication. Accordingly, it is considered that the administration of the compounds of the present invention may provide a more effective treatment of viral infection and/or faster recovery for patients than currently available NA inhibitor drugs. Further it is believed that the compounds of the present invention can used prophylactically in the prevention of influenza infection.

Accordingly, in one aspect, the present invention a compound comprising a first and second domain,
    the first domain comprising at least one anchoring group which binds to the surface of influenza viruses; and
    a second domain comprising at least one anionic group;
    or a pharmaceutically acceptable salt, solvate, prodrug or stereoisomer thereof, wherein the first and second domains are covalently linked.

In some aspect, the first and second domains may be covalently linked via at least one divalent linker. In other aspects, the compounds of the invention may further comprise a multivalent backbone group.

In another aspect, the present invention provides compounds of Formula (I):

$$[A-L^1+_nB+L^2-C]_p \qquad \text{Formula (I)}$$

or a pharmaceutically acceptable salt, solvate, prodrug, ester or stereoisomer thereof,
    wherein:
    A at each occurrence is an anchoring group;
    B is a multivalent backbone group;
    C at each occurrence is an anionic group;
    $L^1$ and $L^2$ at each occurrence are divalent linkers;
    n is an integer from 1 to 4; and
    p is an integer from 1 to 4.

As used herein, "a compound of the invention" or "a compound of formula (I)" means a compound or a pharmaceutically acceptable salt, solvate, prodrug, ester or stereoisomer thereof, or a physiologically functional derivative thereof.

The term "anchoring group" as used herein refers to any suitable group which binds to the surface of influenza viruses. In some embodiments, the anchoring group is a group which binds to neuraminidase, such as a neuraminidase inhibitor or a derivative thereof. Examples of suitable groups include, but are not limited to, a sialic acid or a derivative thereof, including N- or O-substituted derivatives of neuraminic acid such as zanamivir or laninamivir, oseltamivir, peramivir, 2,3-difluoro sialic acids (DFSA) and derivatives thereof. In other embodiments, the anchoring group comprises an antibody binding domain which specifically binds neuraminidase. Examples of suitable anchoring group comprising an antibody binding domain which specifically binds neuraminidase include an antibody (Ab) or an antigen binding fragment of an antibody, a single chain antibody fragment (scFV) or a single domain antibody (dAb).

The term "backbone group" as used herein refers any suitable multivalent group to which one or more anchoring groups and one or more acidic or anionic groups are attached. In some aspects, the backbone group may be a trivalent group. In other aspects, the backbone group may be a tetravalent group. Examples of suitable backbone groups include, but are not limited to, optionally substituted propane-1,2,3-tricarboxylate, optionally substituted cyclohexane-1,3,5-tricarboxylate, and optionally substituted benzene-1,2,4,5-tetracarboxylate.

The terms "acidic or anionic group" and "acidic/anionic group" refers to any suitable functional group having acidic and/or anionic properties which acts to interfere with the binding of the haemagglutinin to the cell. Specifically, the term "anionic" describes the net negative charge of a functional group or material. It will be understood that a given negatively charged material may have one or more positively charged counterions associated with it, or vice versa. In solution, a negatively charged material may have dissociated from one or more positively charged counterions with which it is associated. As used herein, the term "anionic" is used to describe a property of that material or functional group and not the overall complex with one or more counterions which will typically render the complex neutral. It is understood that certain functional groups are negatively charged, neutral or positively charged at varying values of pH. Whether a material is anionic will be determined based on the sum of these charges. For example, within the scope of the invention acidic or anionic group may include one or more of the following functional groups carboxylic, sulfonic, phosphoric, and phosphinic acids and their isosteres or bioisosteres. Examples of suitable acidic or anionic groups include, carboxylic acids, amino acids, dipeptides, tripeptides or polypeptides or a derivative thereof having acidic and/or anionic properties, such as aspartic acid, cysteic acid, glutamic acid or peptides derived from aspartic acid, cysteic acid and/or glutamic acid.

The term "sialic acid" is well understood in the art and refers to a 9-carbon monosaccharide, especially those derived from neuraminic acid. Examples of suitable groups include, but are not limited to, optionally substituted monosaccharides derived from N- and/or O-substitutions of N-acetylneuraminic acid (Neu5Ac) and N-glycolylneuraminic acid (Neu5Gc).

The term "neuraminidase inhibitor" is well understood in the art and refers to a class of compounds which block the neuraminidase enzyme. In some embodiments, the anchoring group may be a neuraminidase inhibitor or a derivative thereof. Examples of suitable neuraminidase inhibitors include, but are not limited to, a sialic acid or a derivative of a sialic acid, such as a 2,3-difluoro sialic acid. Other suitable neuraminidase inhibitors include:

Zanamivir

Oseltamivir

Laninamivir

Peramivir and derivatives thereof.

The terms "specific binding" or "specifically binding", as used herein, in reference to the interaction of an antibody with a second chemical species, mean that the interaction is dependent upon the presence of a particular structure (e.g., an antigenic determinant or epitope) on the chemical species; for example, an antibody recognises and binds to a specific protein structure rather than to proteins generally.

The term "antibody", as used herein, broadly refers to any immunoglobulin (Ig) molecule comprised of four polypeptide chains, two heavy (H) chains and two light (L) chains, or any functional fragment, mutant, variant, or derivation thereof, which retains the essential epitope binding features of an Ig molecule. Such mutant, variant, or derivative antibody formats are known in the art. Non-limiting embodiments of which are discussed below.

In a full-length antibody, each heavy chain is comprised of a heavy chain variable region (abbreviated herein as HCVR or VH) and a heavy chain constant region. The heavy chain constant region is comprised of three domains, CH1, CH2 and CH3. Each light chain is comprised of a light chain variable region (abbreviated herein as LCVR or VL) and a light chain constant region. The light chain constant region is comprised of one domain, CL. The VH and VL regions can be further subdivided into regions of hypervariability, termed complementarity determining regions (CDR), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4. Immunoglobulin molecules can be of any type (e.g., IgG, IgE, IgM, IgD, IgA and IgY), class (e.g., IgG1, IgG2, IgG 3, IgG4, IgA1 and IgA2) or subclass.

The term “antigen binding domain” or “antigen binding fragment” of an antibody, as used herein, refers to one or more fragments of an antibody or protein that retain the ability to specifically bind to an antigen (e.g., IL-12). It has been shown that the antigen-binding function of an antibody can be performed by fragments of a full-length antibody. Such antibody embodiments may also be bispecific, dual specific, or multi-specific formats; specifically binding to two or more different antigens. Examples of binding fragments encompassed within the term “antigen-binding portion” of an antibody include (i) a Fab fragment, a monovalent fragment consisting of the VL, VH, CL and CH1 domains; (ii) a F(ab')2 fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al, 1989 Nature 341 544-6, Winter et al., PCT publication WO 90/05144 A1 herein incorporated by reference), which comprises a single variable domain; and (vi) an isolated complementarity determining region (CDR). Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv); (see e.g., Bird et al, 1988 Science 242 423-6; Huston et al, 1988 Proc Natl Acad Sci USA 85 5879-83). Such single chain antibodies are also intended to be encompassed within the term “antigen-binding portion” of an antibody. Other forms of single chain antibodies, such as diabodies are also encompassed. Diabodies are bivalent, bispecific antibodies in which VH and VL domains are expressed on a single polypeptide chain, but using a linker that is too short to allow for pairing between the two domains on the same chain, thereby forcing the domains to pair with complementary domains of another chain and creating two antigen binding sites (see e.g., Holliger, P., et al., 1993, Proc. Natl. Acad. Sci. USA 90:6444-6448; Poljak, R. J., et al., 1994, Structure 2:1121-1123). Such antibody binding portions are known in the art (Kontermann and Dubel eds., Antibody Engineering 2001 Springer-Verlag. New York. 790 pp., ISBN 3-540-41354-5).

In one embodiment, the anchoring group at each occurrence is any suitable anchoring group which binds to the surface of influenza viruses. In some embodiments, the anchoring group at each occurrence is a group which binds to neuraminidase, including a neuraminidase inhibitor or a derivative thereof. In certain embodiments, the anchoring group is a neuraminidase inhibitor or a derivative thereof selected from a sialic acid, such as zanamivir or laninamivir, a 2,3-difluoro sialic acid, oseltamivir, peramivir, and derivatives thereof. In other embodiments, the anchoring group at each occurrence comprises an antibody binding domain which specifically binds neuraminidase. In certain embodiments where the anchoring group is an antibody binding domain which specifically binds neuraminidase, the anchoring group is selected from the group consisting of an antibody (Ab), an antigen binding fragment of an antibody, a single chain antibody fragment (scFV) and a single domain antibody (dAb). The compounds of the invention may comprise a total of 1 to 6 anchoring groups, preferably 2 to 4 anchoring groups, more preferably 2 anchoring groups.

In another embodiment, the anchoring group is a monovalent radical derived from a group of formula II (Formula II)

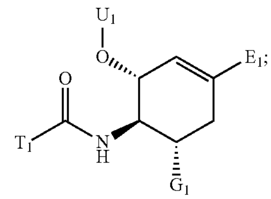

a group of formula III (Formula III)

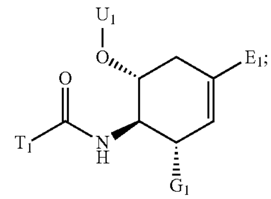

a group of formula IV (Formula IV)

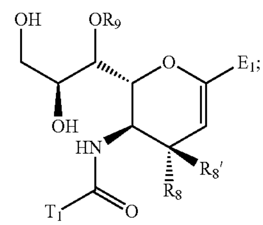

and a group of formula V (Formula V)

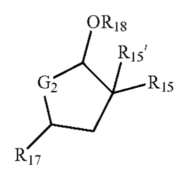

wherein $E_1$ is selected from the group consisting of —COOH, $COOHR_6$, —$SO_3H$, —$PO_3H_2$, —$PO(OR_6)_2$ $G_1$ is selected from —$NH_2$, —$CH_2NH_2$, —$(CH_2)_2NH_2$, 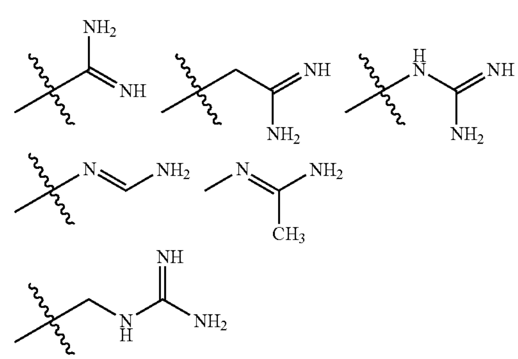 $T_1$ is selected from the group consisting of an optionally substituted $C_1$-$C_6$ alkyl, optionally substituted $C_2$-$C_6$ alkenyl, or an optionally substituted $C_2$-$C_6$ alkynyl $U_1$ is selected from the group consisting of —CH$_2$R$_7$, —(CH$_2$)$_2$R$_7$, —CH$_2$CHR$_7$CH$_2$R$_7$ $R_7$ is selected from the group consisting of H, —OH, —OCH$_3$, —OAc, —NH$_2$, or —SH.

$R_8$ and $R_{8'}$ are each independently selected from the group consisting of hydrogen —N$_3$, —CN, —CH$_2$NH$_2$, guanadino, or —NR$_{10}$R$_{11}$;

$R_9$ is selected from hydrogen, optionally substituted C$_1$-C$_6$ alkyl, optionally substituted C$_2$-C$_6$ alkenyl, or optionally substituted C$_2$-C$_6$ alkynyl;

$R_{10}$ and $R_{11}$ are each independently selected from the group consisting of hydrogen, optionally substituted C$_1$-C$_6$ alkyl group, optionally substituted C$_1$-C$_6$ acyl, —C(NH)NH$_2$, —CH$_2$COOH, CH$_2$CH$_2$OH or —CH$_2$CH(R$_{12}$)(R$_{13}$), $R_{12}$ and $R_{13}$ are each independently selected from O and $R_{14}$N=, and $R_{14}$ is selected from the group consisting of hydrogen, —OH, —OCH$_3$, —NH$_2$, and —N(CH$_3$)$_2$, $R_{15}$ and $R_{15'}$ are each independently selected from hydrogen and CO$_2$R$_{16}$, $R_{16}$ is H or optionally substituted C$_1$-C$_6$ alkyl;

$R_{17}$ is selected from NH$_2$ and —NHC(=NH)NH$_2$;

$G_2$ is

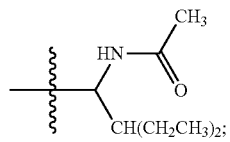

$R_{18}$ is selected from the group consisting of hydrogen, optionally substituted C$_1$-C$_6$ alkyl, optionally substituted C$_2$-C$_6$ alkenyl, and optionally substituted C$_2$-C$_6$ alkynyl.

In still other embodiments, the anchoring group at each occurrence is selected from the group consisting of a group of Formula VI and a group of Formula VII:

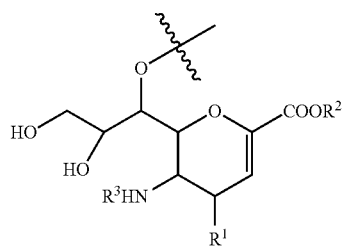
(Formula VI)

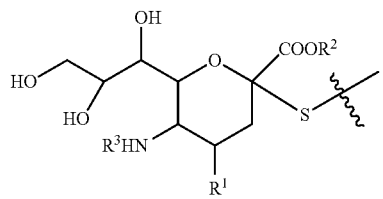
(Formula VII)

wherein R$^1$ is selected from the group consisting of —NR$_2$, guandino, —ONR$_2$, wherein R is H or optionally substituted C$_1$-C$_6$ alkyl, R$^2$ is selected from the group consisting of H, optionally substituted C$_1$-C$_6$ alkyl, and optionally substituted aryl, and R$^3$ is selected from the group consisting of H, optionally substituted C$_1$-C$_6$ alkyl, optionally substituted aryl, and optionally C$_1$-C$_6$ acyl.

In another embodiment, the anchoring group is a group of Formula (VIa):

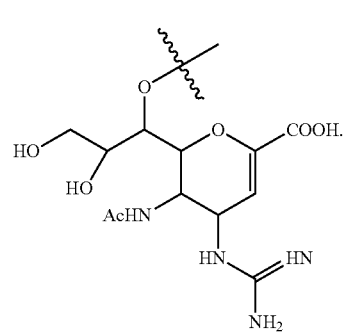
(Formula VIa)

In a further embodiment, the anchoring group is a group of Formula (VIIa):

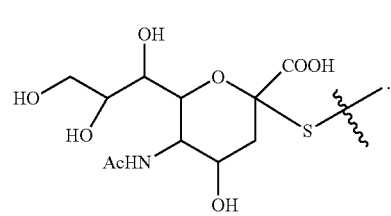
(Formula VIIa)

In an embodiment, the linker (such as L$^1$ and/or L$^2$ of Formula I) at each occurrence is any suitable divalent linker. In one embodiment, the linker at each occurrence is independently selected from a bond, an optionally substituted C$_1$-C$_{12}$ alkylene, —C(O)—NR—, —O—C(O)O—NR—, —C=N—O—, —C=N—NR—, —SO$_2$—NR—, disulfide, —C(O)—NR—(CH$_2$)$_x$—NR—, —(CH$_2$)$_x$—NR—, —(CH$_2$)$_x$—(O—(CH$_2$)$_y$—)$_z$—, optionally substituted-C=N—O—, optionally substituted —C=N—NR-alkylene, optionally substituted alkylene sulfonamide, an optionally substituted alkylene disulfide, wherein R is independently H or C$_1$-C$_6$ alkyl and wherein x, y and z are each integers independently selected from 0, 1, 2, 3 and 4.

In one embodiment wherein the anchoring group is a group of Formula (VI) or Formula (VIa), the linker L$^1$ of Formula (I) is selected from —C(O)—NR—(CH$_2$)$_x$—NR—, —(CH$_2$)$_x$—NH— and —(CH$_2$)$_x$—(O—(CH$_2$)$_y$)$_z$, wherein x, y and z are each integers independently selected from 0, 1, 2, 3 and 4. In another embodiment wherein the anchoring group is a group of Formula (VII) or Formula (VIIa), the linker L$^1$ of Formula (I) is —(CH$_2$)$_x$—NH—, wherein x is an integer selected from 0, 1, 2, 3 and 4.

In one embodiment, the linker L$^2$ of Formula (I) is a bond.

In an embodiment, the backbone group is any suitable multivalent group. In one embodiment, the backbone group is a trivalent backbone group. In another embodiment, the backbone group is a tetravalent backbone group. In one embodiment, the backbone group is selected from an optionally substituted tricarboxylate group, an optionally substituted tetracarboxylate group or a multivalent peptide. In other embodiments, the backbone group is selected from optionally substituted propane-1,2,3-tricarboxylate, optionally substituted prop-1-ene-1,2,3-tricarboxylate, optionally substituted cyclopropane-1,2,3-tricarboxylate, optionally substituted cyclohexane-1,3,5-tricarboxylate, optionally substituted benzene-1,3,5-tricarboxylate, optionally substituted methane tetracarboxylate, optionally substituted 1,2,3,4-butane tetracarboxylate, optionally substituted ethylene-1,1,2,2-tetracarboxylate, such as ethylenediaminetetraacetic acid (EDTA), optionally substituted cyclohexane-1,2,4,5-tetracarboxylate, and optionally substituted benzene-1,2,4,5-tetracarboxylate. In still other embodiments, the backbone group is selected from optionally substituted propane-1,2,3-tricarboxylate, optionally substituted cyclohexane-1,3,5-tricarboxylate, optionally substituted benzene-1,2,4,5-tetracarboxylate, optionally substituted pyromellitic acid and optionally substituted di-pyromellitic acid formed by —C(O)—NH—NH—C(O)— bond (5,5'-(hydrazine-1,2-dicarbonyl)bis(benzene-1,2,4-tricarboxylic acid). In still other embodiments, the backbone group is a multivalent peptide.

In an embodiment, the acidic or anionic group is any suitable functional group having acidic and/or anionic properties which acts to interfere with the binding of the haemagglutinin to the cell. In some embodiments, the acidic or anionic group is any suitable group comprising one or more functional groups selected from carboxylic acids, sulfonic acids, phosphoric acids, and phosphinic acids and their isosteres or bioisosteres. In some embodiments, the acidic or anionic group is any suitable amino acid, a dipeptide, a tripeptide, a polypeptide or derivatives thereof comprising one or more acidic functional groups. In one embodiment, the acidic or anionic group is aspartic acid, cysteic acid, glutamic acid or peptides derived from aspartic acid, cysteic acid and/or glutamic acid.

In an embodiment, the compounds of the invention comprise a total of 2 to 26 acidic/anionic residues, preferable 4 to 10 acidic/anionic residues. For example, where the acidic or anionic group comprises a dicarboxylic acid, it is appreciated that such a moiety comprises two distinct acidic/anionic residues. By way of example with reference to the representative examples of compounds of the invention, it is noted that MD349 comprises a total of nine acidic or anionic residues (five carboxylic acid residues and four sulfonic acid residues), MD348 comprises a total of seven acidic or anionic residues (four carboxylic acid residues and three sulfonic acid residues), MD345 comprises a total of eight acidic or anionic residues (one carboxylic acid residues and seven sulfonic acid residues), MD352 comprises a total of nine acidic or anionic residues (two carboxylic acid residues and seven sulfonic acid residues), MD356 comprises a total of six acidic or anionic residues (two carboxylic acid residues and four sulfonic acid residues), MD357 comprises a total of six acidic or anionic residues (two carboxylic acid residues and four sulfonic acid residues), MD358 comprises a total of eight acidic or anionic residues (eight carboxylic acid residues), MD359 comprises a total of eight acidic or anionic residues (two carboxylic acid residues and six sulfonic acid residues), MD373 comprises a total of eight acidic or anionic residues (eight carboxylic acid residues), and MD376 comprises a total often acidic or anionic residues (ten carboxylic acid residues).

In another embodiment, the acidic or anionic group is a group of Formula VIII:

(Formula VIII)

wherein
$R^4$ at each occurrence is independently selected from the group consisting of —COOH, —SO$_3$H, —NHCH$_2$SO$_3$H, —CONH-Cya, —CONH-Asp, —CONH-Asp(-NHCH$_2$SO$_3$H)$_w$, and —CONH-Asp(-NHCH$_2$PO$_3$H)$_w$, wherein w is an integer 1 or 2;
$R^5$ is selected from the group consisting of —OH and —NHCH$_2$SO$_3$H
u is an integer from 0 to 3;
t is an integer from 0 to 3;
r is an integer from 0 to 6;
v is an integer from 1 to 12.

In an embodiment, n is an integer from 1 to 4. In another embodiment, n is an integer from 1 to 3. In certain embodiments, n is 1. In other embodiments, n is 2. In still other embodiments, n is 3. In further embodiments, n is 4.

In an embodiment, p is an integer from 1 to 4. In another embodiment, p is an integer from 1 to 2. In certain embodiments, p is 1. In other embodiments, p is 2. In still other embodiments, p is 3. In further embodiments, p is 4.

Additionally, or alternatively, in some embodiments the compounds of Formula (I) may be modified, either before, during, or after assembly, to enhance or modify the biological activity and/or binding affinity for the influenza virus surface. In an embodiment, where the acidic or anionic groups comprise one or carboxylic acids, including amino acids, the carboxylic acid may be modified by sulfation, phosphorylation, functional group interconversion, and/or attachment of side chains. For example, where the acidic or anionic groups comprises a carboxylic acid, the carboxylic acid may be modified to an amide or sulphated amide, including —C(=O)NH(CH$_2$)$_n$SO$_3$H. Alternatively, or additionally, where the acidic or anionic groups comprise an amino acid or peptide, the C-terminus may be modified to include alternative functional groups, such as conversion of the terminal acid to an amide or sulphated amide including —C(=O)NH(CH$_2$)$_n$SO$_3$H.

With respect to formula (I) compounds disclosed herein the following combinations of any or more of (i) to (vii) are contemplated:
(i) A is Formula (IIa); or
  A is Formula (IIIa);
(ii) B is propane-1,2,3-tricarboxylic acid; or
  B is cyclohexane-1,3,5-tricarboxylate, or
  B is benzene-1,2,4,5-tetracarboxylate;
(iii) $L^1$ is —C(O)—NH—; or
  $L^1$ is —C(O)—NH—(CH$_2$)$_2$—NH—; or
  $L^1$ is —C(O)—NH—(CH$_2$)$_3$—NH—; or $L^1$ is —C(O)—NH—(CH$_2$)$_4$—NH—; or
$L^1$ is —C(O)—NH—(CH$_2$)$_5$—NH—; or
$L^1$ is —C(O)—NH—(CH$_2$)$_6$—NH—; or
$L^1$ is —C(O)—NH—(CH$_2$)$_7$—NH—; or
$L^1$ is —C(O)—NH—(CH$_2$)$_8$—NH—; or
$L^1$ is —C(O)—NH—(CH$_2$)$_9$—NH—; or
$L^1$ is —C(O)—NH—(CH$_2$)$_{10}$—NH—; or
$L^1$ is —C(O)—NH—(CH$_2$)$_{12}$—NH—; or
$L^1$ is —(CH$_2$)$_6$—NH—; or
$L^1$ is —(CH$_2$)$_8$—NH—; or
$L^1$ is —(CH$_2$)$_9$—NH—; or
$L^1$ is —(CH$_2$)$_{10}$—NH—; or
$L^1$ is —(CH$_2$)$_{12}$—NH—;
(iv) $L^2$ is a bond:
(v) C is L-aspartic acid; or
C is D-aspartic acid; or
C is L-cysteic acid; or
C is D-cysteic acid; or
C is -(L-Asp)$_2$-OH; or
C is -(D-Asp)$_2$-OH; or
C is -(L-Cya)$_2$-OH; or
C is -(D-Cya)$_2$-OH; or
C is -(L-Asp)$_3$-OH; or
C is -(D-Asp)$_3$-OH; or
C is -(L-Cya)$_3$-OH; or
C is -(D-Cya)$_3$-OH; or
C is -(L-Cya)$_7$-OH; or
C is -(D-Cya)$_7$-OH; or
C is -(L-Asp-L-Cya)$_4$-OH; or
C is -(L-Asp-L-Cya)$_4$-OH; or
C is -[L-Asp(L-Cya)]$_3$-OH; or
C is -[D-Asp(D-Cya)]$_3$-OH; or
C is -[L-Asp(L-Cya)]$_4$-OH; or
C is -[(L-Asp)$_4$-(L-Cya)$_3$]-OH; or
C is -[(D-Asp)$_4$-(D-Cya)$_3$]-OH; or
C is -[L-Asp(L-Cya)]$_3$-OH; or
C is -[D-Asp(D-Cya)]$_3$-OH; or
C is -[L-Asp(L-Cya)]$_4$-OH; or
C is -[D-Asp(D-Cya)]$_4$-OH; or
C is L-Asp(NHCH$_2$SO$_3$H)$_2$; or
C is D-Asp(NHCH$_2$SO$_3$H)$_2$; or
C is -[L-Asp(NHCH$_2$SO$_3$)]$_3$NHCH$_2$SO$_3$H; or
C is -[D-Asp(NHCH$_2$SO$_3$)]$_3$NHCH$_2$SO$_3$H;
C is D-aspartic acid; or
C is L-cysteic acid; or
C is D-cysteic acid; or
C is -(L-Asp)$_2$-OH; or
C is -(D-Asp)$_2$-OH; or
C is -(L-Cya)$_2$-OH; or
C is -(D-Cya)$_2$-OH; or
C is -(L-Asp)$_3$-OH; or
C is -(D-Asp)$_3$-OH; or
C is -(L-Cya)$_3$-OH; or
C is -(D-Cya)$_3$-OH; or
C is -(L-Cya)$_7$-OH; or
C is -(D-Cya)$_7$-OH; or
C is -(L-Asp-L-Cya)$_4$-OH; or
C is -(L-Asp-L-Cya)$_4$-OH; or
C is -[L-Asp(L-Cya)]$_3$-OH; or
C is -[D-Asp(D-Cya)]$_3$-OH; or
C is -[L-Asp(L-Cya)]$_4$-OH; or
C is -[(L-Asp)$_4$-(L-Cya)$_3$]-OH; or
C is -[(D-Asp)$_4$-(D-Cya)$_3$]-OH; or
C is -[L-Asp(L-Cya)]$_3$-OH; or
C is -[D-Asp(D-Cya)]$_3$-OH; or
C is -[L-Asp(L-Cya)]$_4$-OH; or
C is -[D-Asp(D-Cya)]$_4$-OH; or
C is L-Asp(NHCH$_2$SO$_3$H)$_2$; or
C is D-Asp(NHCH$_2$SO$_3$H)$_2$; or
C is -[L-Asp(NHCH$_2$SO$_3$)]$_3$—NHCH$_2$SO$_3$H; or
C is -[D-Asp(NHCH$_2$SO$_3$)]$_3$—NHCH$_2$SO$_3$H;
(vi) n is 2; or
n is 3
n is 3
(vii) p is 1; or
p is 2.
p is 2.

For ease or reference, representative examples of compounds of the invention may be abbreviated. For example, in the context of the representative examples, for ease reference, the anchoring group (including A of Formula (I)) and linker (including $L_1$) of Formula (I), at each occurrence, may be represented as a single group, referred to as $Z_x$ or $S_y$. Specifically, where the compounds of the invention comprise a group of Formula $Z_x$, such groups are sialic acid derivatives in which a functional group (amino or guanidino) replaces the hydroxyl group at 4-position of sialic acid ring. Such a modification enables the groups of Formula $Z_x$, to interact with influenza viral neuraminidases, but not with m Formula $S_y$

[Structure: sugar derivative with OH, HO, HO, AcHN, OH groups on pyranose ring, with COOH and S—(CH$_2$)$_Y$NH— substituents]

| Structure $S_y$ | Abbreviation |
|---|---|
| Y is 6 | $S_6$ |
| Y is 8 | $S_8$ |
| Y is 9 | $S_9$ |
| Y is 10 | $S_{10}$ |
| Y is 12 | $S_{12}$ |

For ease or reference, in the context of the representative examples, the compounds from which the backbone group B of Formula (I) may be derived are abbreviated as follows

| Abbreviation | Structure | Name |
|---|---|---|
| CHTCA | [cyclohexane with three COOH groups] | cis-1,3,5-cyclohexanetricarboxylic acid |
| TCA | [CH(COOH)(CH$_2$COOH)$_2$] | Tricarboxylic acid |
| PYR | [benzene with 4 COOH groups at 1,2,4,5] | Pyromellitic acid |
| PYR-NH-NH-PYR | | Di-pyromellitic acid with a C(O)—NH—NH—C(O) bond 5,5'-(hydrazine-1,2-dicarbonyl)bis(benzene-1,2,4-tricarboxylic acid) |

For ease or reference, in the context of the representative examples, the anchoring group A, linker $L^1$ and backbone group B of Formula (I), may be abbreviated as follows:

| Abbreviation | Structure | Abbreviation | Structure |
|---|---|---|---|
| PK2 TCA(Z$_x$)$_2$ | [CH(COZ$_X$)(CH$_2$COOH)(CH$_2$COZ$_X$)] | PK1 CA(Z$_x$)$_2$ | [CH(COOH)(CH$_2$COZ$^X$)(CH$_2$COZ$_X$)] |
| PK1 PYR(Z$_x$)$_2$ | [benzene with HOOC, COZ$_X$, Z$_X$OC, COOH] | PK2 PYR(Z$_x$)$_2$ | [benzene with Z$_X$OC, COZ$_X$, HOOC, COOH] |
| CHTCA(Z$_x$)$_2$ | [cyclohexane with COOH, Z$_X$OC, COZ$_X$] | CHTCA(S$_y$)$_2$ | [cyclohexane with COOH, S$_y$OC, COS$_y$] |
| PK2 TCA(S$_y$)$_2$ | [CH(COS$_y$)(CH$_2$COOH)(CH$_2$COS$_y$)] | PK1 TCA(S$_y$)$_2$ | [CH(COOH)(CH$_2$S$_y$OC)(CH$_2$COS$_y$)] |
| PK1 PYR(S$_y$)$_2$ | [benzene with HOOC, COS$_y$, S$_y$OC, COOH] | PK2 PYR(S$_y$)$_2$ | [benzene with S$_y$OC, COS$_y$, HOOC, COOH] |

| Abbreviation | Structure | Abbreviation | Structure |
|---|---|---|---|
| CHTCA($Z_x$)($S_y$) | cyclohexane with COOH (top), $S_yOC$ and $COZ_x$ substituents | CHTCA($Z_x$)$_2$($S_y$) | |
| PK1 PYR($Z_x$)$_2$($S_y$) | benzene with $Z_xOC$, COOH, $S_yOC$, $COZ_x$ substituents | PK2 PYR($Z_x$)$_2$($S_y$) | benzene with $S_yOC$, COOH, $Z_xOC$, $COZ_x$ substituents |
| PK2PYR($Z_x$)$_2$(NHCH$_2$SO$_3$H)$_2$ | benzene tetrasubstituted: HO$_3$SCH$_2$NHC(O)-, -C(O)NHCH$_2$SO$_3$H, -C(O)$Z_x$, -C(O)$Z_x$ | | 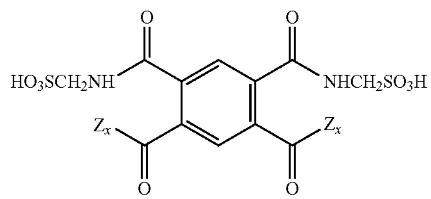 |

For ease or reference, in the context of the representative examples, the compounds from which the acidic or anionic groups of Formula (I) may be derived, are abbreviated as follows:

| Abbreviation | Structure | Name |
|---|---|---|
| Cya<br>Cya-SO$_3$H | HOOC-CH(NH$_2$)-CH$_2$-SO$_3$H | Cysteic acid |
| L-Cya<br>L-Cya-SO$_3$H | (S)-HOOC-CH(NH$_2$)-CH$_2$-SO$_3$H | L-Cysteic acid |
| D-Cya<br>D-Cya-SO$_3$H | (R)-HOOC-CH(NH$_2$)-CH$_2$-SO$_3$H | D-Cysteic acid |
| Asp | | Aspartic acid |
| L-Asp | (S)-HOOC-CH(NH$_2$)-CH$_2$-COOH | L-Aspartic acid |
| D-Asp | (R)-HOOC-CH(NH$_2$)-CH$_2$-COOH | D-Aspartic acid |

-continued

| Abbreviation | Structure | Name |
|---|---|---|
| (L-Asp)$_3$ or L-Asp-L-Asp-L-Asp | 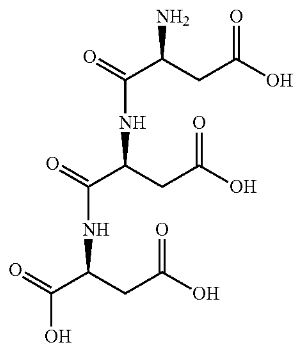 [SMILES: N[C@@H](CC(=O)O)C(=O)N[C@@H](CC(=O)O)C(=O)N[C@@H](CC(=O)O)C(=O)O] | |
| (D-Asp)$_3$ or D-Asp-D-Asp-D-Asp | 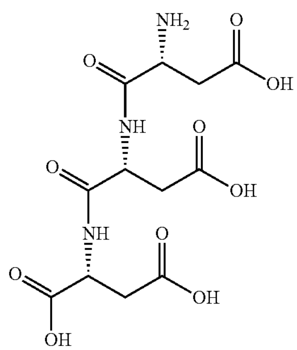 [SMILES: N[C@H](CC(=O)O)C(=O)N[C@H](CC(=O)O)C(=O)N[C@H](CC(=O)O)C(=O)O] | |
| (L-Cya)$_3$ or L-Cya-L-Cya-L-Cya | 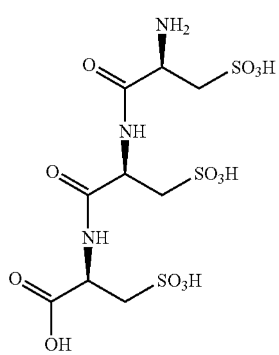 [SMILES: N[C@@H](CS(=O)(=O)O)C(=O)N[C@@H](CS(=O)(=O)O)C(=O)N[C@@H](CS(=O)(=O)O)C(=O)O] | |
| (D-Cya)$_3$ or D-Cya-D-Cya-D-Cya | 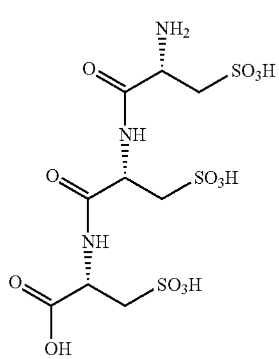 [SMILES: N[C@H](CS(=O)(=O)O)C(=O)N[C@H](CS(=O)(=O)O)C(=O)N[C@H](CS(=O)(=O)O)C(=O)O] | |

| Abbreviation | Structure | Name |
|---|---|---|
| (L-Cya)7-OH or (L-Cya)7 | 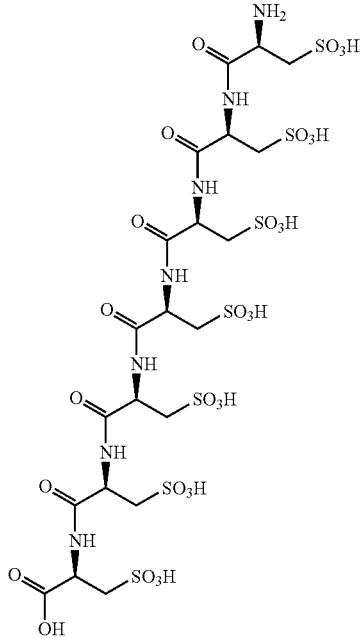 [SMILES: N[C@@H](CS(=O)(=O)O)C(=O)N[C@@H](CS(=O)(=O)O)C(=O)N[C@@H](CS(=O)(=O)O)C(=O)N[C@@H](CS(=O)(=O)O)C(=O)N[C@@H](CS(=O)(=O)O)C(=O)N[C@@H](CS(=O)(=O)O)C(=O)N[C@@H](CS(=O)(=O)O)C(=O)O] | |
| (D-Cya)7-OH (D-Cya)7 | 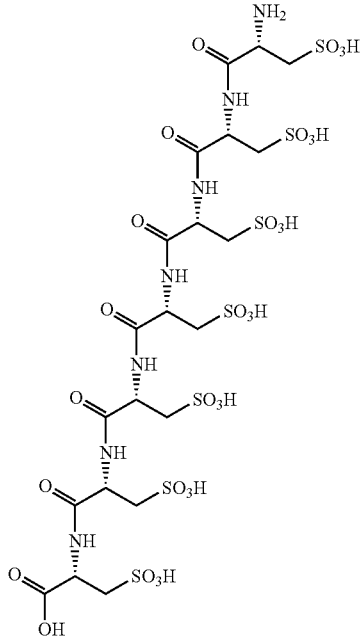 [SMILES: N[C@H](CS(=O)(=O)O)C(=O)N[C@H](CS(=O)(=O)O)C(=O)N[C@H](CS(=O)(=O)O)C(=O)N[C@H](CS(=O)(=O)O)C(=O)N[C@H](CS(=O)(=O)O)C(=O)N[C@H](CS(=O)(=O)O)C(=O)N[C@H](CS(=O)(=O)O)C(=O)O] | |

| Abbreviation | Structure | Name |
|---|---|---|
| L-Asp(L-Cya)-L-Asp(L-Cya)-L-Asp(L-Cya)-OH or [L-Asp(L-Cya)]₃ | | |
| D-Asp(D-Cya)-D-Asp(D-Cya)-D-Asp(D-Cya)-OH or [D-Asp(D-Cya)]₃ | | |
| Asp(NHCH₂SO₃H)-Asp(NHCH₂SO₃H)-Asp(NHCH₂SO₃H)₂ | | |
| L-(Asp)(β)-L-(Asp)(β)-L-(Asp) | | |

-continued

| Abbreviation | Structure | Name |
|---|---|---|
| D-(Asp)(β)-D-(Asp)(β)-D-(Asp) | 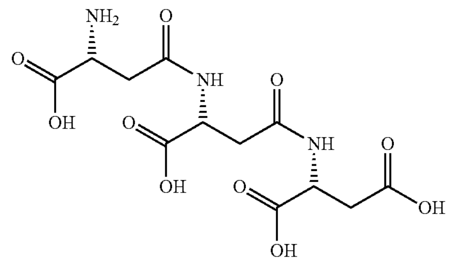 | |
| L-(Asp)(β)-D-(Asp)(β)-L-(Asp) | 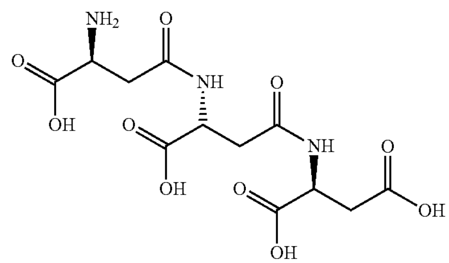 | |
| D-Asp(L-Asp)-D-Asp(L-Asp)-D-Asp(L-Asp) | 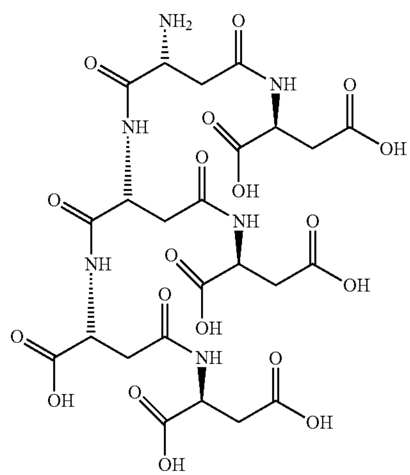 | |

Representative examples of compounds of the invention are outlined below.

| Ref. No. | Abbreviated Ref. | Structure |
|---|---|---|
| MD021 Mol. Weight. 1243 | CHTCA(Z)$_2$-L-Asp | 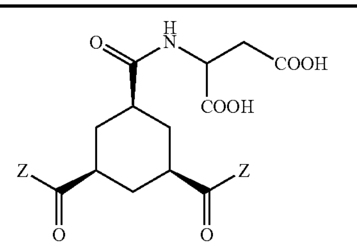 |

-continued
| Ref. No. | Abbreviated Ref. | Structure |
|---|---|---|
| M0154 Mol. Weight. 1485 | CHTCA($Z_0$)$_2$-L-Asp(NHCH$_2$SO$_3$H)$_2$ | 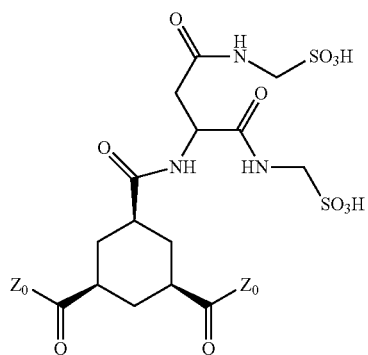 |
| M0155 Mol. Weight. 1485 | CHTCA($Z_0$)$_2$-D-Asp(NHCH$_2$SO$_3$H)$_2$ | 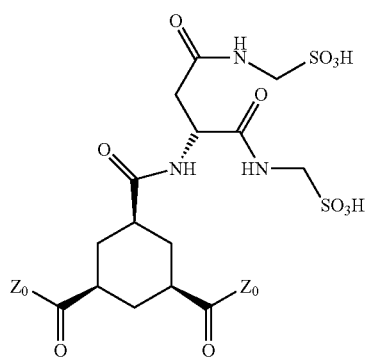 |
| MD012 Mol. Weight. 1534 | CHTCA(Z)$_2$(S$_6$) | 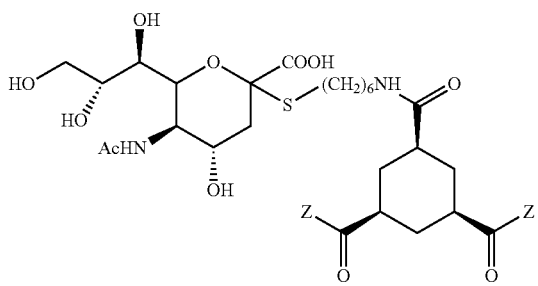 |
| MD051 Mol. Weight. 1318 | PK2 TCA(Z)$_2$-[L-Asp-L-Asp] | 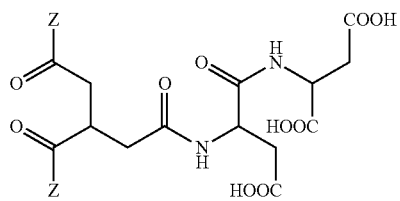 |

| Ref. No. | Abbreviated Ref. | Structure |
|---|---|---|
| MD185<br>Mol. Weight.<br>1852 | PK2PYR($Z_n$)$_2$[(D-Asp)(NHCH$_2$SO$_3$)$_2$]$_2$ | |
| MD314<br>Mol. Weight.<br>1982 | CHTCA($Z_0$)-L-Asp(L-Cya)-L-Asp-(L-Cya)-L-Asp(L-Cya) | |

-continued

| Ref. No. | Abbreviated Ref. | Structure |
|---|---|---|
| MD317 Mol. Weight. 1318 | PK2 TCA(Z)₂-[D-Asp-D-Asp] | 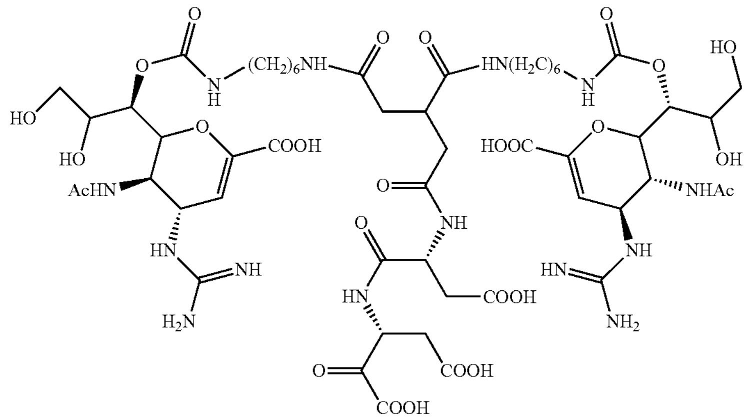 |
| MD342 Mol. Weight. 2208 | PK2 TCA(Z₀)₂-[D-Asp-D-Cya]₄-OH | 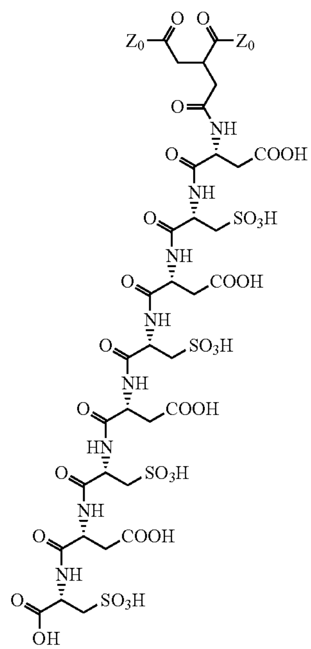 |
| MD343 Mol. Weight. 1597 | PK2 TCA(Z₀)₂-[D-Cya]₃-OH | 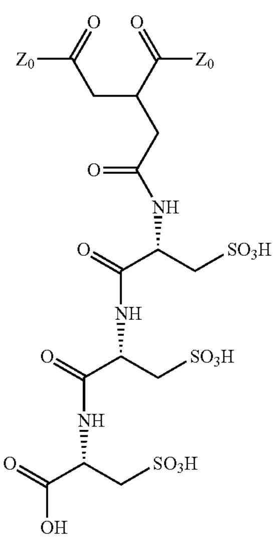 |

| Ref. No. | Abbreviated Ref. | Structure |
|---|---|---|
| MD344 Mol. Weight. 2058 | PK2 TCA($Z_0$)$_2$[(D-Asp)$_4$D-Cya)$_3$]-OH | 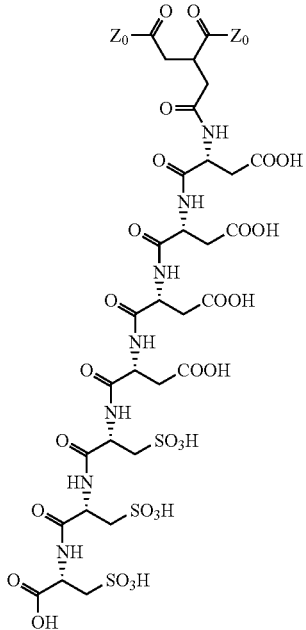 |
| MD345 Mol. Weight. 2201 | PK2TCA($Z_0$)$_2$-[(D-Cya (SO$_3$H)]$_7$-OH | 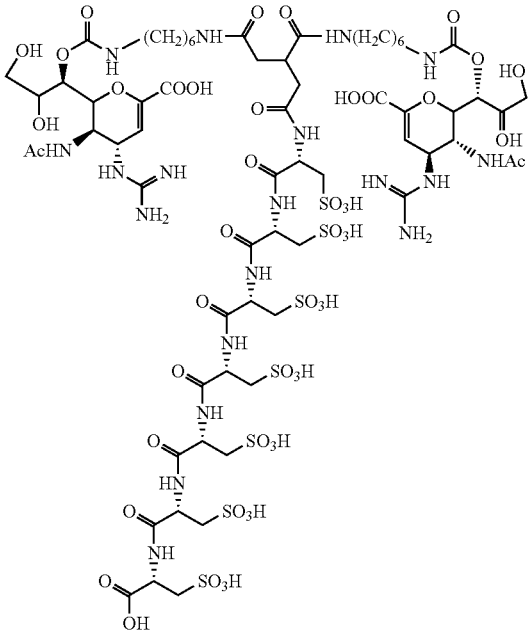 |

-continued

| Ref. No. | Abbreviated Ref. | Structure |
|---|---|---|
| MD348 Mol. Weight. 1982 | CHTCA(Z₀)₂-[D-Asp(D-Cya)-D-Asp(D-Cya)-D-Asp(D-Cya)]-OH | 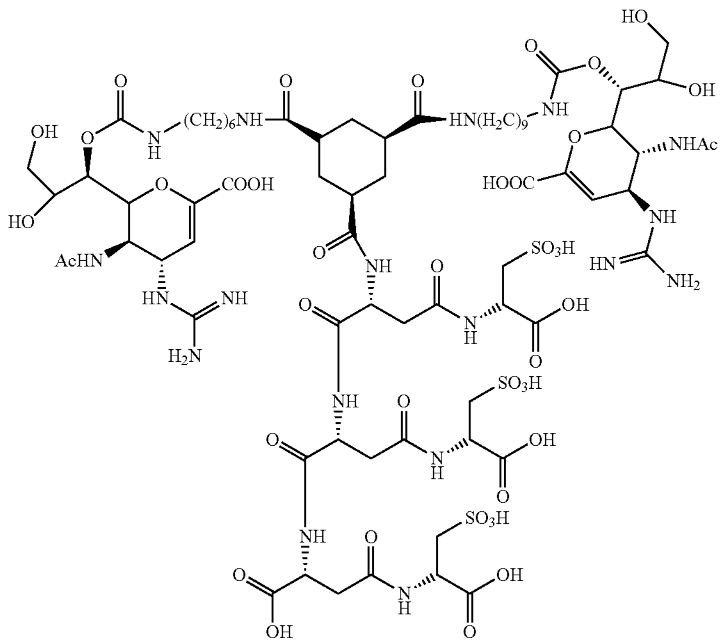 |
| MD349 Mol. Weight. 2248 | CHTCA(Z₀)[D-Asp(D-Cya)-D-Asp(D-Cya)-D-Asp(D-Cya)-D-Asp(D-Cya)]-OH | 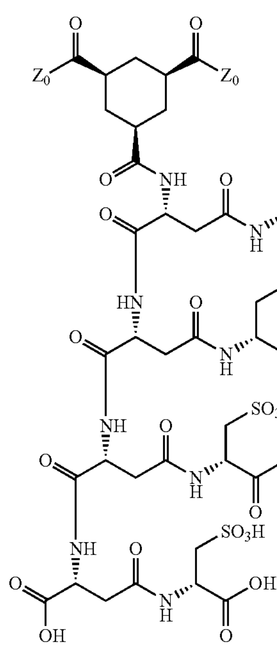 |

-continued

| Ref. No. | Abbreviated Ref. | Structure |
|---|---|---|
| MD352 Mol. Weight. 1994 | PK2 PYR($Z_n$)$_2$[D-Cya]$_7$COOH | 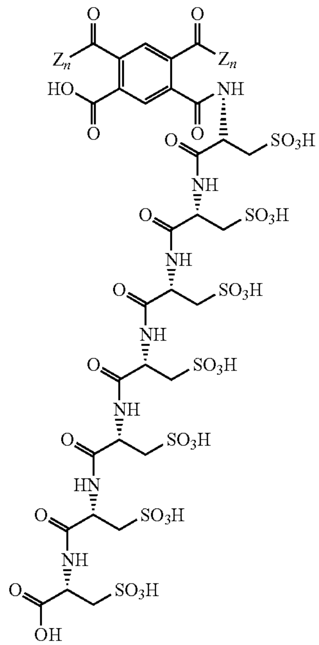 |
| MD356 Mol. Weight. 1940 | PK1 PYR($Z_n$)$_2$-[D-Cya-D-Cya]$_2$ | 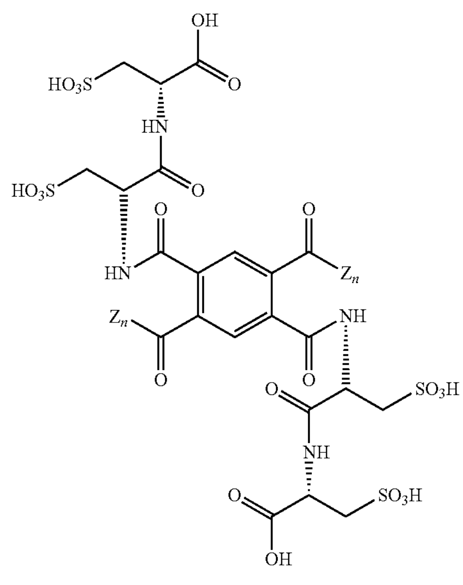 |
| MD357 Mol. Weight. 1854 | PK2 PYR($Z_n$)$_2$-D-Cya-D-Cya]$_2$ | 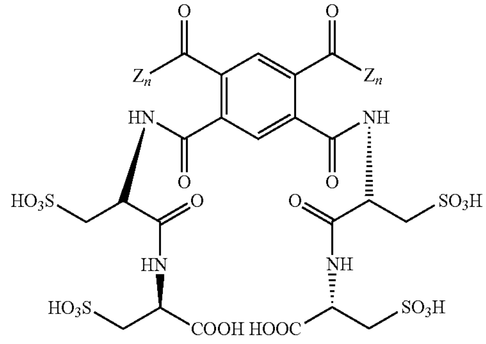 |

| Ref. No. | Abbreviated Ref. | Structure |
|---|---|---|
| MD358 Mol. Weight. 1940 | PK1 PYR($Z_n$)$_2$[L-Asp-L-Asp-L-Asp]$_2$ | 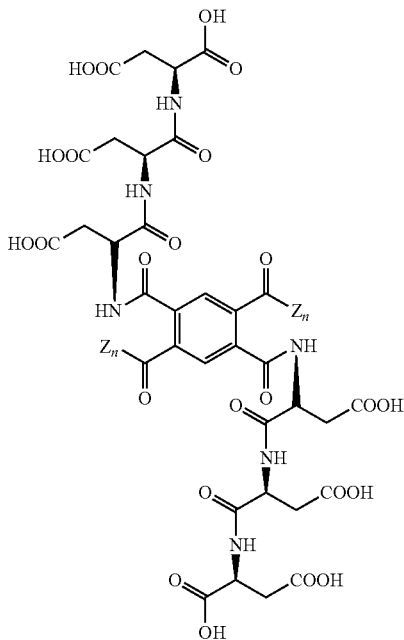 |
| MD359 Mol. Weight. 2158 | PK1 PYR($Z_n$)$_2$[(D-Cya)$_3$-OH]$_2$ | 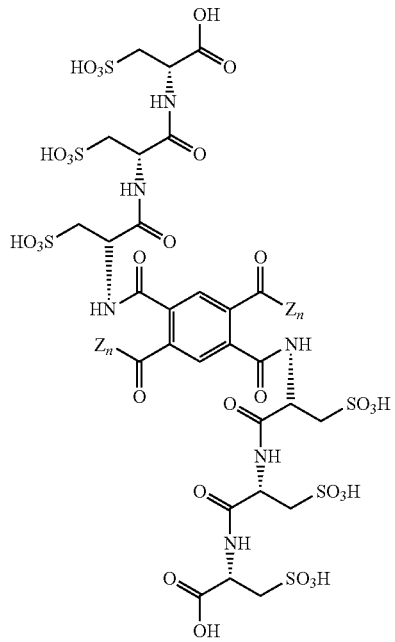 |

| Ref. No. | Abbreviated Ref. | Structure |
|---|---|---|
| MD371 Mol. Weight. 1710 | PK1 PYR($Z_n$)$_2$-[(D-Asp-D-Asp]$_2$ | 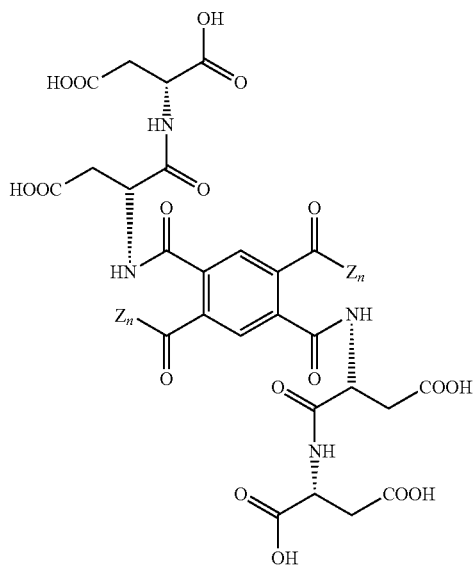 |
| MD373 Mol. Weight. 1940 | PK1 PYR($Z_n$)$_2$-[D-Asp-D-Asp-D-Asp]$_2$ | 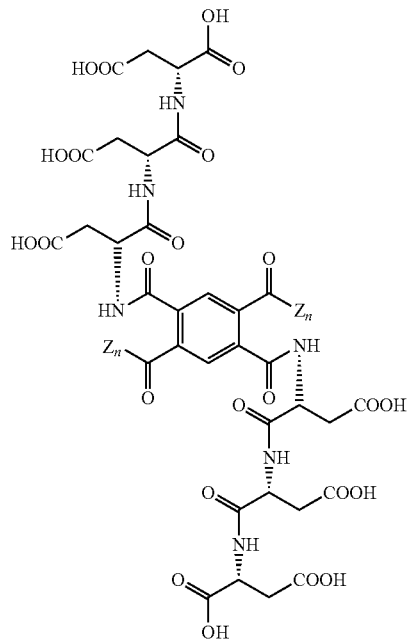 |

| Ref. No. | Abbreviated Ref. | Structure |
|---|---|---|
| MD376<br>Mol. Weight. 2170 | PK1 PYR($Z_n$)$_2$-[D-Asp-D-Asp-D-Asp-D-Asp]$_2$ | 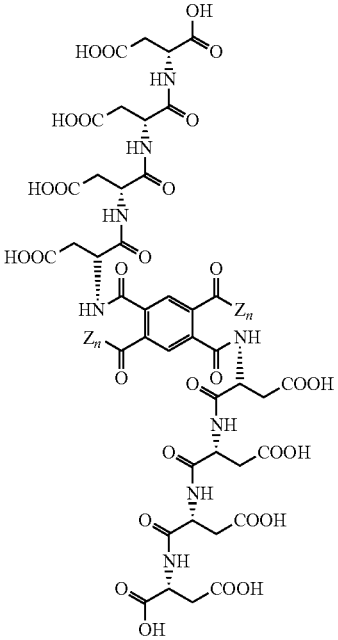 |

The term "alkyl" as used alone or in combination herein refers to a straight or branched chain saturated hydrocarbon group. The term "C1-12 alkyl" refers to such a group containing from one to twelve carbon atoms and "lower alkyl" refers to C1-6 alkyl groups containing from one to six carbon atoms, such as methyl ("Me"), ethyl ("Et"), n-propyl, isopropyl, n-butyl, isobutyl, sec-butyl, tert-butyl and the like.

The term "cycloalkyl" refers to non-aromatic, saturated non-aromatic carbocycles. The term "C4-9 cycloalkyl", for instance, refers to such a group having from 4 to 9 carbon atoms. Examples include cyclobutyl, cyclopentyl and cyclohexyl.

The term "alkenyl" refers to a straight or branched hydrocarbon containing one or more double bonds, preferably one or two double bonds. The term "C2-12 alkenyl", for instance, refers to such a group containing from two to twelve carbon atoms. Examples of alkenyl include allyl, 1-methylvinyl, butenyl, iso-butenyl, 1,3-butadienyl, 3-methyl-2-butenyl, 1,3-butadienyl, 1,4-pentadienyl, 1-pentenyl, 1-hexenyl, 3-hexenyl, 1,3-hexadienyl, 1,4-hexadienyl and 1,3,5-hexatrienyl.

The term "alkynyl" refers to a straight or branched hydrocarbon containing one or more triple bonds, preferably one or two triple bonds. The term "C2-12 alkynyl", for instance, refers to such a group containing from two to twelve carbon atoms. Examples include 2-propynyl and 2- or 3-butynyl.

The term "alkoxy" as used alone or in combination refers to a straight or branched chain alkyl group covalently bound via an oxygen linkage (—O—) and the terms "C1-6 alkoxy" and "lower alkoxy" refer to such groups containing from one to six carbon atoms, such as methoxy, ethoxy, propoxy, isopropoxy, butoxy, t-butoxy and the like.

The term "cycloalkenyl" refers to cyclic alkenyl groups having a single cyclic ring or multiple condensed rings, and at least one point of internal unsaturation, preferably incorporating 4 to 11 carbon atoms. Examples of suitable cycloalkenyl groups include, for instance, cyclobut-2-enyl, cyclopent-3-enyl, cyclohex-4-enyl, cyclooct-3-enyl, indenyl and the like.

The term "acyl" refers to groups H—C(O)—, alkyl-C(O)—, cycloalkyl-C(O)—, aryl-C(O)—, heteroaryl-C(O)— and heterocyclyl-C(O)—, where alkyl, cycloalkyl, aryl, heteroaryl and heterocyclyl are described herein.

The term "aryl" refers to carbocyclic (non-heterocyclic) aromatic rings or ring systems. The aromatic rings may be mono- or bi-cyclic ring systems. The aromatic rings or ring systems are generally composed of 5 to 10 carbon atoms. Examples of suitable aryl groups include but are not limited to phenyl, biphenyl, naphthyl, tetrahydronaphthyl, and the like.

The term "alkylene" refers to a saturated, branched or straight chain or cyclic hydrocarbon radical having two monovalent radical centers derived by the removal of two hydrogen atoms from the same or two different carbon atoms of a parent alkane. For example, an alkylene group can have 1 to 20 carbon atoms, 1 to 10 carbon atoms, or 1 to 6 carbon atoms. Typical alkylene radicals include, but are not limited to, methylene (—CH$_2$—), 1,1-ethyl (—CH(CH$_3$)—), 1,2-ethyl (—CH$_2$CH$_2$—), 1,1-propyl (—CH(CH$_2$CH$_3$)—), 1,2-propyl (—CH$_2$CH(CH$_3$)—), 1,3-propyl (—CH$_2$CH$_2$CH$_2$—), 1,4-butyl (—CH$_2$CH$_2$CH$_2$CH$_2$—), and the like.

The term "alkenylene" refers to an unsaturated, branched or straight chain or cyclic hydrocarbon radical having two monovalent radical centers derived by the removal of two hydrogen atoms from the same or two different carbon atoms of a parent alkene. For example, and alkenylene group can have 1 to 20 carbon atoms, 1 to 10 carbon atoms, or 1 to 6 carbon atoms. Typical alkenylene radicals include, but are not limited to, 1,2-ethylene (—CH═CH—).

The term "alkynylene" refers to an unsaturated, branched or straight chain or cyclic hydrocarbon radical having two monovalent radical centers derived by the removal of two hydrogen atoms from the same or two different carbon atoms of a parent alkyne. For example, an alkynylene group can have 1 to 20 carbon atoms, 1 to 10 carbon atoms, or 1 to 6 carbon atoms. Typical alkynylene radicals include, but are not limited to, acetylene (—C≡C—), propargyl (—CH$_2$C≡C—), and 4-pentynyl (—CH$_2$CH$_2$CH$_2$C≡CH—).

The term "arylene" refers to an aryl radical having two monovalent radical centres derived from the removal of two hydrogen atoms from the same or two different carbon or heteroatoms of a parent aryl group.

The terms "halo" and "halogen" refers to fluoro, chloro, bromo and iodo groups.

The term "halo alkyl" group has one or more of the hydrogen atoms on an alkyl group replaced with halogens.

The term "heteroaryl" refers to a monovalent aromatic carbocyclic group, preferably of from 2 to 10 carbon atoms and 1 to 4 heteroatoms selected from oxygen, nitrogen and sulfur within the ring. Preferably the heteroatom is nitrogen. Such heteroaryl groups can have a single ring (e.g., pyridyl, pyrrolyl or furyl) or multiple condensed rings (e.g., indolizinyl, benzothienyl, or benzofuranyl).

The term "heterocyclyl" refers to a monovalent saturated or unsaturated group having a single ring or multiple condensed rings, preferably from 1 to 8 carbon atoms and from 1 to 4 hetero atoms selected from nitrogen, sulfur, oxygen, selenium or phosphorous within the ring.

The term "optionally substituted" means that a group may include one or more substituents. One or more hydrogen atoms on the group may be replaced by substituent groups independently selected from halogens (for example halo alkyl such as —CF$_3$ or —CF$_2$H), C$_{1-6}$alkyl, C$_{2-6}$alkenyl, C$_{2-6}$alkynyl, —(CH$_2$)$_v$C$_{3-7}$cycloalkyl, —(CH$_2$)$_v$C$_{4-7}$cycloalkenyl, —(CH$_2$)$_v$aryl, —(CH$_2$)$_v$heterocyclyl, —(CH$_2$)$_v$heteroaryl, —C$_6$H$_4$S(O)$_q$C$_{1-6}$alkyl, —C(Ph)$_3$, —CN, —OR, —O—(CH$_2$)$_{1-6}$—R, —O—(CH$_2$)$_{1-6}$—OR, —OC(O)R, —C(O)R, —C(O)OR, —OC(O)NR'R'', —NR'R'', —NO$_2$, —NRC(O)R', —NRC(O)NR'R'', —NRC(S)NR'R'', —NRS(O)$_2$R', —NRC(O)OR', —C(NR)NR'R'', —C(=NOR')R, —C(=NOH)NR'R'', —C(O)NR'R'', —C(=NCN)—NR'R'', —C(=NR)NR'R'', —C(=NR')SR'', —NR'C(=NCN)SR'', —CONR$_2$R', —C(S)NR'R'', —S(O)$_q$R, —SO$_2$NR'R'', —SO$_2$NRC(O)R', —OS(O)$_2$R, —PO(OR)$_2$ and —NO$_2$; where v is 0-6, q is 0-2 and each R, R' and R'' is independently selected from H, C$_{1-6}$alkyl, C$_{2-6}$alkenyl, C$_{2-6}$alkynyl, C$_{3-7}$-cycloalkyl, C$_{4-7}$cycloalkenyl, aryl, heterocyclyl, heteroaryl, C$_{1-6}$alkylaryl, C$_{1-6}$alkylheteroaryl, and C$_{1-6}$alkylheterocyclyl, wherein the alkyl, alkenyl, alkynyl, cycloalkyl, cycloalkenyl, aryl, heterocyclyl, heteroaryl, C$_{1-6}$alkylaryl, C$_{1-6}$alkylheteroaryl, or C$_{1-6}$alkylheterocyclyl, may be optionally substituted with one to six of same or different groups selected from halogen, hydroxy, lower alkyl, lower alkoxy, —CO$_2$H, CF$_3$, CN, phenyl, NH$_2$ and —NO$_2$; or when R' and R'' are attached to the same nitrogen atom, they may, together with the atom to which they are attached, form a 5 to 7 membered nitrogen containing heterocyclic ring.

In the lists of possible functional groups defined herein, where a given group contains two or more subgroups, for example the subgroups may be listed in the format [subgroup A][subgroup B] as in alkylaryl, or [subgroup A][subgroup B][subgroup C] as in aryloxyalkyl, the order of the subgroups as they are listed above is not intended to be limited to the order in which they are presented. Thus, a group with two subgroups defined as [subgroup A][subgroup B], such as alkylaryl, is intended to also be a reference to a group with two subgroups defined as [subgroup B][subgroup A], such as arylalkyl.

The term "chiral" refers to molecules which have the property of non-superimposability of the mirror image partner, while the term "achiral" refers to molecules which are superimposable on their mirror image partner.

The term "stereoisomers" refers to compounds which have identical chemical constitution, but differ with regard to the arrangement of the atoms or groups in space.

The term "diastereomer" refers to a stereoisomer with two or more centers of chirality and whose molecules are not mirror images of one another. Diastereomers have different physical properties, e.g., melting points, boiling points, spectral properties, and reactivities. Mixtures of diastereomers may separate under high resolution analytical procedures such as electrophoresis and chromatography.

The term "enantiomers" refer to two stereoisomers of a compound which are non-superimposable mirror images of one another.

Stereochemical definitions and conventions used herein generally follow S. P. Parker, Ed., McGraw-Hill Dictionary of Chemical Terms (1984) McGraw-Hill Book Company, New York; and Eliel, E. and Wilen, S., Stereochemistry of Organic Compounds (1994) John Wiley & Sons, Inc., New York. Many organic compounds exist in optically active forms, i.e., they have the ability to rotate the plane of plane-polarized light. In describing an optically active compound, the prefixes D and L or R and S are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. For a given chemical structure, these stereoisomers are identical except that they are mirror images of one another. A specific stereoisomer may also be referred to as an enantiomer, and a mixture of such isomers is often called an enantiomeric mixture. A 50:50 mixture of enantiomers is referred to as a racemic mixture or a racemate, which may occur where there has been no stereoselection or stereospecificity in a chemical reaction or process. The terms "racemic mixture" and "racemate" refer to an equimolar mixture of two enantiomeric species, devoid of optical activity.

As used herein, amino acids and derivatives thereof may be abbreviated to their respective three letter or single letter codes as appropriate. For example, cysteic acid may be referred to herein as Cya, Cyst or Cyst-SO$_3$H, aspartic acid may be referred to as Asp.

The salts of the compounds of the invention are preferably pharmaceutically acceptable, but it will be appreciated that non-pharmaceutically acceptable salts also fall within the scope of the present invention, since these are useful as intermediates in the preparation of pharmaceutically acceptable salts.

It will be appreciated that the compounds of the invention, and the salts thereof, can be presented in the form of pharmaceutically acceptable derivatives. The term "pharmaceutically acceptable derivative" includes pharmaceutically acceptable esters, prodrugs, solvates and hydrates of the compounds of Formula (I), or salts thereof. Pharmaceutically acceptable derivatives may include any pharmaceutically acceptable hydrate or any other compound or prodrug which, upon administration to a subject, is capable of providing (directly or indirectly) a compound of the invention, or an active metabolite or residue thereof.

The pharmaceutically acceptable salts include acid addition salts, base addition salts, and the salts of quaternary amines and pyridiniums. The acid addition salts are formed from a compound of the invention and a pharmaceutically acceptable inorganic or organic acid including but not limited to hydrochloric, hydrobromic, sulfuric, phosphoric, methanesulfonic, toluenesulphonic, benzenesulphonic, acetic, propionic, ascorbic, citric, malonic, fumaric, maleic, lactic, salicylic, sulfamic, tartaric or amino acids. The counter ion of quaternary amines and pyridiniums include chloride, bromide, iodide, sulfate, phosphate, methanesulfonate, citrate, acetate, malonate, fumarate, sulfamate, and tartrate. The base addition salts include but are not limited to salts such as sodium, potassium, calcium, lithium, magnesium, ammonium and alkylammonium. Also, basic nitrogen-containing groups may be quaternised with such agents as lower alkyl halides, such as methyl, ethyl, propyl, and butyl chlorides, bromides and iodides; dialkyl sulfates like dimethyl and diethyl sulfate; and others. The salts may be made in a known manner, for example by treating the compound with an appropriate acid or base in the presence of a suitable solvent.

The compounds of the invention may be in crystalline form and/or as solvates (e.g. hydrates) and it is intended that both forms be within the scope of the present invention. The term "solvate" is a complex of variable stoichiometry formed by a solute (in this invention, a compound of the invention) and a solvent. Such solvents should not interfere with the biological activity of the solute. Solvents may be, by way of example, water, ethanol or acetic acid. Methods of solvation are generally known within the art.

The term "pro-drug" is used in its broadest sense and encompasses those derivatives that are converted in vivo to the compounds of the invention. Such derivatives would readily occur to those skilled in the art, and include, for example, compounds where a free hydroxy group is converted into an ester derivative or a ring nitrogen atom is converted to an N-oxide. Examples of ester derivatives include alkyl esters, phosphate esters and those formed from amino acids, preferably valine. Any compound that is a prodrug of a compound of the invention is within the scope and spirit of the invention.

The term "pharmaceutically acceptable ester" includes biologically acceptable esters of compound of the invention such as sulphonic, phosphonic and carboxylic acid derivatives.

Thus, in another aspect of the invention, there is provided a prodrug or pharmaceutically acceptable ester of a compound of the invention or of salt thereof.

It will be appreciated that the compounds of the invention have at least one asymmetric centre, and therefore are capable of existing in more than one stereoisomeric form. The invention extends to each of these forms individually and to mixtures thereof, including racemates. The isomers may be separated conventionally by chromatographic methods or using a resolving agent. Alternatively the individual isomers may be prepared by asymmetric synthesis using chiral intermediates. Where the compound has at least one carbon-carbon double bond, it may occur in Z- and E-forms with all isomeric forms of the compounds being included in the present invention.

The invention also includes where possible a salt or pharmaceutically acceptable derivative such as a pharmaceutically acceptable ester, solvate and/or prodrug of the above mentioned embodiments of the invention.

In another aspect of the invention, there is provided a pharmaceutical composition that comprises a therapeutically effective amount of one or more of the aforementioned compounds or pharmaceutically acceptable salts thereof, including pharmaceutically acceptable derivatives thereof, and optionally a pharmaceutically acceptable carrier or diluent.

In another aspect, the present invention provides pharmaceutical compositions for use in the treatment or prevention of influenza viral infection, the composition comprising an effective amount of a compound of the invention, or a pharmaceutically acceptable salt thereof, including a pharmaceutically acceptable derivative thereof, and optionally a pharmaceutically acceptable carrier or diluent.

The term "composition" is intended to include the formulation of an active ingredient with encapsulating material as carrier, to give a capsule in which the active ingredient (with or without other carrier) is surrounded by carriers.

The pharmaceutical compositions or formulations include those suitable for oral, rectal, nasal, topical (including buccal and sub-lingual), vaginal or parenteral (including intramuscular, sub-cutaneous and intravenous) administration or in a form suitable for administration by inhalation or insufflation. In one embodiment, the compounds of the invention are formulated for inhalation, oral administration, intranasal administration, intraperitoneal administration, intravenous administration or intramuscular administration.

General considerations in formulation and/or manufacture of pharmaceutical compositions agents can be found, for example, in *Remington's Pharmaceutical Sciences,* Sixteenth Edition. E. W. Martin (Mack Publishing Co., Easton, Pa., 1980), and *Remington: The Science and Practice of Pharmacy,* 21st Edition (Lippincott Williams & Wilkins, 2005).

In one embodiment, the compositions and formulations in accordance with the invention may be administered to a person in need thereof by any suitable inhalation, insufflation or intranasal delivery method. Suitable methods for inhalation, insufflation or intranasal administration would be well-known to a person skilled in the art.

In one embodiment, the compositions or formulations of compounds of the invention may be in a form suitable for administration by inhalation or insufflation. For example, the compositions or formulations of compounds of the invention may be prepared as a dry powder, solution, suspension or aerosol for inhalation or insufflation via the mouth or nose. Formulations suitable for aerosol or dry powder administration may be prepared according to conventional methods and may be delivered with other therapeutic agents such as compounds heretofore used in the treatment or prophylaxis of infections as described herein.

In one embodiment, the compositions or formulation of compounds of the invention may be administered by means of a dry powder inhaler. Dry powder inhalers of types readily disclosed in the art may be used, as well as micronized shavings of isostatically compressed tablets or discs of drug with or without inert binders such as lactose may be used. This method of administration provides particularly rapid delivery to the lung. When the compound of the invention is provided in the form of a dry powder, it may be presented alone or in admixture with a suitable pharmaceutically acceptable diluent such as starch, starch derivatives such as hydroxypropylmethyl cellulose or polyvinylpyrrolidine (PVP), sugar derivatives such as mannitol or lactose. The powder composition may be presented in unit dose form, for example in capsules or cartridges of e.g. gelatin or formed plastic or blister packs from which the powder may be administered by means of an inhalation device, or in multidose form from, for example, a powder reservoir.

For inhalation of droplets, mists and aerosols various devices such as nebulizers or pressurized aerosol generators are readily available. In addition, such devices can be metered to provide uniformity of dosing.

All inhalers may be designed and fashioned to deliver liquid or solid particles to the nasal mucosa as well as the upper and/or lower airways.

In another embodiment, the compositions or formulation of compounds of the invention may be administered by inhalation or insufflation by means of a wet aerosol inhaler. For example, the compositions or formulation of compounds of the invention may be prepared for administration by wet aerosol inhalation in a pre-metered inhaler.

In a further embodiment, the compositions or formulations of compounds of the invention are in a form suitable for administration intranasally. The intranasal compositions disclosed herein can be administered as a spray or drop. Accordingly, suitable commercial packages containing the intranasal formulation can be in any spray container known in the art. In one or more embodiments, the formulations in accordance with the invention may be administered via a spray device or container. Spray devices in accordance with the invention may be single unit dose systems or multiple dose systems, for example comprising a bottle, a pump and/or an actuator. Such spray devices are available commercially. Suitable commercial spray devices include those available from Nemera, Aptar, Bespak and Becton-Dickinson. Other suitable means for administering the compositions or formulations intranasally in accordance with the invention include via a dropper, a syringe, a squeeze bottle, and any other means known in the art for applying liquids to the nasal mucosa in an accurate and repeatable fashion.

The compounds of the present invention can also be administered in a wide variety of oral and parenteral dosage forms. It will be obvious to those skilled in the art that the following dosage forms may comprise, as the active component, either a compound of the invention or a pharmaceutically acceptable salt of a compound of the invention.

The compositions or formulations of compounds of the invention may be in the form of a sterile injectable preparation, such as a sterile injectable aqueous or oleaginous suspension. This suspension may be formulated according to the known art using those suitable dispersing or wetting agents and suspending agents which have been mentioned herein. The sterile injectable preparation may also be a sterile injectable solution or suspension in a non-toxic parenterally acceptable diluent or solvent, such as a solution in 1,3-butane-diol or prepared as a lyophilized powder. Among the acceptable vehicles and solvents that may be employed are water, Ringer's solution and isotonic sodium chloride solution. In addition, sterile fixed oils may conventionally be employed as a solvent or suspending medium. For this purpose any bland fixed oil may be employed including synthetic mono- or diglycerides. In addition, fatty acids such as oleic acid may likewise be used in the preparation of injectables. Furthermore, formulations suitable for parenteral administration include aqueous and non-aqueous sterile injection solutions which may contain antioxidants, buffers, bacteriostats and solutes which render the formulation isotonic with the blood of the intended recipient; and aqueous and non-aqueous sterile suspensions which may include suspending agents and thickening agents.

The compositions or formulations of compounds of the invention may also be administered orally, for example, tablets, troches, lozenges, aqueous or oil suspensions, dispersible powders or granules, emulsions, hard or soft capsules, syrups or elixirs may be prepared. Compositions intended for oral use may be prepared according to any method known to the art for the manufacture of pharmaceutical compositions and such compositions may contain one or more agents including sweetening agents, flavouring agents, colouring agents and preserving agents, in order to provide a palatable preparation.

The compounds of the invention, together with a conventional adjuvant, carrier, or diluent, may be placed into the form of pharmaceutical compositions and unit dosages thereof, and in such form may be employed as solids, such as tablets or filled capsules, or liquids such as solutions, suspensions, emulsions, elixirs, or capsules filled with the same, all for oral use, in the form of suppositories for rectal administration; or in the form of sterile injectable solutions for parenteral (including subcutaneous) use.

Such pharmaceutical compositions and unit dosage forms thereof may comprise conventional ingredients in conventional proportions, with or without additional active compounds or principles, and such unit dosage forms may contain any suitable effective amount of the active ingredient commensurate with the intended daily dosage range to be employed. Formulations containing ten (10) milligrams of active ingredient or, more broadly, 0.1 to one hundred (100) milligrams, per tablet, are accordingly suitable representative unit dosage forms.

For preparing pharmaceutical compositions from the compounds of the present invention, pharmaceutically acceptable carriers can be either solid or liquid. Solid form preparations include powders, tablets, pills, capsules, cachets, suppositories, and dispensable granules. A solid carrier can be one or more substances which may also act as diluents, flavouring agents, solubilisers, lubricants, suspending agents, binders, preservatives, tablet disintegrating agents, or an encapsulating material.

In powders, the carrier is a finely divided solid that is in a mixture with the finely divided active component.

In tablets, the active component is mixed with the carrier having the necessary binding capacity in suitable proportions and compacted in the shape and size desired.

The powders and tablets preferably contain from five or ten to about seventy percent of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as carrier providing a capsule in which the active component, with or without carriers, is surrounded by a carrier, which is thus in association with it. Similarly, cachets and lozenges are included. Tablets, powders, capsules, pills, cachets, and lozenges can be used as solid forms suitable for oral administration.

For preparing suppositories, a low melting wax, such as an admixture of fatty acid glycerides or cocoa butter, is first melted and the active component is dispersed homogeneously therein, as by stirring. The molten homogenous mixture is then poured into convenient sized moulds, allowed to cool, and thereby to solidify.

Formulations suitable for vaginal administration may be presented as pessaries, tampons, creams, gels, pastes, foams or sprays containing in addition to the active ingredient such carriers as are known in the art to be appropriate.

Liquid form preparations include solutions, suspensions, and emulsions, for example, water or water-propylene glycol solutions. For example, parenteral injection liquid preparations can be formulated as solutions in aqueous polyethylene glycol solution.

Sterile liquid form compositions include sterile solutions, suspensions, emulsions, syrups and elixirs. The active ingredient can be dissolved or suspended in a pharmaceutically acceptable carrier, such as sterile water, sterile organic solvent or a mixture of both.

The compounds according to the present invention may thus be formulated for parenteral administration (e.g. by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, and may contain formulation agents such as suspending, stabilising and/or dispersing agents. Alternatively, the active ingredient may be in powder form, obtained by aseptic isolation of sterile solid or by lyophilisation from solution, for constitution with a suitable vehicle, e.g. sterile, pyrogen-free water, before use.

Aqueous solutions suitable for oral use can be prepared by dissolving the active component in water and adding suitable colorants, flavours, stabilising and thickening agents, as desired.

Aqueous suspensions suitable for oral use can be made by dispersing the finely divided active component in water with viscous material, such as natural or synthetic gums, resins, methylcellulose, sodium carboxymethylcellulose, or other well known suspending agents.

Also included are solid form preparations that are intended to be converted, shortly before use, to liquid form preparations for oral administration. Such liquid forms include solutions, suspensions, and emulsions. These preparations may contain, in addition to the active component, colorants, flavours, stabilisers, buffers, artificial and natural sweeteners, dispersants, thickeners, solubilising agents, and the like.

For topical administration to the epidermis the compounds according to the invention may be formulated as ointments, creams or lotions, or as a transdermal patch. Ointments and creams may, for example, be formulated with an aqueous or oily base with the addition of suitable thickening and/or gelling agents. Lotions may be formulated with an aqueous or oily base and will in general also contain one or more emulsifying agents, stabilising agents, dispersing agents, suspending agents, thickening agents, or colouring agents.

Formulations suitable for topical administration in the mouth include lozenges comprising active agent in a flavoured base, usually sucrose and acacia or tragacanth; pastilles comprising the active ingredient in an inert base such as gelatin and glycerin or sucrose and acacia; and mouthwashes comprising the active ingredient in a suitable liquid carrier.

Solutions or suspensions are applied directly to the nasal cavity by conventional means, for example with a dropper, pipette or spray. The formulations may be provided in single or multidose form. In the latter case of a dropper or pipette, this may be achieved by the patient administering an appropriate, predetermined volume of the solution or suspension. In the case of a spray, this may be achieved for example by means of a metering atomising spray pump. To improve nasal delivery and retention the compounds according to the invention may be encapsulated with cyclodextrins, or formulated with other agents expected to enhance delivery and retention in the nasal mucosa.

Administration to the respiratory tract may also be achieved by means of an aerosol formulation in which the active ingredient is provided in a pressurised pack with a suitable propellant such as a hydrofluoroalkane (HFA) or a chlorofluorocarbon (CFC) for example dichlorodifluoromethane, trichlorofluoromethane, or dichlorotetrafluoroethane, carbon dioxide, or other suitable gas. The aerosol may conveniently also contain a surfactant such as lecithin. The dose of drug may be controlled by provision of a metered valve.

Alternatively the active ingredients may be provided in the form of a dry powder, for example a powder mix of the compound in a suitable powder base such as lactose, starch, starch derivatives such as hydroxypropylmethyl cellulose and polyvinylpyrrolidone (PVP). Conveniently the powder carrier will form a gel in the nasal cavity. The powder composition may be presented in unit dose form for example in capsules or cartridges of, e.g., gelatin, or blister packs from which the powder may be administered by means of an inhaler.

In formulations intended for administration to the respiratory tract, including intranasal formulations, the compound will generally have a small particle size for example of the order of 5 to 10 microns or less. Such a particle size may be obtained by means known in the art, for example by micronisation.

When desired, formulations adapted to give sustained release of the active ingredient may be employed.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The invention also includes the compounds in the absence of carrier where the compounds are in unit dosage form.

The amount of the compound of the invention to be administered may be in the range from about 0.01 mg to 2000 mg per day, depending on the activity of the compound and the disease to be treated.

The amount of the compound required for use in treatment will vary with the route of administration, the nature of the condition being treated and the age and condition of the animal (including human patients), and will ultimately be at the discretion of the attendant veterinarian or physician.

For example, a suitable dose will be in the range of from about 0.1 mg to 100 mg/kg of body weight per day, preferably in the range of 0.1 mg to 50 mg/kg/day.

In some embodiments, the dosage for oral administration would be in the range 1 mg/kg/day to 100 mg/kg/day. The dose for injection would be in the range of 1 mg/kg/day to 100 mg/kg/day. The dose for inhalation would be in the range of 0.01 mg/kg/day to 1 mg/kg/day. In some preferred embodiments, the dose would be in the range of 5 mg-50 mg/kg for oral or injection administration two to three times a day for a period of 1 to 15 days, preferably 3 to 12 days, more preferably 5 to 10 days. In other preferred embodiments, the dose would be in the range of 0.1-0.5 mg/kg for inhalation one to five times a day a period of 1 to 15 days, preferably 3 to 12 days, more preferably for period of 5 to 10 days. Alternatively, in other preferred embodiment, the dose would be in the range of 0.2 mg/kg-0.4 mg/kg for inhalation as a single daily administration for the duration of treatment. It is understood that the desired dose may be administered in a single dose or as divided dose administered at appropriate intervals, for example as two, three, four or more sub-doses per day.

The compounds of the invention are conveniently administered in unit dosage form, for example containing 0.1 to 10 mg of active ingredient per unit dosage form.

While it is possible that, for use in therapy, the compounds may be administered as the raw chemical, it is preferable to present the active ingredient as a pharmaceutical formulation. The invention thus further provides a pharmaceutical formulation including the compounds together with one or more pharmaceutically acceptable carriers thereof and, optionally, other therapeutic and/or prophylactic ingredients. The carrier(s) must be 'acceptable' in the sense of being compatible with the other ingredients of the formulation and not deleterious to the recipient thereof.

Pharmaceutical formulations include those suitable for oral, rectal, nasal, or parenteral (including intramuscular, intradermal, sub-cutaneous and intravenous) administration or in a form suitable for administration to the gastrointestinal tract, or in a form suitable to the respiratory tract (including the nasal passages) for example by inhalation or insufflation or for intradermal or sub-cutaneous implantation or for transdermal patch. The formulations may, where appropriate, be conveniently presented in discrete dosage units and may be prepared by any of the methods well known in the art. All methods include the step of bringing into association the active compound with a carrier, such as a liquid carrier or finely divided solid carrier or combinations thereof, and then, if necessary, shaping the product into the desired formulation.

Liquids or powders for intranasal administration, tablets or capsules for oral administration and liquids for intravenous administration are the preferred compositions.

The pharmaceutical preparations of the compounds according to the present invention may be co-administered with one or more other active agents in combination therapy. For example the pharmaceutical preparation of the active compound may be co-administered (for example, separately, concurrently or sequentially), with one or more other antiviral agents, antibiotics, and anti-inflammatory drugs.

The term "therapeutically effective amount" refers to that amount which is sufficient to effect treatment, as defined above, when administered to a subject, such as a mammal, including a human in need of such treatment. The therapeutically effective amount will vary depending on the subject and disease state being treated, the severity of the affliction and the manner of administration, and may be determined routinely by one of ordinary skill in the art.

The term "treatment" as used herein covers any treatment of a disease or illness in an animal, preferably a mammal, more preferably a human, and includes: (i) preventing the disease or condition from occurring in a subject, (ii) inhibiting the disease or condition, (iii) relieving the disease or condition, or (iv) relieving the conditions/symptoms caused by the disease.

The terms "preventing" and "prophylaxis" as used herein refer to administering a medicament beforehand to avert or forestall the appearance of one or more symptoms of a disease or disorder. The person of ordinary skill in the medical art recognizes that the term "prevent" is not an absolute term. In the medical art it is understood to refer to the prophylactic administration of a drug to substantially diminish the likelihood or seriousness of a condition, or symptom of the condition and this is the sense intended in this disclosure. As used in a standard text in the field, the Physician's Desk Reference, the terms "prevent", "preventing" and "prevention" with regard to a disorder or disease, refer to averting the cause, effects, symptoms or progression of a disease or disorder prior to the disease or disorder fully manifesting itself.

The terms "administer", "administering" or "administration" in reference to a compound, composition or formulation of the invention means introducing the compound into the system of the animal in need of treatment. When a compound of the invention is provided in combination with one or more other active agents, "administration" and its variants are each understood to include concurrent and/or sequential introduction of the compound and the other active agents.

EXAMPLES

Aspects disclosed herein are further described by the following non-limiting examples.

General Methods and Notes

Unless otherwise noted, NMR spectra were recorded on Bruker Avance 300. Xwin-NMR version 3.5 on DPX 300A.

Unless otherwise noted, mass spectra were recorded on Mass Spectrometer Waters Micromass ZMD using an ESI (electrospray ionisation probe), using Water Mass Lynx NT software.

Unless otherwise noted, flash column chromatography was performed on silica gel 60 F245 (E. Merck).

Thin Layer Chromatography (TLC) was performed on silica gel pre-coated plates (E. Merck).

Unless otherwise noted, high-performance liquid chromatography (HPLC) were performed on a Waters Alliance 2690 separation module, using a Waters dual wavelength 2487 UV detector and Waters Millennium 32 software.

General Procedure for Regulation of Laboratory Animals

Ethics regulation of relevant experiments utilising laboratory animals was conducted in accordance with the approval of the Institutional Animal Care and Use Committee of the corresponding Institutions/Universities.

General Procedure for Plaque Reduction Assay

MDCK cells were seeded into six-well tissue culture plates and grown to confluence by standard methods. Influenza viruses were diluted in a minimal volume of phosphate-buffered saline (PBS) supplemented with 0.2% BSA to yield an estimated titre of 50 to 100 PFU per well. After absorption onto the MDCK cells for 1 h at 37° C. in a 5% $CO_2$ atmosphere, the viral inocula were aspirated and replaced with viral growth medium (minimal Eagle's medium supplemented with BSA, trypsin, and insulin-transferrin-selenium) containing agar or agarose at an amount (generally 1 to 2%) sufficient to cause the medium to gel at room temperature. The plates were incubated at 37° C. in a $CO_2$ atmosphere until plaques developed (generally 2 to 4 days). The plaques were visualized with a suitable stain (e.g., 0.4% crystal violet in formal saline) before they were counted. Antiviral potency ($EC_{50}$) was determined as the concentration of the compound in the medium that reduced the plaque numbers to 50% of the value for the untreated control.

Materials and General Procedure for CPE Assay

Test compounds were dissolved in sterile water and stored at −20° C. Compounds were subsequently diluted in assay media (MEM+trypsin) to desired concentrations.

The assay media comprised Gibco 1 MEM (500 mL) supplemented with 1 mM MEM non-essential amino acids, 50 U-penicillin 50 µg/mL streptomycin, 1 mM sodium pyruvate. Trypsin (TPCK-treated) was added to the media to a final concentration of 1 µg/ml, prior to the assay being conducted.

MDCK cells (ATCC) were grown in growth media-Gibco 1×MEM (500 mL) supplemented with 1 mM MEM non-essential amino acids, 50 U-penicillin-50 μg/mL streptomycin, 1 mM sodium pyruvate, and 10% FBS.

Viral stock was diluted in PBS.

The assay was conducted using a CellTitre 96 Aqueous One Solution Cell Proliferation Assay (Promega).

Unless otherwise noted, the following general method was utilised for CPE assays:
  i) MDCK cells were grown to confluency in 96 well trays in growth media;
  ii) Media was removed;
  iii) 46 μL of diluted virus was added per well, including to mock infected wells;
  iv) Plates were incubated at 37° C. for 1.5 h. During this time, test compounds were prepared.
  v) After 1.5 h, the viral inoculum was removed.
  vi) Compounds to be tested were prepared, by perform 1:3 serial dilution of compounds on the abovementioned plates:
   a) 100 μL of assay media was added into Rows 3 to 11;
   b) 150 μL of compounds was added to Row 2;
   c) Titration of 50 μL from Row 2 to 10, then 50 μL was discarded from Row 10.
   d) Row 11 served as positive and negative control.
  vii) Cells were incubated at 37° C. for 48 h-96 h.
  viii) 48 h-96 h post infection, the media was removed.
  ix) Media was replaced with 100 μL of assay media without trypsin.
  x) 20 μL per well of detection solution was added.
  xi) Plates were incubated at 37° C. for a further 1 h.
  xii) Absorbance of the plates was measure of 490 nm.

Example 1: Pre-Treatment of Virus with Test Compounds Prior to Infection of MDCK Cells Representative compounds of Formula (I) were utilised to assess anti-viral activity prior to infection of MDCK cells. MD345 [(PK2 TCA($Z_0$)$_2$-[D-Cya-SO$_3$H]$_7$—OH], MD345 [(PK2 TCA($Z_0$)$_2$-[Cya]$_7$-OH], MD348 [(CHTCA($Z_0$)$_2$-D-Asp-(D-Cya)-D-Asp-(D-Cya)-D-Asp-(D-Cya)-OH] and MD348 [(CHTCA($Z_0$)$_2$-D-Asp-(D-Cya-SO$_3$H)-D-Asp-(D-Cya-SO$_3$H)-D-Asp-(D-Cya-SO$_3$H)—OH] were tested as representative compounds of Formula (I). Activity against two viral strains were tested, A/Sydney/250/99 (H1N1), and A/Sydney/5/97 (H3N2). Zanamivir was utilised as a control.

Conditions are detailed in Table 1 and a summary provided in FIG. 1.

TABLE 1

| Summary of conditions for pre treatment of virus prior to infection of MDCK cells | |
|---|---|
| Condition 1 | Virus in PBS pre-adsorbed on MDCK cells at 37° C. for 1 hr, virus suspension removed, then cells were washed with PBS (x 1), added assay media, and incubated at 37° C. for 72 hrs, tested by MTT colorimetric assay system. |
| Condition 2 | Virus were treated with PBS at R.T. for 60 min, then preadsorbed on MDCK cells at 37° C. for 1 hr. virus suspension removed. The cells were washed with PBS (x 1), assay media added, and incubated at 37° C. for 72 hrs, tested by MTT colorimetric assay system. |
| Condition 3 | Virus were treated with Trypsin (11 tg/ml) at R.T. for 60 min, then preadsorbed on MDCK cells at 37° C. for 1 hr, virus suspension removed, afterwards cells were washed with PBS (x 1), assay media added, and incubated at 37° C. for 72 hrs, tested by MTT colorimetric assay system. |
| Condition 4 | Virus were treated with Trypsin (1 μg/ml) at R.T. for 30 min, then mixed with compound at R.T. for 30 min, afterwards preadsobed on MDCK cells at 37° C. for 1 hr. virus suspension removed. The cells were washed with PBS (x, 1), assay media added, and incubated at 37° C. for 72 hrs, tested by MTT colorimetric assay system. |
| Condition 5 | Virus were treated with compound at R.T. for 30 min, then mixed with Trypsin (1 μg/ml) at RT. for 30 min, afterwards preadsobed on MDCK cells at 37° C. for 1 hr. virus suspension removed. The cells were washed with PBS (x 1), assay media added, and incubated at 37° C. for 72 hrs, tested by MTT colorimetric assay system. |
| Condition 6 | Virus, compound and Trypsin (1 μg/ml) were mixed at R.T. for 1 hr, then preadsorbed on MDCK cells at 37° C. for 1 hr. virus suspension removed. The cells were washed with PBS (x 1), assay media added, and incubated at 37° C. for 72 hrs, tested by MTT colorimetric assay system. |
| Condition 7 | Virus mixed with compound at R.T. for 1 hr, then preadsobed on MDCK cells at 37° C. for 1 hr, virus suspension removed. The cells were washed with PBS (x 1), assay media added, and incubated at 37° C. for 72 hrs, tested by MTT colorimetric assay system. |

Figure 2:
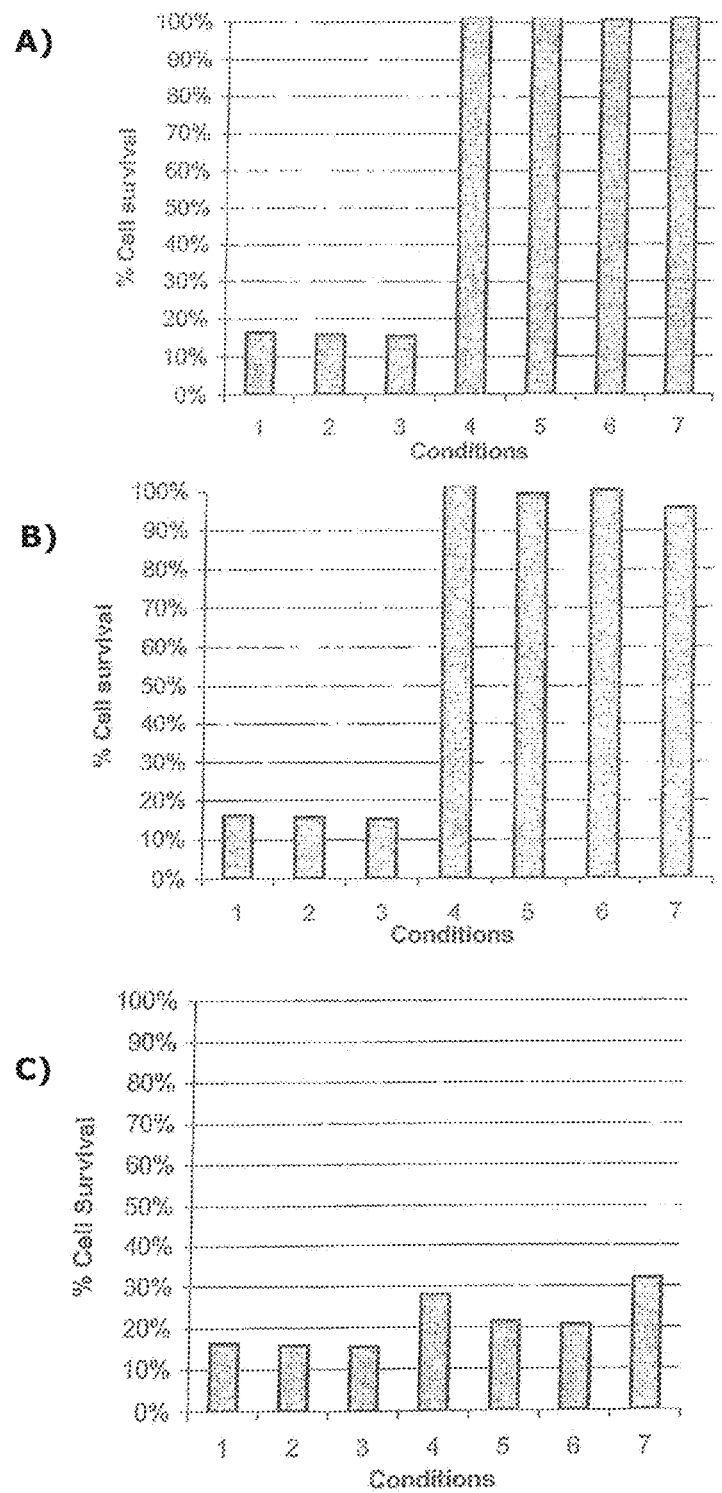
FIG. 2: Pre-treatment of virus (A/Sydney/250/99) with test compounds prior to infection of MDCK cells, A) MD348, B) MD345, and C) Zanamivir (control).
Figure 3:
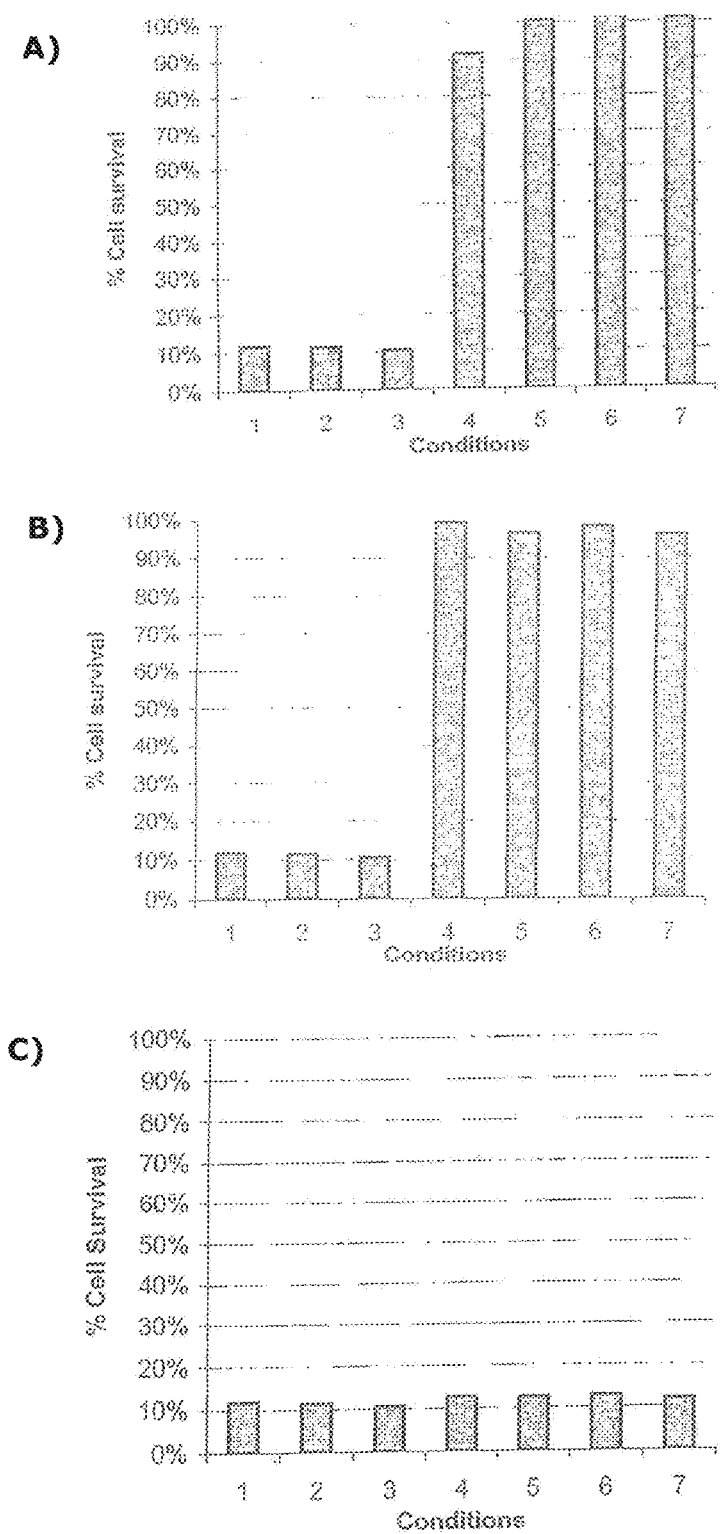
FIG. 3: Pre-treatment of virus (A/Sydney/5/97) with test compounds prior to infection of MDCK cells, A) MD348, B) MD345, and C) Zanamivir (control).

Results for A/Sydney/250/99 are summarised in Table 2 and FIGS. 2A, 2B and 2C. Results for A/Sydney/5/97 are summarised in Table 3 and FIGS. 3A, 3B and 3C.

The results indicate that compounds of Formula (I), MD345, and MD348, neutralized the viruses A/Sydney/25/99 (H1N1) and A/Sydney/5/97 (H3N2) extracellularly. Pre-treatment of viruses with Zanamivir did not affect the infectivity of viruses.

Figure 4:
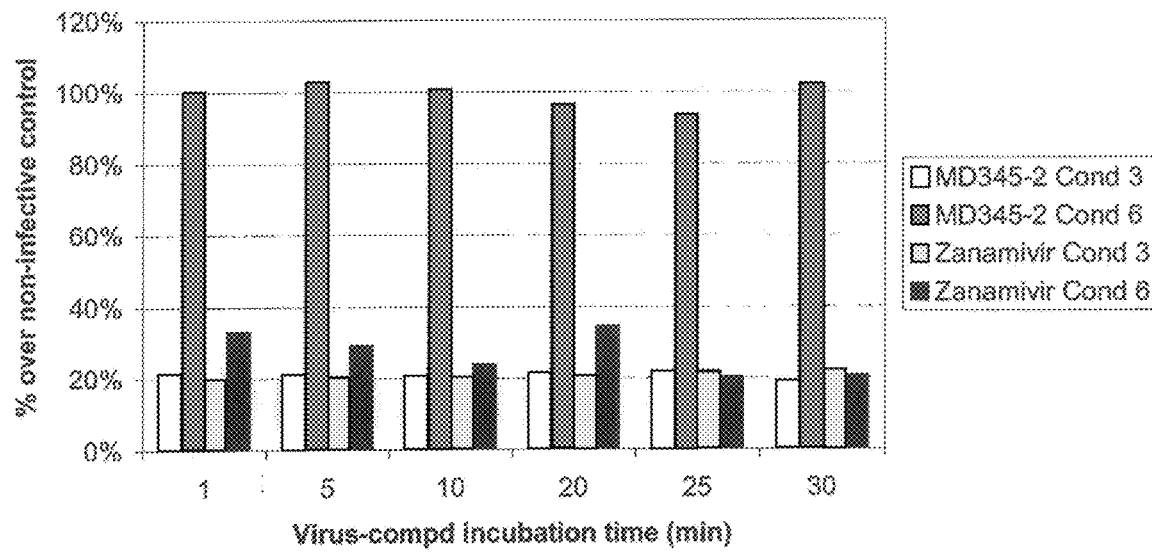
FIG. 4: Pre-treatment of virus (A/Sydney/250/99) with MD345 (test compound) and Zanamivir (control) over varying time periods and conditions prior to infection of MDCK cells.

Subsequent time course comparison of MD345-2 and Zanamivir against A/Sydney/250/99 indicates MD345-2 neutralized both virus in less than 1 minute. Results for A/Sydney/250/99 are summarised in Table 2 and FIGS. 2A, 2B and 2C. Results for A/Sydney/5/97 are summarised in Table 4 and FIG. 4.

TABLE 2

Pre treatment of virus prior to infection of MDCK cells
Test compounds: MD348-2, MD345-2 and Zanamivir (control)
Virus Titre: A/Sydney/25/99

MD348-2

| Conditions | | | | Average |
|---|---|---|---|---|
| 1 | 0.368 | 0.404 | 0.332 | 0.368 |
| 2 | 0.386 | 0.307 | 0.372 | 0.355 |
| 3 | 0.361 | 0.347 | 0.326 | 0.345 |
| 4 | 1.963 | 2.507 | 2.44 | 2.303 |
| 5 | | 2.501 | 2.386 | 2.444 |
| 6 | 2.301 | 2.26 | 2.29 | 2.284 |
| 7 | 2.083 | 2.407 | 2.413 | 2.301 |
| No infection | 2.236 | 2.268 | 2.285 | 2.263 |

MD348-2
% over Control (no Infection)

| | |
|---|---|
| 1 | 16% |
| 2 | 16% |
| 3 | 15% |
| 4 | 102% |
| 5 | 108% |
| 6 | 101% |
| 7 | 102% |
| No Infection | 100% |

MD345-2

| Conditions | | | | Average |
|---|---|---|---|---|
| 1 | 0.368 | 0.404 | 0.332 | 0.368 |
| 2 | 0.386 | 0.307 | 0.372 | 0.355 |
| 3 | 0.361 | 0.347 | 0.326 | 0.345 |
| 4 | 2.384 | 2.468 | 2.219 | 2.357 |
| 5 | 2.37 | 2.109 | 2.277 | 2.252 |
| 6 | 2.305 | 2.303 | 2.206 | 2.271 |
| 7 | 2.203 | 2.14 | 2.168 | 2.170 |
| No infection | 2.236 | 2.268 | 2.285 | 2.263 |

MD345-2
% over Control (no Infection)

| | |
|---|---|
| 1 | 16% |
| 2 | 16% |
| 3 | 15% |
| 4 | 104% |
| 5 | 100% |
| 6 | 100% |
| 7 | 96% |
| No Infection | 100% |

Zanamivir

| Conditions | | | | Average |
|---|---|---|---|---|
| 1 | 0.368 | 0.404 | 0.332 | 0.368 |
| 2 | 0.386 | 0.307 | 0.372 | 0.355 |
| 3 | 0.361 | 0.347 | 0.326 | 0.345 |
| 4 | 0.466 | 0.461 | 0.967 | 0.631 |
| 5 | 0.419 | 0.409 | 0.625 | 0.484 |
| 6 | 0.446 | 0.512 | 0.443 | 0.467 |
| 7 | 0.663 | 0.791 | | 0.727 |
| No infection | 2.236 | 2.268 | 2.285 | 2.263 |

Zanamivir
% over Control (no Infection)

| | |
|---|---|
| 1 | 16% |
| 2 | 16% |
| 3 | 15% |
| 4 | 28% |
| 5 | 21% |
| 6 | 21% |
| 7 | 32% |
| No Infection | 100% |

Notes:
Compounds were dissolved in $H_2O$ to 50 μg/mL. Further dilutions were made in 1 × PBS to 5 μg/mL. Cells were maintained in media containing 1 μg/mL trypsin. Assayed at 72 h post infection. (1000 140711) $0.5 \times 10^{-4}$ virus pre-adsorbed for 1 h, virus removed, cells washed once and fresh media added, incubated for 72 h.

TABLE 3

Pre treatment of virus prior to infection of MDCK cells
Test compounds: MD348-2, MD345-2 and Zanamivir (control)
Virus Titre: A/Sydney/5/97

MD348-2

| Conditions | | | | Average |
|---|---|---|---|---|
| 1 | 0.296 | 0.308 | 0.299 | 0.301 |
| 2 | 0.283 | 0.298 | 0.291 | 0.291 |
| 3 | 0.269 | 0.277 | 0.262 | 0.269 |
| 4 | 1.82 | 2.526 | 2.682 | 2.343 |
| 5 | 2.6 | 2.488 | 2.625 | 2.571 |
| 6 | 2.69 | 2.48 | 2.658 | 2.609 |
| 7 | 2.597 | 2.46 | 2.69 | 2.582 |
| No infection | 2.581 | 2.501 | 2.581 | 2.554 |

MD348-2
% over Control (no Infection)

| | |
|---|---|
| 1 | 12% |
| 2 | 11% |
| 3 | 11% |
| 4 | 92% |
| 5 | 101% |
| 6 | 102% |
| 7 | 101% |
| No Infection | 100% |

MD345-2

| Conditions | | | | Average |
|---|---|---|---|---|
| 1 | 0.296 | 0.308 | 0.299 | 0.301 |
| 2 | 0.283 | 0.298 | 0.291 | 0.291 |
| 3 | 0.269 | 0.277 | 0.262 | 0.269 |
| 4 | 2.547 | 2.621 | 2.451 | 2.540 |
| 5 | 2.444 | 2.473 | 2.486 | 2.468 |
| 6 | 2.568 | 2.523 | 2.456 | 2.516 |
| 7 | 2.491 | 2.437 | 2.437 | 2.455 |
| No infection | 2.581 | 2.501 | 2.581 | 2.554 |

MD345-2
% over Control (no Infection)

| | |
|---|---|
| 1 | 12% |
| 2 | 11% |
| 3 | 11% |
| 4 | 99% |
| 5 | 97% |
| 6 | 98% |
| 7 | 96% |
| No Infection | 100% |

Zanamivir

| Conditions | | | | Average |
|---|---|---|---|---|
| 1 | 0.296 | 0.308 | 0.299 | 0.301 |
| 2 | 0.283 | 0.298 | 0.291 | 0.291 |
| 3 | 0.269 | 0.277 | 0.262 | 0.269 |
| 4 | 0.329 | 0.322 | 0.322 | 0.324 |
| 5 | 0.329 | 0.325 | 0.303 | 0.319 |
| 6 | 0.32 | 0.336 | 0.324 | 0.327 |

TABLE 3-continued

Pre treatment of virus prior to infection of MDCK cells
Test compounds: MD348-2, MD345-2 and Zanamivir (control)
Virus Titre: A/Sydney/5/97

| 7 | 0.322 | 0.298 | 0.293 | 0.304 |
|---|---|---|---|---|
| No infection | 2.581 | 2.501 | 2.581 | 2.554 |

| Zanamivir | |
|---|---|
| % over Control (no Infection) | |
| 1 | 12% |
| 2 | 11% |
| 3 | 11% |
| 4 | 13% |
| 5 | 12% |
| 6 | 13% |
| 7 | 12% |
| No Infection | 100% |

Notes:
Compounds were dissolved in $H_2O$ to 50 µg/mL. Further dilutions were ade in 1 × PBS to 5 µg/mL. Cells were maintained in media containing 1 µg/mL trypsin. Assayed at 72 h post infection. (2000 271011) 1 × $10^{-4}$ virus pre-adsorbed for 1 h, virus removed, cells washed once and fresh media added, incubated for 72 h.

TABLE 4

Time course comparison for pre treatment of virus prior to infection of MDCX cells
Test compounds: MD345-2 and Zanamivir (control)
Virus Titre: A/Sydney/250/99

| | MD345-2 | | | | | | |
|---|---|---|---|---|---|---|---|
| Time (min) | Condition 3 | | | Average | Condition 6 | | Average |
| 1 | 0.335 | 0.354 | 0.395 | 0.361 | 1.752 | 1.664 1.759 | 1.725 |
| 5 | 0.337 | 0.366 | 0.367 | 0.357 | 1.856 | 1.723 1.727 | 1.769 |
| 10 | 0.354 | 0.363 | 0.337 | 0.351 | 1.764 | 1.724 1.717 | 1.735 |
| 20 | 0.354 | 0.373 | 0.359 | 0.362 | 1.705 | 1.645 1.626 | 1.659 |
| 25 | 0.311 | 0.437 | 0.346 | 0.365 | 1.588 | 1.539 1.693 | 1.607 |
| 30 | 0.314 | 0.347 | | 0.331 | 1.762 | 1.756 1.746 | 1.755 |
| Control | 1.829 | 1.71 | 1.625 | 1.721 | 1.829 | 1.71 1.625 | 1.721 |

| | Zanamivir | | | | | | |
|---|---|---|---|---|---|---|---|
| Time (min) | Condition 3 | | | Average | Condition 6 | | Average |
| 1 | 0.356 | 0.318 | 0.337 | 0.338 | 0.798 | | 0.568 |
| 5 | 0.347 | 0.355 | 0.351 | 0.394 | 0.609 | | 0.502 |
| 10 | 0.323 | 0.37 | 0.347 | 0.326 | 0.487 | | 0.407 |
| 20 | 0.347 | 0.358 | 0.353 | 0.461 | 0.728 | | 0.595 |
| 25 | 0.411 | 0.339 | 0.375 | 0.375 | 0.322 | | 0.349 |
| 30 | 0.383 | 0.373 | 0.378 | 0.357 | 0.353 | | 0.355 |
| Control | | | | 1.721 | | | 1.721 |

| | MD345-2 | | Zanamivir | |
|---|---|---|---|---|
| Time (min) | Condition 3 | Condition 6 | Condition 3 | Condition 6 |
| 1 | 21% | 100% | 20% | 33% |
| 5 | 21% | 103% | 20% | 29% |
| 10 | 20% | 101% | 20% | 24% |
| 20 | 21% | 96% | 20% | 35% |
| 25 | 21% | 93% | 22% | 20% |
| 30 | 19% | 102% | 22% | 21% |

Note:
Compounds were dissolved in $H_2O$ to 50 µg/mL. Further dilutions were made in 1 × PBS to 0.5 µg/mL.
Cells were maintained in media containing 1 µg/ml trypsin.
Assayed at 72 h post infection. (1000 140711) 1 × $10^{-4}$ virus pre-adsorbed for 1 h, virus removed, cells washed once and fresh media added, incubated for 72 h.

Example 2: Comparison of Variable Acidic/Anionic Groups on Antiviral Activity of Test Compounds Representative compounds of Formula (I) were utilised to compare the effect of acidic/anionic groups on antiviral activity. The following compounds were tested as representative compounds of Formula (I):

MD314-1: (CHTCA($Z_0$)$_2$-L-Asp-(L-Cyst-$SO_3$H)-Asp-(L-Cyst-$SO_3$H)-L-Asp-(L-Cyst-$SO_3$H)—OH, comprising three sulfonic acids and four carboxylic acids;

MD021-7: CHTGA(Z)$_2$-L-Asp, comprising containing 2 carboxylic acids; and

MD051-3: PK2 TCA(Z)$_2$-L-Asp-L-Asp, comprising 3 carboxylic acids.

Activity against three viral strains were tested. A/Sydney/250/99 (H1N1). A/Mississippi/03/01 (H1N1) Wild Type, and A/Mississippi/03/01 (H1N1) H274Y (Oseltamivir resistant).

Figure 5:
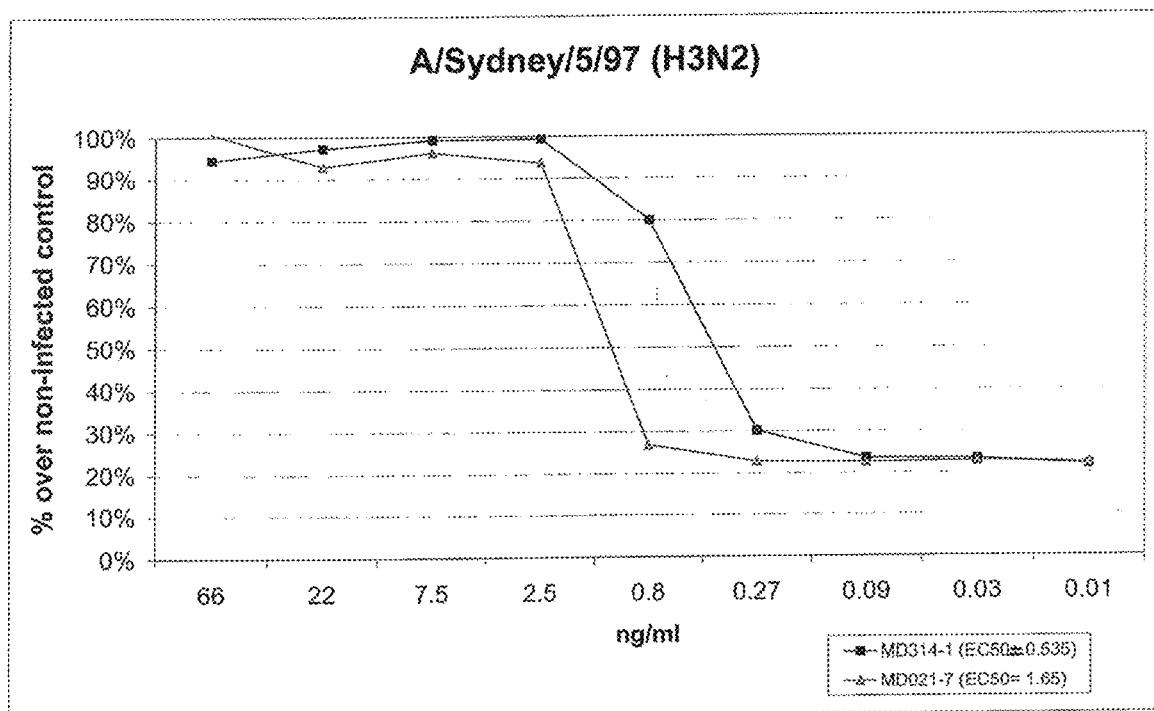
FIG. 5: Comparison of antiviral activity of MD314-1 and MD021-7 against A/Sydney/5/97 (H3N2).
Figure 6:
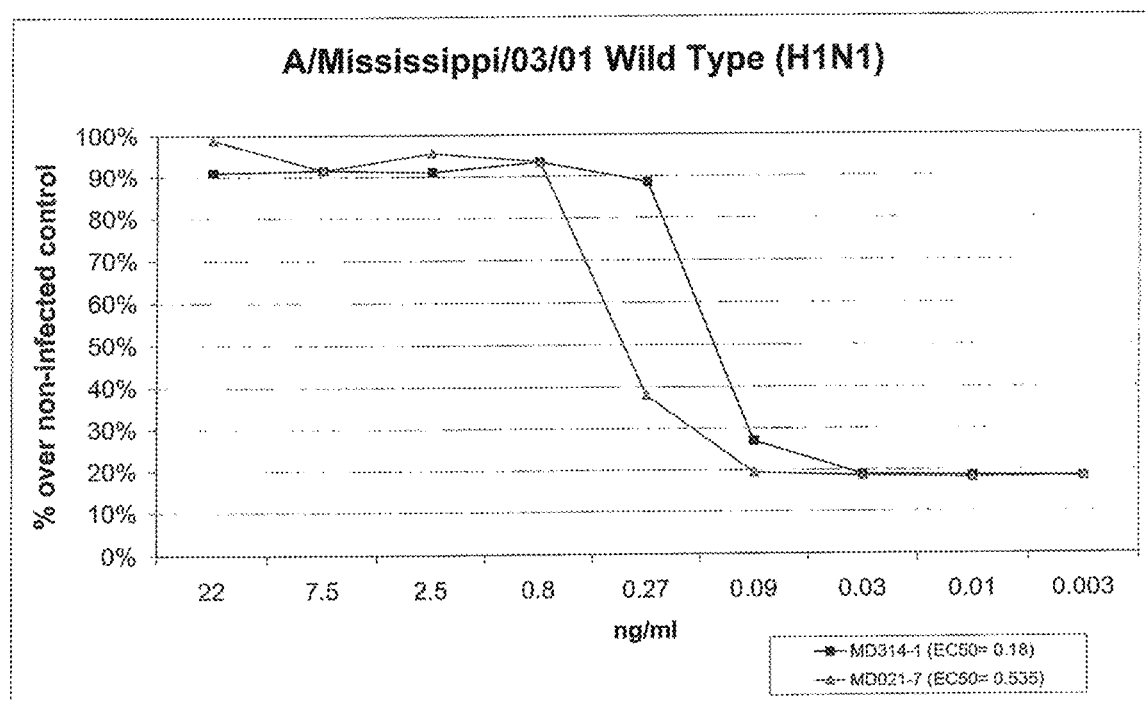
FIG. 6: Comparison of antiviral activity of MD314-1 and MD021-7 against A/Mississippi/03/01 (H1N1) Wild Type.
Figure 7:
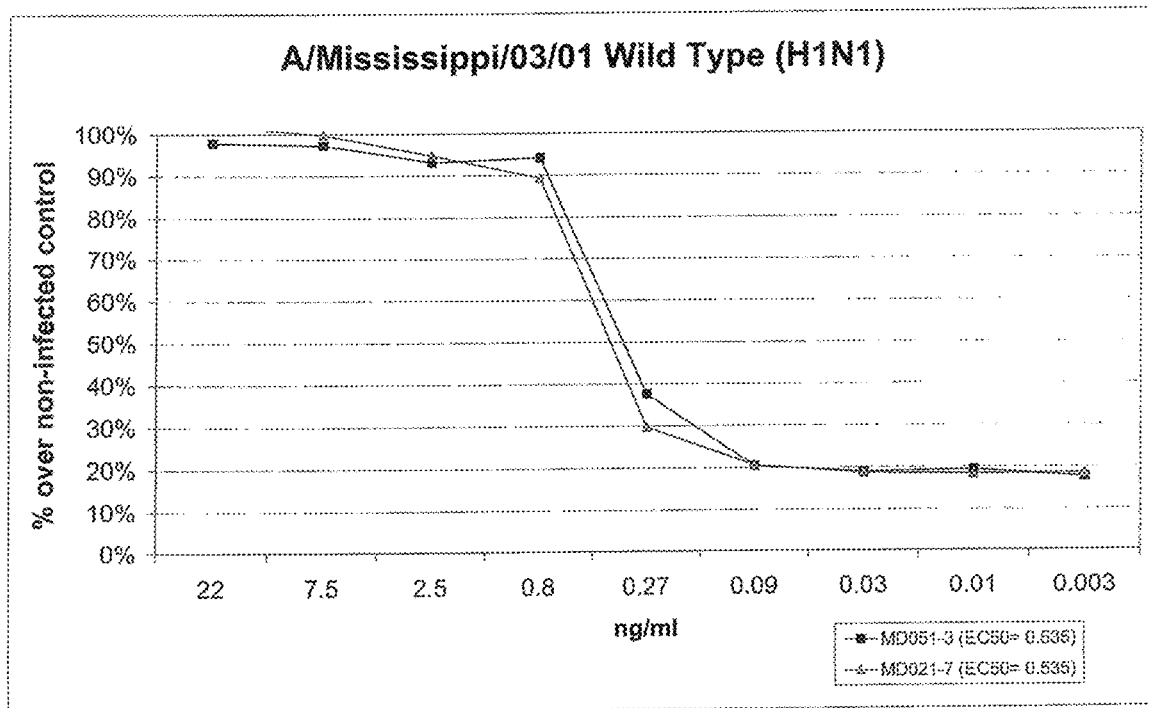
FIG. 7: Comparison of antiviral activity of MD021-7 and MD051-3 against A/Mississippi/03/01 (H1N1) Wild Type.
Figure 8:
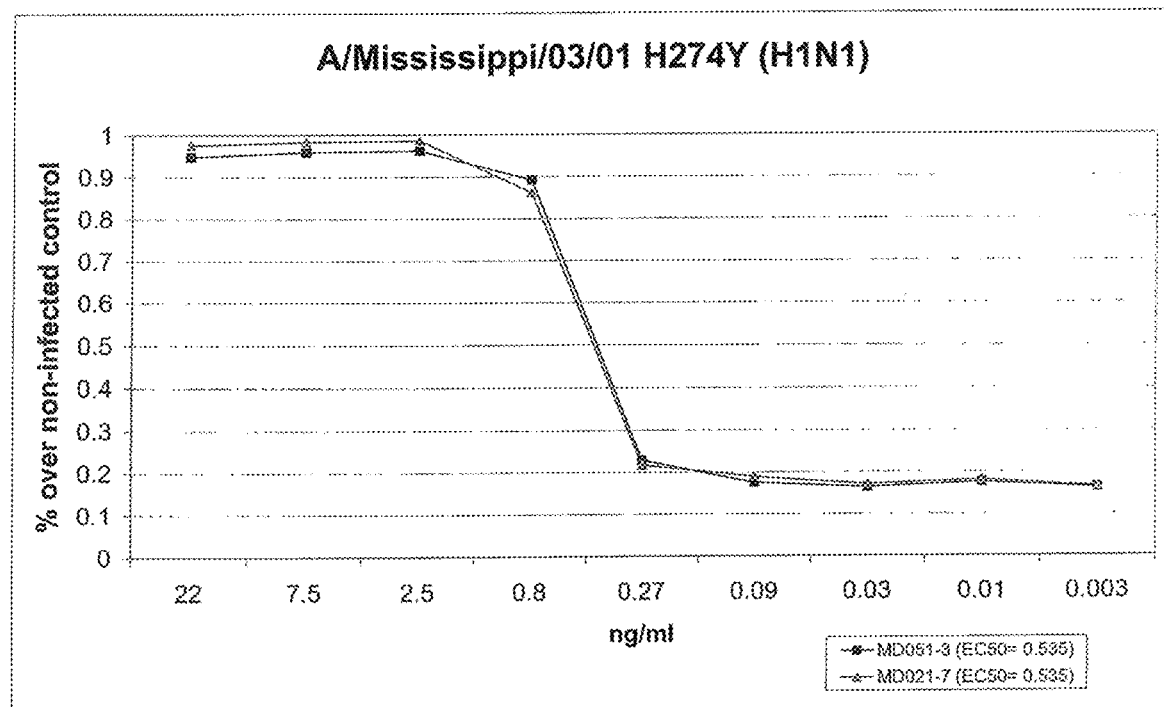
FIG. 8: Comparison of antiviral activity of MD021-7 and MD051-3 against A/Mississippi/03/01 (H1N1) H274Y (Oseltamivir resistant).
Figure 9:
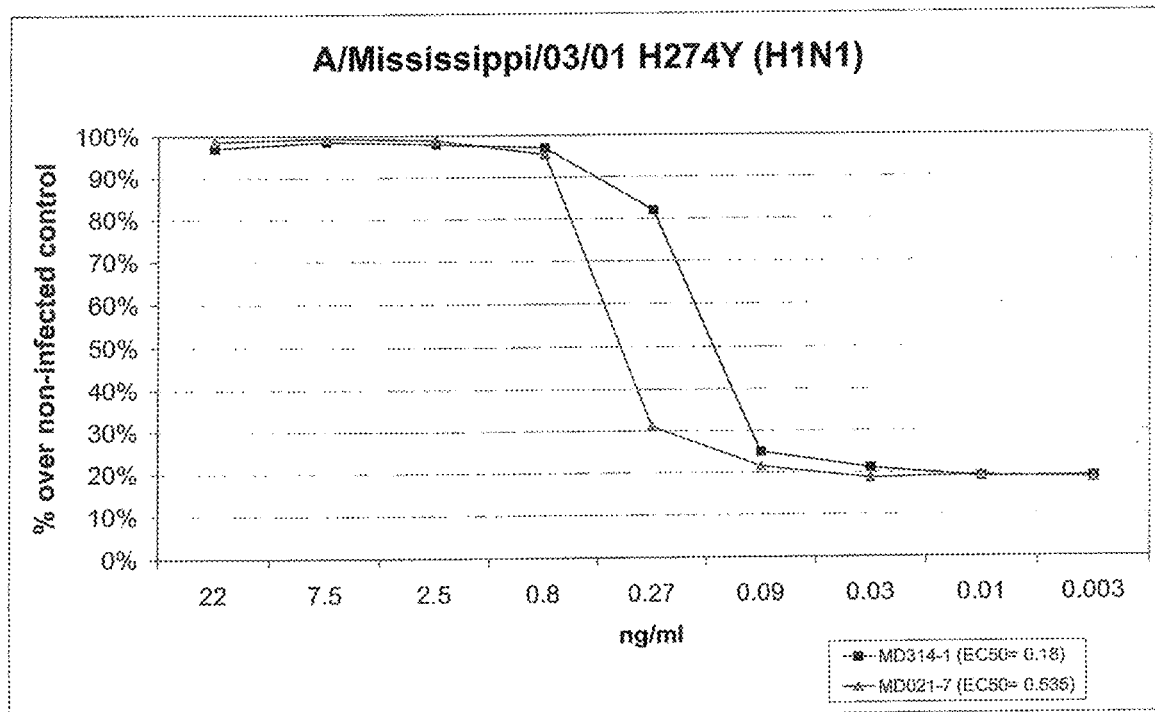
FIG. 9: Comparison of antiviral activity of MD314-1 and MD021-7 against A/Mississippi/03/01 (H1N1) H274Y (Oseltamivir resistant).

Results for A/Sydney/5/97 (H3N2) are summarised in Table 5 and FIG. 5. Results for A/Mississippi/03/01 (H1N1) Wild Type are summarised in Table 5 and FIGS. 6 and 7. Results for A/Mississippi/03/01 (H1N1) H274Y (Oseltamivir resistant) are summarised in Table 5 and FIGS. 8 and 9.

TABLE 5

Comparison of acidic/anionic groups on antiviral activity

| Test Compound | A/Sydney/5/97 (H3N2) | A/Mississippi/03/01 (H1N1) Wild Type | A/Mississippi/03101 (H1N1) H274Y (Oseltamivir resistant) |
|---|---|---|---|
| MD314-1 | 0.535 ng/mL (0.27 nM) | 0.18 ng/mL (0.09 nM) | 0.18 ng/mL (0.09 nM) |
| MD021-7 | 1.65 ng/mL (1.32 nM) | 0.535 ng/mL (0.43 nM) | 0.535 ng/mL (0.43 nM) |
| MD051-3 | 0.156 ng/mL (0.45 nM) | 0.535 ng/mL (0.406 nM) | 0.535 ng/mL (0.406 nM) |

The results indicate that that the antiviral activities of the compounds were proportional to the number of acidic/anionic groups.

Example 3: Modification of Viral Clearance Rates in the Lung and Nasal Turbinates The effect of representative compounds of Formula (I) on rates of viral clearance in the lung and nasal turbinates of mice was assessed. MD021 (CHTCA(Z)$_2$-L-Asp) was tested as a representative compound of Formula (I). Zanamivir and PBS were utilised as controls.

20 mice per group were treated intranasally under anaesthesia with 2 µg MD021, 2 µg of Zanamivir or PBS at days −1, +1, +2, +3, +4 and +5 and infected with a sub-lethal dose of 50 pfu of PR8 influenza virus on day 0. Mice were weighed daily. Five mice per treatment group were killed on days 1, 3, 5 and 7 post infection and their lungs and nasal turbinates were harvested. Lungs were assayed for viral load. Nasal turbinates were stored at −80° C. until analysis.

Figure 10:
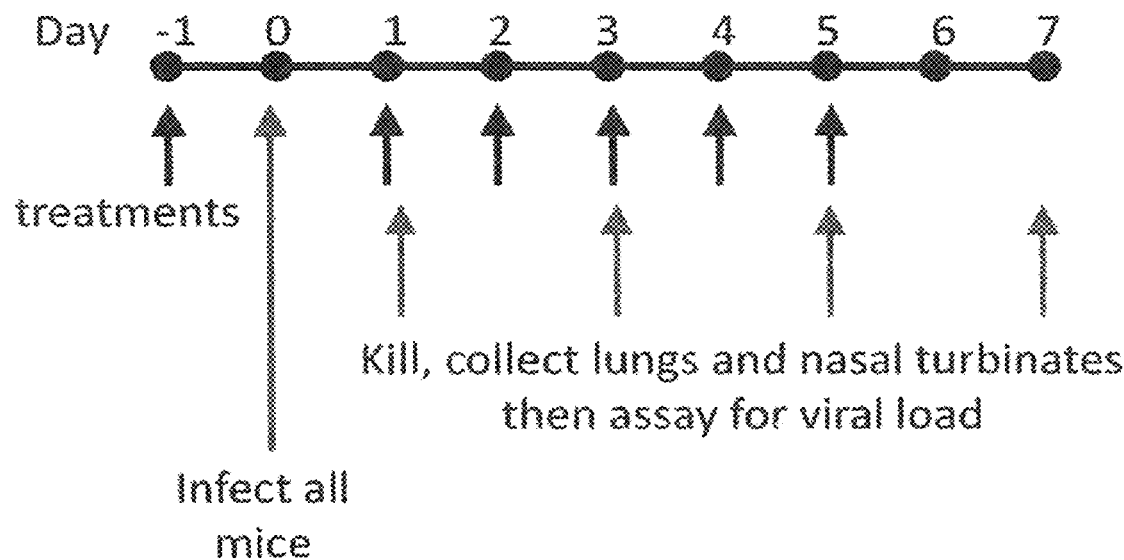
FIG. 10: Summary of timing of treatments, infection and organ harvest for assessment of rates of viral clearance in lungs and nasal turbinates in mice.
Figure 11:
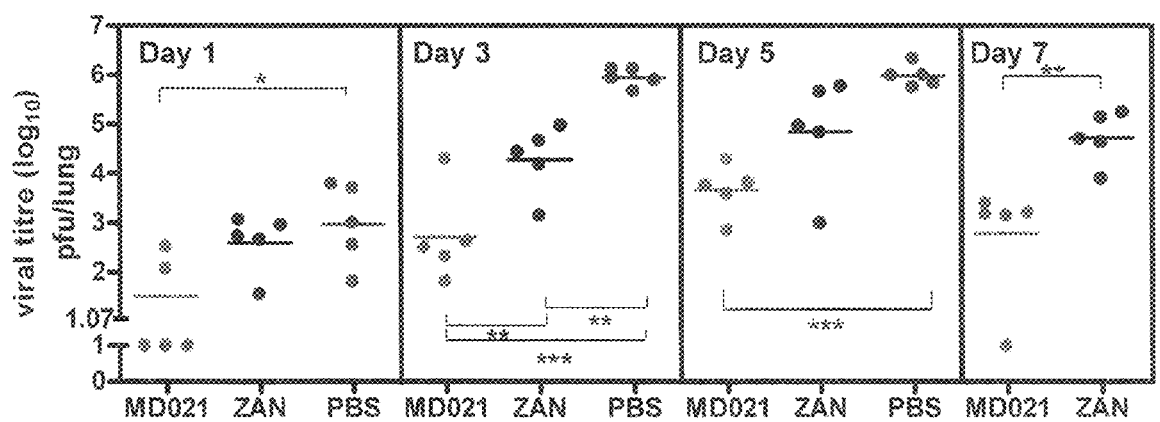
FIG. 11: Comparative lung viral titres in mice for assessment of rates of viral clearance with MD021, Zanamivir and PBS.
Figure 12:
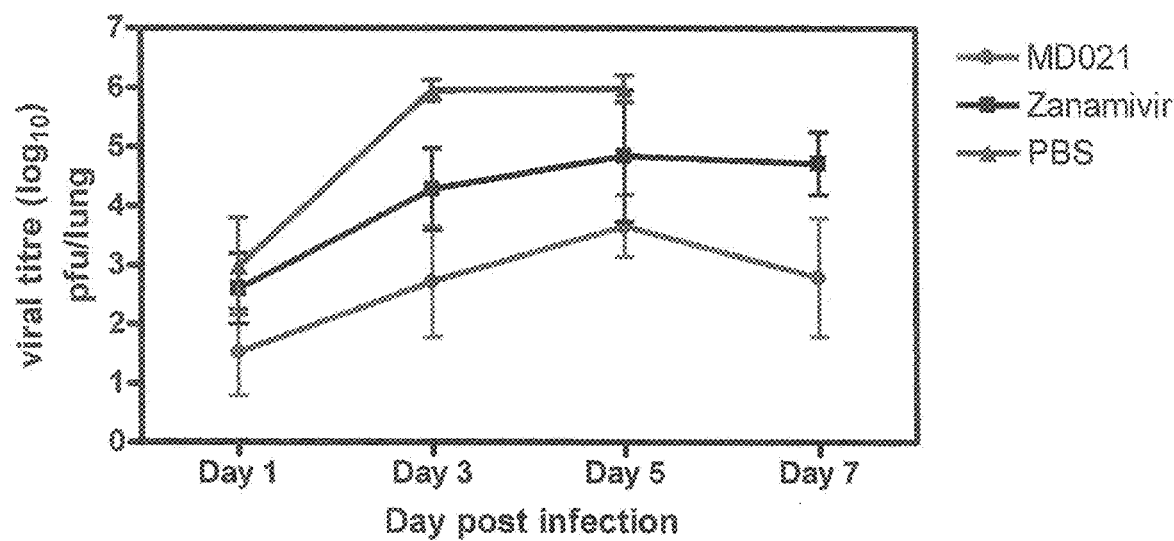
FIG. 12: Comparative lung viral titres in mice for assessment of rates of viral clearance with MD021, Zanamivir and PBS at days 1, 3, 5 and 7 post infection.
Figure 13:
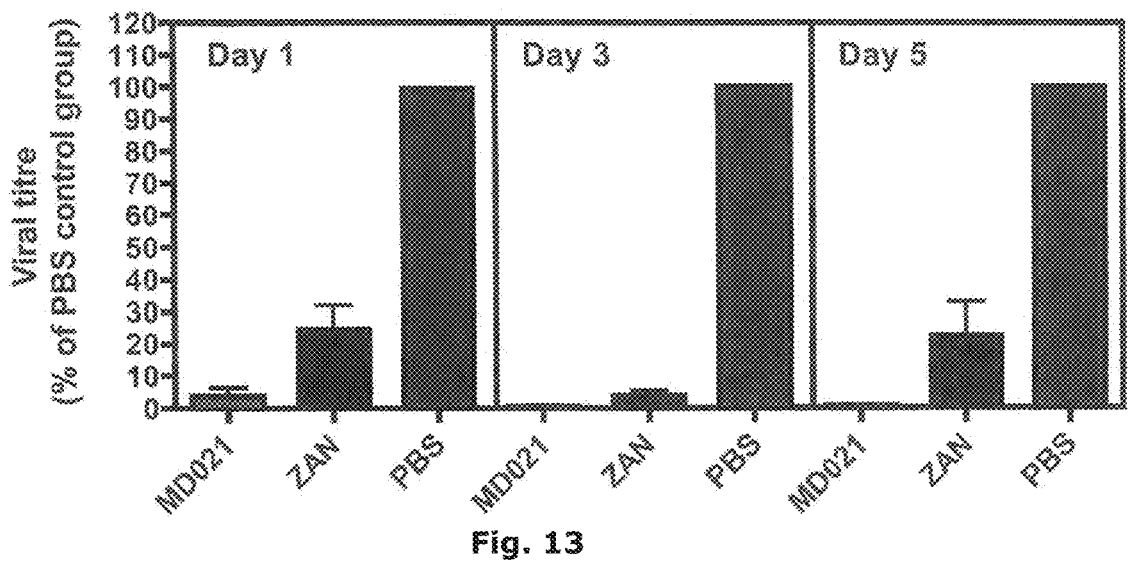
FIG. 13: Comparative viral titre expressed as a percentage of the mean of the PBS control group.
Figure 14:
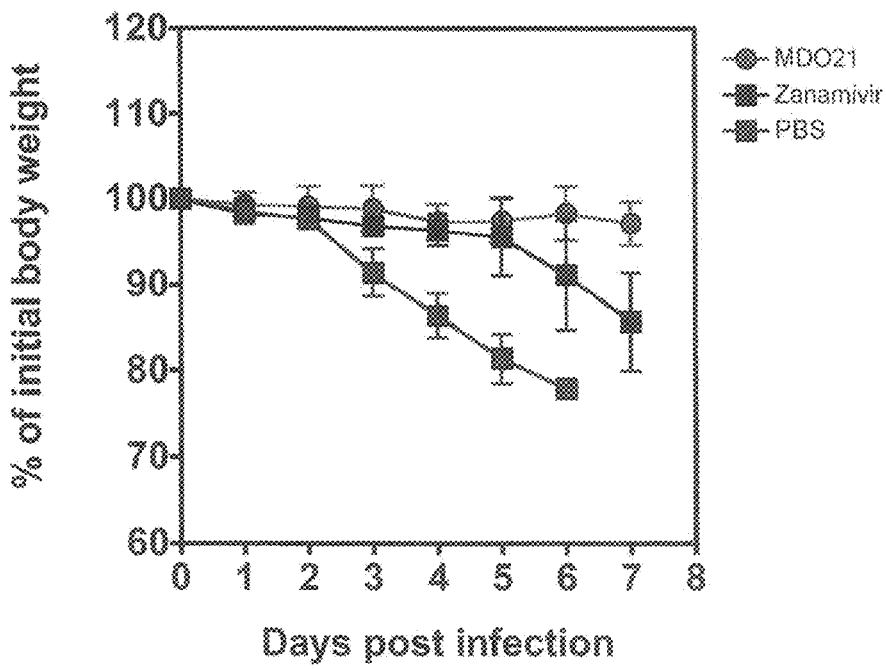
FIG. 14: Comparative weight loss in mice for assessment of rates of viral clearance with MD021, Zanamivir and PBS.
Figure 15:
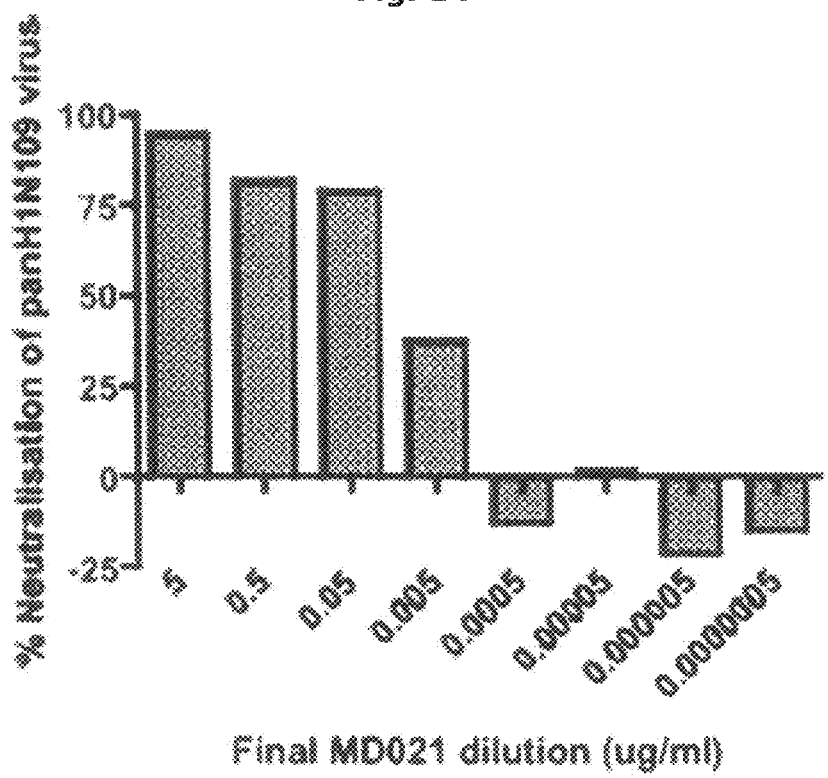
FIG. 15: Neutralisation of A/California/7/09 (pan H1N1) in vitro.

All treatments, infection and killing of mice occurred within a two hour window 24 hours after the intervention of the day before. Mice did not receive treatment on the same day they were killed. The timing of treatments infection and organ harvest are summarised in FIG. 10.

Results are detailed in Table 6 and FIGS. 11 to 14. At all time points, lung viral load (expressed as $\log_{10}$) in MD021 treated mice was significantly lower than that for PBS treated mice. At Days 3 and 7 post infection lung viral load MD021 treated mice was also significantly lower than that for Zanamivir treated mice. Results were assessed using a one-way ANOVA with Tukey post-test on day 1, 3 and 5 data and a Mann Witney t-test on day 7 data. The threshold of the assay was $10^{1.07}$. Negative samples assigned value of $10^1$.

Untreated mice (PBS control treatment) did not survive to day 7 despite the low dose of virus given.

Weight loss was assessed for groups of mice that were not killed until Day 7 post-infection. Results indicate minimal weight loss after treatment with MD021, substantially less that weight loss observed with Zanamivir administration at later time points.

TABLE 6

Modification of viral clearance rates in the lung and nasal turbinates

|  | MD021 | Zanamivir | PBS |
|---|---|---|---|
| Individual titres | | | |
| Day 1 | 1.00 | 2.73 | 2.56 |
|  | 2.52 | 3.07 | 1.82 |
|  | 2.08 | 2.66 | 3.71 |
|  | 1.00 | 2.96 | 3.01 |
|  | 1.00 | 1.57 | 3.79 |
| Day 3 | 1.82 | 4.44 | 6.12 |
|  | 2.33 | 4.66 | 5.68 |
|  | 2.51 | 4.97 | 5.90 |
|  | 4.31 | 4.19 | 6.12 |
|  | 2.63 | 3.16 | 5.94 |
| Day 5 | 2.85 | 4.84 | 5.75 |
|  | 3.77 | 3.00 | 5.84 |
|  | 3.59 | 4.97 | 5.99 |
|  | 3.82 | 5.77 | 6.00 |
|  | 4.30 | 5.66 | 5.34 |
| Day 7 | 3.41 | 4.70 | |
|  | 3.18 | 5.14 | |
|  | 3.22 | 3.90 | |
|  | 3.16 | 4.64 | |
|  | 1.00 | 5.24 | |
| Group mean titres | | | |
| Day 1 | 1.52 | 2.60 | 2.98 |
| Day 3 | 2.72 | 4.28 | 5.95 |
| Day 5 | 3.67 | 4.85 | 5.98 |
| Day 7 | 2.79 | 4.72 | |

Statistical analysis of the weight loss curves by 2-way repeated measures ANOVA showed a highly significant difference in the treatment curves ($p<0.0001$). Note, 2-way repeated measures ANOVA was only completed for data acquired up until day 5 post infection as the PBS group did not have complete data on days 6 and 7 due to premature death. Bonferroni post-test revealed that both Zanamivir and MD021 were significantly different from PBS on days 3, 4 and 5 ($p<0.001$). The same analysis performed on the complete weight loss curves for MD021 and Zanamivir only revealed a statistically significant difference in the two weight loss curves overall ($p=0.0443$) with the Bonferroni post-test showing that the significant differences occurred on day 6 ($p<0.01$) and day 7 ($p<0.001$).

The results indicate that multiple daily treatments with 2 μg of compound MD021 were able to reduce lung viral load significantly compared to mice treated similarly with PBS at days 1, 3 and 5 post infection and also with 2 μg of Zanamivir at day 3 and 7 post infection. The significant reduction in viral load was accompanied by less weight loss in the mice and is expected to equate to substantial reduction in disease severity. The minimal weight loss with MD021 throughout the entire disease course was striking and significantly better than Zanamivir at later time points.

Although mice were given a dose of PR8 virus that, in normal circumstances, is sub-lethal, all mice receiving PBS control treatment lost weight and were killed prior to day 7 post infection. The unexpected premature deaths may be associated with detrimental effect of daily anaesthetic and intranasal administration of 50 μL of liquid. However, the MD021 and Zanamivir groups, treatment outweighed any detrimental effects.

Example 4: CPE Assay Screen

CPE assay screens were conducted for representative compounds of Formula (I) in accordance with the general procedure for CPE assay outlined above. Results are detailed in Tables 7 and 8. Specific in vitro antiviral screens were also conducted for a range of viral strains, including Influenza A H7N9 A/Anhui/1/2003 (Table 9), Influenza A H5N1 Hong Kong/213/2003 (Table 10), Influenza A H3N2 Perth/16/2009 (Table 11), Influenza A H7N9 A/Anhui/1/2003 (Table 12), Influenza A H1N1 California 07/2009 (Table 13), Influenza A H5N1 Duck/MN/1525/81 (Table 14), Influenza A H5N1 Thailand/16/2004 (Table 15), Influenza A virus H1N1, A/Mississippi/3/2001 H275Y, Oseltamivir Resistant (Table 16), Influenza A virus H5N1 Duck/MN/1525/81 (Table 17). Influenza B virus. B/Brisbane/60/2008 (Table 18), Influenza B virus, B/Florida/4/2006 (Table 19) and A/Sydney/250/99 (H1N1) (Table 20).

Anti-influenza activity data indicates that the more acidic groups in compounds of Formula (I) the higher the antiviral activity.

The anti-influenza activity of representative compounds of Formula (I) were further assessed in subsequent CPE assays (Table 38) and at differing viral titres (Table 39).

Example 5: Anti Influenza Virus Activity Against Oseltamivir Resistant Strains

The anti influenza virus activity against Oseltamivir resistant strains was assessed for representative compounds of Formula (I). Inhibition of plaque size and plaque number were recorded. Oseltamivir was utilised a control. Results are detailed in Table 21.

Example 6: Viral Plaque Reduction Assay

Representative compounds of Formula (I) were assessed in a viral plaque reduction against each of CA/07/2009 virus H1N1 and A/PR/8 virus H1N1. Zanamivir was utilised a control. Results are detailed in Table 22 and 23, respectively.

Example 7: In Vivo Mouse Efficacy Data for Representative Compounds of Formula (I)

The in vivo efficacy of representative compounds of Formula (I) was assessed in mice against a range of viral infections.

Table 24 details mouse survival after virus infection with one of A/California/04/2009 (H1N1) A/Victoria/3/75 (H3N2), A/Mississippi/3/01 H275Y, Oseltamivir resistant virus (H1N1), A/Duck/MN/1525/81 (H5N1), or B/Sichuan/379/99 (FluB) and single compound treatment with representative compounds of Formula (I) at different dosages.

Table 25 details mouse survival after intranasal virus infection by A/PR/8 virus (500 pfu/mouse) and single compound treatment with representative compounds of Formula (I) at different dosages and times.

Table 26 details the effects of single intranasal treatment with representative compounds of Formula (I) when administered at different dosages post-infection on survival from an influenza A/California/04/2009 (H1N1pdm) virus infection in mice. Zanamivir was used as a control and saline was used as a placebo.

Table 27 details the effects of single intranasal treatment with representative compounds of Formula (I) when administered at different dosages 48 hrs post-infection on survival from an influenza A/PR/8 (H1N1) virus infection in mice. Zanamivir was used as a control and saline was used as a placebo.

Table 28 details the effects of single intranasal treatment with representative compounds of Formula (I) when administered at 48 hrs post-infection on survival from an influenza A/PR/8 (H1N1) virus infection in mice. Zanamivir was used as a control and saline was used as a placebo.

Table 29 details the effects of single intranasal treatment with representative compounds of Formula (I) when administered at different dosages at 48 hrs post-infection on survival from an influenza A/PR/8 (H1N1) virus (500 pfu/mouse) infection in mice. Zanamivir was used as a control and saline was used as a placebo.

Table 30 details the effects of single intranasal treatment with representative compounds of Formula (I) when administered at differing dosages 60 hrs post-infection on survival from an influenza A/PR/8 (H1N1) virus (500 pfu/mouse) infection in mice. Zanamivir was used as a control and saline was used as a placebo. Zanamivir was used as a control and saline was used as a placebo.

Table 31 details the effects of single intranasal treatment with representative compounds of Formula (I) when administered at 60 hrs post-infection on survival from an influenza A/PR/8 (H1N1) virus (500 pfu/mouse) infection in mice. Zanamivir was used as a control and saline was used as a placebo.

Table 32 details the effects of single intranasal treatment with representative compounds of Formula (I) when administered at 72 hrs post-infection on survival from an influenza A/PR/8 (H1N1) virus (500 pfu/mouse) infection in mice.

Table 33 details the effects of single intranasal treatment with representative compounds of Formula (I) when administered at 72 hrs post-infection on survival from an influenza A/PR/8 (H1N1) virus (500 pfu/mouse) infection in mice.

Table 34 details the effects of single treatment with representative compounds of Formula (I) when administered intraperitoneally at 1 hr before lethal challenge of influenza A/PR/8 (H1N1) virus (500 pfu/mouse) on mice.

Table 35 details the effects of treatment with representative compounds of Formula (I) when administered intraperitoneally at 4 hrs post-infection (20 μg/mouse/day×5 days) on survival from an influenza A/PR/8 (H1N1) virus (500 pfu/mouse) infection in mice.

The results presented in Tables 34 and 35 indicate that compounds of Formula (I) can be used in systemic treatment of infection.

Table 36 details the effects of treatment with representative compounds of Formula (I) when administered intranasally at 60 hrs post-infection on survival from an influenza A/PR/8 (H1N1) virus (500 pfu/mouse) infection in mice.

Table 37 details the effects of treatment with representative compounds of Formula (I) when administered intranasally at 60 hrs post-infection on survival from an influenza A/PR/8 (H1N1) virus (500 pfu/mouse) infection in mice.

Table 38 details the effects of treatment with representative compounds of Formula (I) when administered intraperitoneally at 1 hr before lethal challenge of influenza A/PR/8 (H1N1) virus (500 pfu/mouse) on mice.

The results from in vitro and in vivo tests demonstrate that compounds of Formula (I) are potent against a number of flu strains including flu A, B, avian flu and drug resistant strains. Furthermore, the results demonstrate that compounds of Formula (I) did not exhibit cytotoxicity.

With regard to mouse studies, it was found that infected mice generally lost less body weight and/or recovered faster when treated with compounds of Formula (I) when compared with either a saline placebo and/or a control (i.e. Zanamivir). Furthermore, it was found that compounds of Formula (I) were effective after administration to the nasal cave in mice for a period or more than 11 days.

The in vivo efficacy data indicates that the compounds of Formula (I) were at least 75 fold (at weight dosage) or >400 fold (at molar dosage) more active than a Zanamivir control.

With regard to in vivo efficacy data for mice infected with virus Flu A PR8 (500 pfu/mouse) comparative time based intranasal administrations of representative compounds of the invention at 48 hrs, 60 hrs, or 72 hrs after infection resulted in survival of the majority of mice, and a maximum body weight loss <15% (only three mice body weight loss between 20-25%).

With regard to in vivo efficacy data for mice infected with virus Influenza A/PR/8 virus (500 pfu/mouse), intraperitoneally administrations of representative compounds of the invention resulted in survival of all mice, and indicates that compounds of the invention may be used for systemic treatment of infection.

Two representative compounds of Formula (I), MD185 and MD317 were tested in a hERG $IC_{50}$ (hERG-CHO, automated patch-clamp) assay. Both results indicated that the two compounds were safe with regard to cardiac toxicity. Furthermore, MDI 85 and MD317 were tested in Kinome scan, there were no significant interaction between compounds and kinases at 100 nM.

TABLE 7

| | | \multicolumn{8}{c}{CPE assay screen} |
|---|---|---|---|---|---|---|---|---|---|
| Compound | | $EC_{50}$ CA/07/2009 | | $EC_{50}$ Duck/MN/1525/81 | | $EC_{50}$ Perth/16/2009 | | $EC_{50}$ Florida/4/2006 | |
| No. | MW | ng/ml | nM | ng/ml | nM | ng/ml | nM | ng/ml | nM |
| MD015 | 1166 | 7 | 6 | 0.4 | 0.34 | 7.8 | 6.7 | 2.5 | 2.1 |
| MD016 | 1166 | 9 | 7.7 | 0.6 | 0.51 | 3.3 | 2.8 | 8.2 | 7 |
| MD021 | 1243 | 24 | 19.3 | 0.3 | 0.24 | 4.6 | 3.7 | 0.38 | 0.3 |
| MD051 | 1318 | 10 | 7.58 | 0.7 | 0.53 | 26 | 19.7 | 1.5 | 1.13 |
| MD206 | 1187 | 2 | 1.68 | 0.7 | 0.59 | 7.3 | 6.1 | >10000 | >8.4 μM |
| MD082 | 1110 | 7 | 6.3 | 0.4 | 0.36 | 8.4 | 7.5 | 15 | 13.5 |
| MD102 | 1274 | 10 | 7.85 | >10000 | >7.8 μM | >10000 | >7.8 μM | >10000 | >7.8 μM |
| MDII2 | 1246 | >2000 | >1.6 μM | 0.7 | 0.56 | >10000 | >8 μM | 6.5 | 5.2 |
| MD123 | 974 | 8 | 8.2 | 0.7 | 0.72 | >10000 | >10 μM | 0.96 | 0.98 |
| MD214 | 1340 | 7 | 5.22 | 0.2 | 0.15 | >10000 | >7.4 μM | 2.5 | 1.86 |
| MD154 | 1485 | 9 | 6.06 | <0.13 | <0.087 | <0.13 | <0.087 | <0.13 | <0.087 |

TABLE 7-continued

CPE assay screen

| | | | | | | | | | |
|---|---|---|---|---|---|---|---|---|---|
| MD219 | 1712 | 5 | 2.92 | 0.5 | 0.29 | >10000 | >5.8 μM | 1.7 | 0.99 |
| MD242 | 1215 | 8 | 6.58 | 0.84 | 0.7 | | 4.2 | 3.46 | 0.71 | 0.58 |
| MD185 | 1852 | 6 | 3.2 | <0.13 | <0.07 | | <0.13 | <0.07 | <0.13 | <0.07 |
| MD191 | 1457 | 9 | 6.1 | <0.13 | <0.089 | | <0.13 | <0.089 | 0.32 | 0.21 |

| Compound code | Description of Structure | Molecular Weight |
|---|---|---|
| MD015 | PK1 PYR(Z)$_2$ | 1166 |
| MD016 | PK2 PYR(Z)$_2$ | 1166 |
| MD021 | CHTCA(Z)$_2$-L-Asp | 1243 |
| MD051 | PK2 TCA(Z)$_2$-L-Asp-L-Asp | 1318 |
| MD206 | CHTCA(Z$_b$)$_2$-L-Asp | 1187 |
| MD082 | PK1 Succinyl-SO$_3$H-(Z)$_2$ | 1110 |
| MD102 | CHTCA(Z$_{2b}$)$_2$(L-Asp)$_2$ | 1274 |
| MD112 | CHTCA(Z$_3$)$_2$(L-Asp)$_2$ | 1246 |
| MD123 | C$_8$(Z$_3$)$_2$Suberic acid | 974 |
| MD214 | PK1 PYR(Z$_b$)$_2$(D-Asp)$_2$ | 1340 |
| MD154 | CHTCA(Z$_0$)$_2$-L-Asp(NHCH$_2$SO$_3$H)$_2$ | 1485 |
| MD219 | PK2 PYR(Z$_b$)$_2$[(D-Asp)(NHCH$_2$SO$_3$H)$_2$]$_2$ | 1712 |
| MD242 | CHTCA(Z$_p$)$_2$-L-Asp | 1215 |
| MD185 | PK2 PYR(Z$_n$)$_2$[D-Asp(NHCH$_2$SO$_3$H)$_2$]$_2$ | 1852 |
| MD191 | CHTCA(Z$_n$)$_2$-D-Asp(NHCH$_2$SO$_3$H)$_2$ | 1457 |

*CC$_{50}$ > 10,000 ng/mL
MDCK cell line

TABLE 8

Anti-influenza virus activity derived from CPE assay* (EC$_{50}$ nM)

| Flu Virus | MD185 (MW1852) | MD314 (MW1982) | MD345 (MW2201) | MD348 (MW1982) | MD021 (MW1243) | Zanamivir (MW332) |
|---|---|---|---|---|---|---|
| A/Sydney/250/99 | 0.29 | 0.077 | 0.052 | 0.058 | 0.186 | >198 |
| A/Solomon Island/3/06 | 0.29 | 0.03 | 0.043 | 0.016 | 0.144 | >44 |
| A/Townsville/74/2011 | 0.74 | 0.09 | 0.041 | 0.06 | 0.40 | >15 |
| A/Mississippi/03/01 WT | 0.89 | 0.09 | 0.24 | 0.27 | 0.43 | >66 |
| A/Mississippi/03/01H274Y | 0.89 | 0.09 | 0.24 | 0.27 | 0.43 | >66 |
| A/Perth/261/2009 | 0.49 | 0.36 | 0.32 | 0.35 | 0.57 | 6.6 |
| A/Victoria/170/2012 | 2.7 | 1.0 | 0.53 | 0.83 | 2.0 | >596 |
| A/Sydney/5/97 | 2.7 | 0.41 | 0.83 | 1.26 | 2.0 | >>24 |
| A/Victoria/503/06 | 6.5 | 4.4 | 2.2 | 4.5 | 4.0 | >198 |
| B/Townsville/2/2011 | 1.7 | 0.38 | 0.24 | 0.28 | 0.95 | >1789 |

*CC$_{50}$ > 600 ng/ml MDCK cell line
** values are the means of at least three determinations

TABLE 9

In Vitro Antiviral Screen (Influenza A virus H7N9, A/Anhui/1/2003)

| Compound No. | Drug Assay Name | EC$_{50}$ (μg/ml) | EC$_{90}$ (μg/ml) | CC$_{50}$ (μg/ml) | *SI$_{50}$ | **SI$_{90}$ |
|---|---|---|---|---|---|---|
| MD051 | Virus yield reduction/Neutral Red (Toxicity) | | 0.0031 | >1.0 | | >312 |
| MD051 | Neutral Red (Cytopathic effect/Toxicity) | <0.00032 | | >1.0 | >3100 | |
| MD154 | Virus yield reduction/Neutral Red (Toxicity) | | 0.01 | >1.0 | | >100 |
| MD154 | Neutral Red (Cytopathic effect/Toxicity) | <0.00032 | | >1.0 | >3100 | |
| MD185 | Virus yield reduction/Neutral Red (Toxicity) | | 0.00185 | >1.0 | | >540 |
| MD185 | Neutral Red (Cytopathic effect/Toxicity) | <0.00032 | | >1.0 | >3100 | |
| Ribavirin | Virus yield reduction/Neutral Red (Toxicity) | | 8.25 | >1000 | | >121 |
| Ribavirin | Neutral Red (Cytopathic effect/Toxicity) | 24 | | >1000 | >42 | |

*SI$_{50}$ = CC$_{50}$/EC$_{50}$
**SI$_{90}$ = CC$_{50}$/EC$_{90}$

TABLE 10

In Vitro Antiviral Screen (Influenza A virus H5N1, Hong Kong/213/2003)

| Compound No. | Drug Assay Name | EC$_{50}$ (μg/ml) | EC$_{90}$ (μg/ml) | CC$_{50}$ (μg/ml) | *SI$_{50}$ | **SI$_{90}$ |
|---|---|---|---|---|---|---|
| MD051 | Virus yield reduction/Neutral Red (Toxicity) | | <0.00032 | >1.0 | | >3100 |
| MD051 | Neutral Red (Cytopathic effect/Toxicity) | <0.00032 | | >1.0 | >3100 | |
| MD154 | Virus yield reduction/Neutral Red (Toxicity) | | <0.00032 | >1.0 | | >3100 |

TABLE 10-continued

In Vitro Antiviral Screen (Influenza A virus H5N1, Hong Kong/213/2003)

| Compound No. | Drug Assay Name | EC$_{50}$ (μg/ml) | EC$_{90}$ (μg/ml) | CC$_{50}$ (μg/ml) | *SI$_{50}$ | **SI$_{90}$ |
|---|---|---|---|---|---|---|
| MD154 | Neutral Red (Cytopathic effect/Toxicity) | <0.00032 | | >1.0 | >3100 | |
| MD185 | Virus yield reduction/Neutral Red (Toxicity) | | <0.00032 | >1.0 | | >3100 |
| MD185 | Neutral Red (Cytopathic effect/Toxicity) | <0.00032 | | >1.0 | >3100 | |
| Ribavirin | Virus yield reduction/Neutral Red (Toxicity) | | 14.68 | >1000 | | >68 |
| Ribavirin | Neutral Red (Cytopathic effect/Toxicity) | 17 | | >1000 | >59 | |

*SI$_{50}$ = CC$_{50}$/EC$_{50}$
**SI$_{90}$ = CC$_{50}$/EC$_{90}$

TABLE 11

In Vitro Antiviral Screen (Influenza A virus H3N2, Perth/16/2009)

| Compound No. | Drug Assay Name | EC$_{50}$ (μg/ml) | EC$_{90}$ (μg/ml) | CC$_{50}$ (μg/ml) | *SI$_{50}$ | **SI$_{90}$ |
|---|---|---|---|---|---|---|
| MD185 | Visual (Virus yield reduction/Neutral Red) | | 0.00086 | >0.32 | | >370 |
| MD185 | Neutral Red (Cytopathic effect/Toxicity) | 0.0001 | | >0.32 | >3200 | |
| MD317 | Visual (Virus yield reduction/Neutral Red) | | 0.00173 | >0.32 | | >180 |
| MD317 | Neutral Red (Cytopathic effect/Toxicity) | 0.00032 | | >0.32 | >1000 | |
| MD345 | Visual (Virus yield reduction/Neutral Red) | | 0.00485 | >0.32 | | >66 |
| MD345 | Neutral Red (Cytopathic effect/Toxicity) | 0.00054 | | >0.32 | >590 | |
| MD349 | Visual (Virus yield reduction/Neutral Red) | | 0.00115 | >0.32 | | >280 |
| MD349 | Neutral Red (Cytopathic effect/Toxicity) | 0.0006 | | >0.32 | >530 | |
| MD352 | Visual (Virus yield reduction/Neutral Red) | | 0.00208 | >0.32 | | >150 |
| MD352 | Neutral Red (Cytopathic effect/Toxicity) | 0.00038 | | >0.32 | >840 | |
| Ribavirin | Visual (Virus yield reduction/Neutral Red) | | 4.4 | >320 | | >73 |
| Ribavirin | Neutral Red (Cytopathic effect/Toxicity) | 5 | | >320 | >64 | |

*SI$_{50}$ = CC$_{50}$/EC$_{50}$
**SI$_{90}$ = CC$_{50}$/EC$_{90}$

TABLE 12

In Vitro Antiviral Screen (Influenza A virus H7N9, A/Anhui/1/2003)

| Compound No. | Drug Assay Name | EC$_{50}$ (μg/ml) | EC$_{90}$ (μg/ml) | CC$_{50}$ (μg/ml) | *SI$_{50}$ | **SI$_{90}$ |
|---|---|---|---|---|---|---|
| MD185 | Visual (Virus yield reduction/Neutral Red) | | <0.0006 | >2.0 | | >3333 |
| MD185 | Neutral Red (Cytopathic effect/Toxicity) | 0.001 | | >2.0 | >2000 | |
| MD317 | Visual (Virus yield reduction/Neutral Red) | | 0.01 | >2.0 | | >200 |
| MD317 | Neutral Red (Cytopathic effect/Toxicity) | 0.015 | | >2.0 | >130 | |
| MD345 | Visual (Virus yield reduction/Neutral Red) | | 0.01 | >2.0 | | >200 |
| MD345 | Neutral Red (Cytopathic effect/Toxicity) | 0.025 | | >2.0 | >80 | |
| MD349 | Visual (Virus yield reduction/Neutral Red) | | <0.0006 | >2.0 | | >3333 |
| MD349 | Neutral Red (Cytopathic effect/Toxicity) | 0.0042 | | >2.0 | >480 | |
| MD352 | Visual (Virus yield reduction/Neutral Red) | | <0.0006 | >2.0 | | >3333 |
| MD352 | Neutral Red (Cytopathic effect/Toxicity) | 0.00063 | | >2.0 | >3200 | |
| Ribavirin | Visual (Virus yield reduction/Neutral Red) | | 2.20 | >320 | | >267 |
| Ribavirin | Neutral Red (Cytopathic effect/Toxicity) | 6.4 | | >320 | >50 | |

*SI$_{50}$ = CC$_{50}$/EC$_{50}$
**SI$_{90}$ = CC$_{50}$/EC$_{90}$

TABLE 13

In Vitro Antiviral Screen (Influenza A virus H1N1, California/07/2009)

| Compound No. | Drug Assay Name | EC$_{50}$ (μg/ml) | EC$_{90}$ (μg/ml) | CC$_{50}$ (μg/ml) | *SI$_{50}$ | **SI$_{90}$ |
|---|---|---|---|---|---|---|
| MD185 | Visual (Virus yield reduction/Neutral Red) | | 0.00026 | >0.32 | | >1230 |
| MD185 | Neutral Red (Cytopathic effect/Toxicity) | 0.00015 | | >0.32 | >2100 | |
| MD317 | Visual (Virus yield reduction/Neutral Red) | | 0.0017 | >0.32 | | >190 |
| MD317 | Neutral Red (Cytopathic effect/Toxicity) | 0.0009 | | >0.32 | >360 | |
| MD345 | Visual (Virus yield reduction/Neutral Red) | | 0.0047 | >0.32 | | >68 |
| MD345 | Neutral Red (Cytopathic effect/Toxicity) | 0.00077 | | >0.32 | >420 | |
| MD349 | Visual (Virus yield reduction/Neutral Red) | | 0.0046 | >0.32 | | >70 |
| MD349 | Neutral Red (Cytopathic effect/Toxicity) | 0.0007 | | >0.32 | >460 | |
| MD352 | Visual (Virus yield reduction/Neutral Red) | | 0.0041 | >0.32 | | >78 |

TABLE 13-continued

In Vitro Antiviral Screen (Influenza A virus H1N1, California/07/2009)

| Compound No. | Drug Assay Name | EC$_{50}$ (μg/ml) | EC$_{90}$ (μg/ml) | CC$_{50}$ (μg/ml) | *SI$_{50}$ | **SI$_{90}$ |
|---|---|---|---|---|---|---|
| MD352 | Neutral Red (Cytopathic effect/Toxicity) | 0.00025 | | >0.32 | >1300 | |
| Ribavirin | Visual (Virus yield reduction/Neutral Red) | | 2.3 | >320 | | >140 |
| Ribavirin | Neutral Red (Cytopathic effect/Toxicity) | 2.5 | | >320 | >130 | |

*SI$_{50}$ = CC$_{50}$/EC$_{50}$
**SI$_{90}$ = CC$_{50}$/EC$_{90}$

TABLE 14

In Vitro Antiviral Screen (Influenza A virus H5N1, Duck/MN/1525/81)

| Compound No. | Drug Assay Name | EC$_{50}$ (μg/ml) | EC$_{90}$ (μg/ml) | CC$_{50}$ (μg/ml) | *SI$_{50}$ | **SI$_{90}$ |
|---|---|---|---|---|---|---|
| MD185 | Visual (Virus yield reduction/Neutral Red) | | 0.00153 | >0.32 | | >210 |
| MD185 | Neutral Red (Cytopathic effect/Toxicity) | 0.00033 | | >0.32 | >970 | |
| MD317 | Visual (Virus yield reduction/Neutral Red) | | 0.00096 | >0.32 | | >330 |
| MD317 | Neutral Red (Cytopathic effect/Toxicity) | 0.00099 | | >0.32 | >320 | |
| MD345 | Visual (Virus yield reduction/Neutral Red) | | 0.0065 | >0.32 | | >49 |
| MD345 | Neutral Red (Cytopathic effect/Toxicity) | 0.0018 | | >0.32 | >180 | |
| MD349 | Visual (Virus yield reduction/Neutral Red) | | 0.00835 | >0.32 | | >38 |
| MD349 | Neutral Red (Cytopathic effect/Toxicity) | 0.00085 | | >0.32 | >380 | |
| MD352 | Visual (Virus yield reduction/Neutral Red) | | 0.0077 | >0.32 | | >42 |
| MD352 | Neutral Red (Cytopathic effect/Toxicity) | 0.00094 | | >0.32 | >340 | |
| Ribavirin | Visual (Virus yield reduction/Neutral Red) | | 2.3 | >320 | | >140 |
| Ribavirin | Neutral Red (Cytopathic effect/Toxicity) | 6.5 | | >320 | >49 | |

*SI$_{50}$ = CC$_{50}$/EC$_{50}$
**SI$_{90}$ = CC$_{50}$/EC$_{90}$

TABLE 15

In Vitro Antiviral Screen (Influenza A virus H5N1, Thailand/16/2004)

| Compound No. | Drug Assay Name | EC$_{50}$ (μg/ml) | EC$_{90}$ (μg/ml) | CC$_{50}$ (μg/ml) | *SI$_{50}$ | **SI$_{90}$ |
|---|---|---|---|---|---|---|
| MD185 | Visual (Virus yield reduction/Neutral Red) | | 0.012 | >2.0 | | >170 |
| MD185 | Neutral Red (Cytopathic effect/Toxicity) | 0.0045 | | >2.0 | >440 | |
| MD317 | Visual (Virus yield reduction/Neutral Red) | | 0.010 | >2.0 | | >200 |
| MD317 | Neutral Red (Cytopathic effect/Toxicity) | 0.0076 | | >2.0 | >260 | |
| MD345 | Visual (Virus yield reduction/Neutral Red) | | 0.005 | >2.0 | | >400 |
| MD345 | Neutral Red (Cytopathic effect/Toxicity) | 0.0069 | | >2.0 | >290 | |
| MD349 | Visual (Virus yield reduction/Neutral Red) | | 0.010 | >2.0 | | >200 |
| MD349 | Neutral Red (Cytopathic effect/Toxicity) | 0.0055 | | >2.0 | >360 | |
| MD352 | Visual (Virus yield reduction/Neutral Red) | | 0.002 | >2.0 | | >1000 |
| MD352 | Neutral Red (Cytopathic effect/Toxicity) | 0.0037 | | >2.0 | >540 | |
| Ribavirin | Visual (Virus yield reduction/Neutral Red) | | 2.79 | >320 | | >120 |
| Ribavirin | Neutral Red (Cytopathic effect/Toxicity) | 3.7 | | >320 | >86 | |

*SI$_{50}$ = CC$_{50}$/EC$_{50}$
**SI$_{90}$ = CC$_{50}$/EC$_{90}$

TABLE 16

In Vitro Antiviral Screen (Influenza A virus H1N1, A/Mississippi/3/2001 H275Y, Oseltamivir Resistant)

| Compound No. | Drug Assay Name | EC$_{50}$ (μg/ml) | EC$_{90}$ (μg/ml) | CC$_{50}$ (μg/ml) | *SI$_{50}$ | **SI$_{90}$ |
|---|---|---|---|---|---|---|
| MD185 | Visual (Virus yield reduction/Neutral Red) | 0.006 | | >2.0 | >330 | |
| MD185 | Neutral Red (Cytopathic effect/Toxicity) | 0.0062 | | >2.0 | >320 | |
| MD317 | Visual (Virus yield reduction/Neutral Red) | <0.002 | | >2.0 | >1000 | |
| MD317 | Neutral Red (Cytopathic effect/Toxicity) | <0.002 | | >2.0 | >1000 | |
| MD345 | Visual (Virus yield reduction/Neutral Red) | 0.0036 | | >2.0 | >560 | |
| MD345 | Neutral Red (Cytopathic effect/Toxicity) | 0.0036 | | >2.0 | >560 | |
| MD349 | Visual (Virus yield reduction/Neutral Red) | 0.0089 | | >2.0 | >220 | |
| MD349 | Neutral Red (Cytopathic effect/Toxicity) | 0.0067 | | >2.0 | >300 | |
| MD352 | Visual (Virus yield reduction/Neutral Red) | 0.008 | | >2.0 | >250 | |
| MD352 | Neutral Red (Cytopathic effect/Toxicity) | 0.0081 | | >2.0 | >250 | |

TABLE 16-continued

In Vitro Antiviral Screen (Influenza A virus H1N1,
A/Mississippi/3/2001 H275Y, Oseltamivir Resistant)

| Compound No. | Drug Assay Name | $EC_{50}$ (μg/ml) | $EC_{90}$ (μg/ml) | $CC_{50}$ (μg/ml) | *$SI_{50}$ | **$SI_{90}$ |
|---|---|---|---|---|---|---|
| Ribavirin | Visual (Virus yield reduction/Neutral Red) | 10 | | >320 | >32 | |
| Ribavirin | Neutral Red (Cytopathic effect/Toxicity) | 9.5 | | >320 | >34 | |

*$SI_{50} = CC_{50}/EC_{50}$
**$SI_{90} = CC_{50}/EC_{90}$

TABLE 17

In Vitro Antiviral Screen (Influenza A virus H5N1, Duck/MN/1525/81)

| Compound No. | Drug Assay Name | $EC_{50}$ (μg/ml) | $EC_{90}$ (μg/ml) | $CC_{50}$ (μg/ml) | *$SI_{50}$ | **$SI_{90}$ |
|---|---|---|---|---|---|---|
| MD185 | Visual (Virus yield reduction/Neutral Red) | <0.002 | | >2.0 | >1000 | |
| MD185 | Neutral Red (Cytopathic effect/Toxicity) | <0.002 | | >2.0 | >1000 | |
| MD317 | Visual (Virus yield reduction/Neutral Red) | <0.002 | | >2.0 | >1000 | |
| MD317 | Neutral Red (Cytopathic effect/Toxicity) | <0.002 | | >2.0 | >1000 | |
| MD345 | Visual (Virus yield reduction/Neutral Red) | 0.0042 | | >2.0 | >480 | |
| MD345 | Neutral Red (Cytopathic effect/Toxicity) | 0.0035 | | >2.0 | >570 | |
| MD349 | Visual (Virus yield reduction/Neutral Red) | <0.002 | | >2.0 | >1000 | |
| MD349 | Neutral Red (Cytopathic effect/Toxicity) | <0.002 | | >2.0 | >1000 | |
| MD352 | Visual (Virus yield reduction/Neutral Red) | 0.0023 | | >2.0 | >870 | |
| MD352 | Neutral Red (Cytopathic effect/Toxicity) | 0.0026 | | >2.0 | >770 | |
| Ribavirin | Visual (Virus yield reduction/Neutral Red) | 10 | | >320 | >32 | |
| Ribavirin | Neutral Red (Cytopathic effect/Toxicity) | 10 | | >320 | >32 | |

*$SI_{50} = CC_{50}/EC_{50}$
**$SI_{90} = CC_{50}/EC_{90}$

TABLE 18

In Vitro Antiviral Screen (Influenza B virus, B/Brisbane/60/2008)

| Compound No. | Drug Assay Name | $EC_{50}$ (μg/ml) | $EC_{90}$ (μg/ml) | $CC_{50}$ (μg/ml) | *$SI_{50}$ | **$SI_{90}$ |
|---|---|---|---|---|---|---|
| MD185 | Visual (Virus yield reduction/Neutral Red) | 0.006 | | >2.0 | >330 | |
| MD185 | Neutral Red (Cytopathic effect/Toxicity) | 0.0062 | | >2.0 | >320 | |
| MD317 | Visual (Virus yield reduction/Neutral Red) | <0.002 | | >2.0 | >1000 | |
| MD317 | Neutral Red (Cytopathic effect/Toxicity) | <0.002 | | >2.0 | >1000 | |
| MD345 | Visual (Virus yield reduction/Neutral Red) | 0.0036 | | >2.0 | >560 | |
| MD345 | Neutral Red (Cytopathic effect/Toxicity) | 0.0036 | | >2.0 | >560 | |
| MD349 | Visual (Virus yield reduction/Neutral Red) | 0.0089 | | >2.0 | >220 | |
| MD349 | Neutral Red (Cytopathic effect/Toxicity) | 0.0067 | | >2.0 | >300 | |
| MD352 | Visual (Virus yield reduction/Neutral Red) | 0.008 | | >2.0 | >250 | |
| MD352 | Neutral Red (Cytopathic effect/Toxicity) | 0.0081 | | >2.0 | >250 | |
| Ribavirin | Visual (Virus yield reduction/Neutral Red) | 10 | | >320 | >32 | |
| Ribavirin | Neutral Red (Cytopathic effect/Toxicity) | 9.5 | | >320 | >34 | |

*$SI_{50} = CC_{50}/EC_{50}$
**$SI_{90} = CC_{50}/EC_{90}$

TABLE 19

In Vitro Antiviral Screen (Influenza B virus, B/Florida/4/2006)

| Compound No. | Drug Assay Name | $EC_{50}$ (μg/ml) | $EC_{90}$ (μg/ml) | $CC_{50}$ (μg/ml) | *$SI_{50}$ | **$SI_{90}$ |
|---|---|---|---|---|---|---|
| MD185 | Visual (Virus yield reduction/Neutral Red) | 0.006 | | >2.0 | >330 | |
| MD185 | Neutral Red (Cytopathic effect/Toxicity) | 0.0062 | | >2.0 | >320 | |
| MD317 | Visual (Virus yield reduction/Neutral Red) | <0.002 | | >2.0 | >1000 | |
| MD317 | Neutral Red (Cytopathic effect/Toxicity) | <0.002 | | >2.0 | >1000 | |
| MD345 | Visual (Virus yield reduction/Neutral Red) | 0.0036 | | >2.0 | >560 | |
| MD345 | Neutral Red (Cytopathic effect/Toxicity) | 0.0036 | | >2.0 | >560 | |
| MD349 | Visual (Virus yield reduction/Neutral Red) | 0.0089 | | >2.0 | >220 | |
| MD349 | Neutral Red (Cytopathic effect/Toxicity) | 0.0067 | | >2.0 | >300 | |
| MD352 | Visual (Virus yield reduction/Neutral Red) | 0.008 | | >2.0 | >250 | |
| MD352 | Neutral Red (Cytopathic effect/Toxicity) | 0.008 | | >2.0 | >250 | |

TABLE 19-continued

In Vitro Antiviral Screen (Influenza B virus, B/Florida/4/2006)

| Compound No. | Drug Assay Name | $EC_{50}$ (μg/ml) | $EC_{90}$ (μg/ml) | $CC_{50}$ (μg/ml) | *$SI_{50}$ | **$SI_{90}$ |
|---|---|---|---|---|---|---|
| Ribavirin | Visual (Virus yield reduction/Neutral Red) | 10 | | >320 | >32 | |
| Ribavirin | Neutral Red (Cytopathic effect/Toxicity) | 9.5 | | >320 | >34 | |

*$SI_{50} = CC_{50}/EC_{50}$
**$SI_{90} = CC_{50}/EC_{90}$

TABLE 20

In Vitro Antiviral Screen (A/Sydney/250/99)

| Compound | $EC_{50}$ (ng/ml) | $EC_{50}$ (nM) |
|---|---|---|
| MD012 CHTCA(Z)$_2$(S$_6$) (MW 1534) | 0.06 | 0.039 |
| MD021 CHTCA(Z)$_2$-L-Asp (MW 1243) | 0.03 | 0.024 |
| Zanamivir (MW 332) | 7.38 | 22.228 |

TABLE 21

Anti influenza virus activity against Oseltamivir resistant strains
Inhibition of plaque size and plaque number by representative compounds of Formula (I)

| | | MD021 ng/ml | | MD051 ng/ml | | MD155 ng/ml | | MD185 ng/ml | | Oseltamivir nM | |
|---|---|---|---|---|---|---|---|---|---|---|---|
| Virus | Subtype | Size | Number | Size | Number | Size | Number | Size | Number | Size | Number |
| A/Fukui | H3N2 WT | 0.1-1.0$^a$ | 1-10 | 0.1-10 | 0.1-1 | 0.1-1.0 | 0.1-10$^b$ | 0.1-1.0 | 1 | 10-100 | ≥1000 |
| A/Fukui | H3N2 E119V | 0.1 | 0.1-1 | 0.1 | 0.1-1 | 0.1 | 0.1-1 | 0.1 | 0.1-1 | 100 | ≥10,000 |
| A/Perth | pH1N1 WT | 1 | 10-100 | 0.1-1.0 | 1-10 | 0.1-1.0 | 1-10 | 1 | 1-10 | 10 | 100 |
| A/Perth | pH1N1 H275Y | 0.1-1.0 | 10-100 | 0.1-1.0 | 1-10 | 0.1-1.0 | 1-10 | 0.1-1.0 | 1-100$^b$ | 100-1000 | ≥10,000 |
| B/Perth | B WT | 1 | 1-10 | 1 | 1-10 | 0.1-1.0 | 1-10 | 1.0-10 | 1-10 | 100-1000 | 1,000 |
| B/Perth | B D197E | 1 | 1-100 | 0.1-1.0 | 1-10$^b$ | 1.0-10 | 1-10 | 0.1-10 | 1-100 | 1000 | ≥10,000 |

$^a$A range is given when the $IC_{50}$ falls between two drug concentrations.
$^b$Range seen with duplicates may span more than one $log_{10}$ dilution.

TABLE 22

Viral Plaque Reduction Assay (CA/07/2009 virus H1N1)

| Compound | MW | $EC_{50}$ ng/ml | nM |
|---|---|---|---|
| MD185 | 1852 | 0.095 | 0.05140 |
| MD317 | 1318 | 0.068 | 0.05168 |
| MD343 | 1597 | 0.012 | 0.00749 |
| MD344 | 2057 | 0.021 | 0.01038 |
| MD345 | 2201 | 0.017 | 0.00797 |
| Zanamivir | 332 | 1.969 | 5.933 |

TABLE 23

Viral Plaque Reduction Assay (A/PR/8 virus H1N1)

| Compound | MW | $EC_{50}$ nM |
|---|---|---|
| MD185 | 1852 | 4.256 |
| MD344 | 2057 | 1.471 |
| MD342 | 2208 | 1.276 |
| MD345 | 2201 | 1.719 |
| MD348 | 1982 | 1.919 |
| MD051 | 1318 | 1.744 |
| MD343 | 1597 | 1.273 |
| MD317 | 1318 | 3.303 |
| Zanamivir | 332 | 10150 |

TABLE 24

In vivo mouse efficacy data for representative compounds of Formula (I)
Mice survivors/total after virus infection and compound treatment once at different dosages.

| | MD021 μg/mouse | | | MD154 μg/mouse | | | MD185 μg/mouse | | | Zanamivir μg/mouse | | |
|---|---|---|---|---|---|---|---|---|---|---|---|---|
| Virus infected in mice | 50 | 10 | 2 | 50 | 10 | 2 | 50 | 10 | 2 | 150 | 50 | Placebo |
| A/California/04/2009 (H1N1) | 8/10 | 3/10 | 5/10 | 10/10 | 10/10 | 4/10 | 10/10 | 9/10 | 4/10 | 2/10 | | 0/20 |
| A/Victoria/3/75 (H3N2) | 10/10 | 5/10 | 6/10 | | | | | | | 8/10 | 3/10 | 0/20 |
| A/Mississippi/3/01 H275Y | | | | 10/10 | 4/10 | 1/10 | 10/10 | 8/10 | 3/10 | 1/10 | | 0/20 |
| Oseltamivir resistant virus (H1N1) | 10/10 | 10/10 | 7/10 | 10/10 | 10/10 | 9/9 | 10/10 | 10/10 | 9/10 | 8/10 | | 0/20 |

TABLE 24-continued

In vivo mouse efficacy data for representative compounds of Formula (I)
Mice survivors/total after virus infection and compound treatment once at different dosages.

| Virus infected in mice | MD021 µg/mouse | | | MD154 µg/mouse | | | MD185 µg/mouse | | | Zanamivir µg/mouse | | Placebo |
|---|---|---|---|---|---|---|---|---|---|---|---|---|
| | 50 | 10 | 2 | 50 | 10 | 2 | 50 | 10 | 2 | 150 | 50 | |
| A/Duck/MN/1525/81 (H5N1) | 7/10 | 8/10 | 2/10 | 10/10 | 9/10 | 6/10 | 10/10 | 8/10 | 7/10 | 7/10 | | 3/20 |
| B/Sichuan/379/99 (FluB) | 8/10 | 8/10 | 7/10 | 10/10 | 10/10 | 9/10 | 9/10 | 9/10 | 9/10 | 8/10 | 9/10 | 1/20 |

Note:
Compounds were administered once intranasally 24 hours before infection; mice infected intranasally and observation period was 21 days.

TABLE 25

In vivo mouse efficacy data for representative compounds of Formula (I)
Mice survivors/total after virus infection and compound treatment once at different dosages and times.
Mice were infected intranasally by A/PR/8 virus (500 pfu/mouse) and treated intranasally with
representative compounds of Formula (I).

| | MD185 | MD342 | MD343 | MD344 | MD345 | MD348 | Zanamivir | placebo |
|---|---|---|---|---|---|---|---|---|
| 0.25 µg/mouse 24 hrs before infection | 4/5 | 5/5 | 4/5 | 4/5 | 5/5 | 4/5 | 0/5 | 0/5 |
| 0.5 µg/mouse 24 hrs before infection | 5/5 | 5/5 | 5/5 | 5/5 | 5/5 | 5/5 | 0/5 | 0/5 |
| 2 µg/mouse 5 days before infection | 5/5 | 5/5 | 5/5 | 5/5 | 5/5 | | 0/5 | 0/5 |
| 5 µg/mouse 7 days before infection | 5/5 | | 5/5 | 5/5 | 5/5 | | 0/5 | 0/5 |
| 5 µg/mouse 9 days before infection | 4/5 | 5/5 | 5/5 | 5/5 | 5/5 | 5/5 | 0/5 | 0/5 |
| 5 µg/mouse 11 days before infection | 4/5 | 5/5 | 4/5 | 2/5 | 5/5 | 5/5 | 0/5 | 0/5 |

TABLE 26

In vivo mouse efficacy data for representative compounds
of Formula (I)
Effects of intranasal treatment once with MD 185 and
Zanamivir when administered post-infection on survival
from an influenza A/California/04/2009 (H1N1pdm)
virus infection in mice.

| Compound | µg/mouse | Time of treatment (hours)$^a$ | Survivors/Total | Mean Day of Death$^b$ ± SD |
|---|---|---|---|---|
| MD185 | 250 | 24 | 4/10 | 8.2 ± 1.2*** |
| MD185 | 50 | 24 | 1/10 | 7.3 ± 0.5*** |
| MD185 | 10 | 24 | 0/10 | 6.3 ± 0.9 |
| Zanamivir | 250 | 24 | 0/9$^c$ | 6.7 ± 0.7 |
| Placebo | | 24 | 1/13$^c$ | 5.6 ± 0.9 |
| MD185 | 250 | 48 | 5/9$^{c**}$ | 6.5 ± 1.0 |
| MD185 | 50 | 48 | 3/10 | 7.7 ± 1.0 |
| MD185 | 10 | 48 | 1/10 | 7.6 ± 0.9* |
| Zanamivir | 250 | 48 | 0/10 | 6.6 ± 0.8 |
| Placebo | | 48 | 0/15 | 6.6 ± 0.6 |

$^a$Relative to virus exposure.
$^b$Of mice that died during the 21-day observation period.
$^c$Initial group sizes were 10 drug-treated and 15 placebo-treated mice. Four animals were excluded because they showed no evidence of infection (no weight loss).
*P < 0.05, P < 0.01, *P < 0.001, compared to placebo.

TABLE 27

In vivo mouse efficacy data for representative compounds of Formula (I)
Effects of intranasal treatment once with MD185, MD317, Zanamivir,
or saline when administered at 48 hrs post-infection
on survival from an influenzaA/PR/8 (H1N1) virus infection in mice.

| Compound | µg/mouse | Time of treatment (hours)$^a$ | Survivors/Total | Maximum mice weight loss$^b$ | | |
|---|---|---|---|---|---|---|
| MD185 | 40 | 48 | 5/5 | <10% 4/5; | 12% 1/5 | |
| MD317 | 40 | 48 | 4/5 | <10% 2/5; | 20% 2/5 | |
| Zanarnivir | 40 | 48 | 0/5 | | | |
| Placebo | Saline | 48 | 0/5 | | | |
| MD185 | 100 | 48 | 5/5 | <10% 4/5; | 17% 1/5 | |
| MD317 | 100 | 48 | 5/5 | <10% 3/5; | 15% 1/5; | 20% 1/5 |
| Zanamivir | 100 | 48 | 0/5 | | | |
| Placebo | Saline | 48 | 0/5 | | | |

$^a$Relative to virus exposure.
$^b$During the 21 days observation period.

TABLE 28

In vivo mouse efficacy data for representative compounds of Formula (I)
Effects of intranasal treatment once with MD185, MD345, MD348, Zanamivir,
or saline when administered at 48 hrs post-infection on survival from an
influenza A/PR/8 (H1N1) virus infection in mice.

| Compound | µg/mouse | Time of treatment (hours)[a] | Survivors/Total | Maximum mice weight loss[b] | | |
|---|---|---|---|---|---|---|
| MD185 | 40 | 48 | 5/5 | ≤5% 1/5; | ≤10% 1/5; | ≤15% 3/5 |
| MD345 | 40 | 48 | 5/5 | ≤10% 4/5; | ≤15% 1/5 | |
| MD348 | 40 | 48 | 5/5 | ≤5% 1/5; | ≤15% 3/5; | <25% 1/5 |
| Zanamivir | 40 | 48 | 0/5[c] | | | |
| Placebo | Saline | 48 | 0/5[d] | | | |

[a]Relative to virus exposure;
[b]During the 21 days observation period;
[c]Mean day of death: 6.9 days;
[d]Mean day of death: 6.6 days

TABLE 29

In vivo mouse efficacy data for representative compounds of Formula (I)
Effects of intranasal treatment once with MD185, MD348, Zanamivir,
or saline when administered at 48 hrs post-infection on survival from
an influenza A/PR/8 (H1N1) virus (500 pfu/mouse) infection in mice.

| Compound | µg/mouse | Time of treatment (hours)[a] | Survivors/Total | Maximum mice weight loss[b] | | |
|---|---|---|---|---|---|---|
| MD185 | 40 | 48 | 4/5 | 10% 1/5; | <15% 1/5; | 15% 2/5 |
| MD348 | 40 | 48 | 5/5 | ≤10% 3/5; | 15% 1/5; | 25% 1/5 |
| Zanamivir | 40 | 48 | 0/5 | | | |
| Placebo | Saline | 48 | 0/5 | | | |

[a]Relative to virus exposure;
[b]During the 21 days observation period.

TABLE 30

In vivo mouse efficacy data for representative compounds of Formula (I)
Effects of intranasal treatment once with MD185, Zanamivir, or saline when
administered at 60 hrs post-infection on survival from an influenza A/PR/8 (H1N1)
virus (500 pfu/mouse) infection in mice.

| Compound | µg/mouse | Time of treatment (hours)[a] | Survivors/Total | Maximum mice weight loss[b] | | |
|---|---|---|---|---|---|---|
| MD185 | 40 | 60 | 5/5 | ≤10% 3/5; | 12% 1/5; | 15% 1/5 |
| MD185 | 200 | 60 | 5/5 | <10% 2/5; | 12% 2/5; | 15% 1/5 |
| Zanamivir | 200 | 60 | 4/5[c] | 10% 1/5; | 15% 1/5; | ≥20% 2/5 |
| Placebo | Saline | 60 | 0/5[d] | | | |

[a]Relative to virus exposure;
[b]During the 21 days observation period;
[c]Mean day of death: 8 days;
[d]Mean day of death: 6.6 days

TABLE 31

In vivo mouse efficacy data for representative compounds of Formula (I)
Effects of intranasal treatment once with MD185, MD317, MD345, Zanamivir, or saline
when administered at 60 hrs post-infection on survival from an influenza A/PR/8 (H1N1)
virus (500 pfu/mouse) infection in mice.

| Compound | µg/mouse | Time of treatment (hours)[a] | Survivors/Total | Maximum mice weight loss[b] | | Mean day of death |
|---|---|---|---|---|---|---|
| MD185 | 40 | 60 | 2/5 | 20% 1/5; | 24% 1/5 | 7.3 days |
| MD317 | 40 | 60 | 2/5 | 20% 1/5; | 24% 1/5 | 7.0 days |
| MD345 | 40 | 60 | 5/5 | 18% 4/5; | 20% 1/5 | |
| Zanamivir | 2000 | 60 | 0/5 | | | 6.6 days |
| Zanamivir | 40 | 60 | 0/5 | | | 5.2 days |
| Placebo | Saline | 60 | 0/5 | | | 5.2 days |

[a]Relative to virus exposure;
[b]During the 21 days observation period.

TABLE 32

In vivo mouse efficacy data for representative compounds of Formula (I)
Effects of intranasal treatment once with MD185, Zanamivir, or saline when administered at 72 hrs
post-infection on survival from an influenza A/PR/8 (H1N1) virus (500 pfu/mouse) infection in mice.

| Compound | μg/mouse | Time of treatment (hours)[a] | Survivors/Total | Maximum mice weight loss[b] | | | Mean day of death |
|---|---|---|---|---|---|---|---|
| MD185 | 40 | 72 | 3/5 | ≤5% 1/5; | <15% 1/5; | <20% 1/5 | 7.25 days |
| MD185 | 200 | 72 | 4/5 | <10% 1/5; | <15% 2/5; | 20% 1/5 | 7.5 days |
| Zanamivir | 40 | 72 | 0/5 | | | | 5.8 days |
| Zanamivir | 200 | 72 | 0/5 | | | | 6.2 days |
| Placebo | Saline | 72 | 0/5 | | | | 5 days |

[a]Relative to virus exposure;
[b]During the 21 days observation period.

TABLE 33

In vivo mouse efficacy data for representative compounds of Formula (I)
Effects of intranasal treatment once with MD185, MD345, Zanamivir, or saline
when administered at 72 hrs post-infection on survival from an influenza A/PR/8 (H1N1)
virus (500 pfu/mouse) infection in mice.

| Compound | μg/mouse | Time of treatment (hours)[a] | Survivors/Total | Maximum mice weight loss[b] | | Mean day of death |
|---|---|---|---|---|---|---|
| MD185 | 40 | 72 | 6/10 | 20% 2/10; 12% 2/10 | 15% 1/10; 10/% 1/10 | 7.25 days |
| MD345 | 40 | 72 | 7/10 | 25% 1/10; 15% 3/10 | 18% 1/10; 12/% 2/10 | 7.0 days |
| Zanamivir | 40 | 72 | 0/5 | | | 6.6 days |
| Placebo | Saline | 72 | 0/5 | | | 6.6 days |

[a]Relative to virus exposure;
[b]During the 21 days observation period.

TABLE 34

In vivo mouse efficacy data for representative compounds of Formula (I)
Effects of intraperitoneal administration once with MD185, MD317, Zanamivir,
or saline, 1 hr before lethal challenge of influenza A/PR/8 (H1N1)
virus (500 pfu/mouse) on mice.

| Compound | μg/mouse | Time of treatment (hours)[a] | Survivors/Total | Maximum mice weight loss[b] | | |
|---|---|---|---|---|---|---|
| MD185 | 20 | −1 | 5/5 | 15% 3/5; | 18% 1/5; | 20% 1/5 |
| MD317 | 20 | −1 | 4/5 | 15% 3/5; | 24% 1/5 | |
| Zanamivir | 20 | −1 | 0/5[c] | | | |
| Placebo | Saline | −1 | 0/5[d] | | | |

[a]Relative to virus exposure;
[b]During the 21 days observation period;
[c]Mean day of death: 7 days;
[d]Mean day of death: 7 days

TABLE 35

In vivo mouse efficacy data for representative
compounds of Formula (I)
Effects of intraperitoneal administration 20 μg/mouse/day ×
5 days with MD185, MD317, Zanamivir, or saline at 4 hrs
post-infection on survival from an influenza A/PR/8 (H1N1)
virus (500pfu/mouse) infection in mice.

| Compound | μg/mouse/ day × 5 | Time of treatment (hours)[a] | Survivors/Total | Maximum mice weight loss[b] |
|---|---|---|---|---|
| MD185 | 20 × 5 | 4 | 5/5 | ≤10 |
| Zanamivir | 20 × 5 | 4 | 0/5[c] | |
| Placebo | Saline × 5 | 4 | 0/5[d] | |

[a]Relative to virus exposure;
[b]During the 21 days observation period;
[c]Mean day of death: 7.5 days;
[d]Mean day of death: 7.5 days.

TABLE 36

In vivo mouse efficacy data for representative compounds of Formula (I) Effects of intranasal treatment once with MD185, MD317, Zanamivir, or saline when administered at 60 hrs post-infection on survival from an influenza A/PR/8 (H1N1) virus (500 pfu/mouse) infection in mice.

| Compound | μg/mouse | Time of treatment (hours) | Survivors/Total | Maximum mice weight loss[b] | | Mean day of death |
|---|---|---|---|---|---|---|
| MD185 | 40 | 60 | 5/5 | 10% 4/5; | 20% 1/5 | |
| MD317 | 40 | 60 | 5/5 | 10% 3/5; | 24% 2/5 | |
| Zanamivir | 2000 | 60 | 3/5 | 15% 1/5 | 24% 2/5 | 8.5 days |
| Zanamivir | 40 | 60 | 0/5 | | | 7 days |
| Saline | N/A | 60 | 0/5 | | | 7 days |

[a]Relative to virus exposure,
[b]During the 21 days observation period

TABLE 37

In vivo mouse efficacy data for representative compounds of Formula (I) Effects of intranasal treatment once with MD345, MD356, MD357, MD358, MD359, Zanamivir, or saline when administered at 60 hrs post-infection on survival from an influenza A/PR/8 (H1N1) virus (500 pfu/mouse) infection in mice

| Compound | μg/mouse | Time of treatment (hours)[a] | Survivors/Total | Maximum mice weight loss[b] | | | Mean day of death |
|---|---|---|---|---|---|---|---|
| MD345 | 40 | 60 | 1/5 | 5% 1/5 | | | 7 days |
| MD356 | 40 | 60 | 5/5 | <10% 1/5 | <15% 3/5 | 25% 1/5 | |
| MD357 | 40 | 60 | 4/5 | <15% 3/5 | 20% 1/5 | | 7 days |
| MD358 | 40 | 60 | 5/5 | <10% 2/5 | 15% 3/5 | | |
| MD359 | 40 | 60 | 4/5 | <10% 1/5 | 17% 2/5 | 20% 1/5 | 7 days |
| Zanamivir | 40 | 60 | 0/5 | | | | 6 days |
| Saline | N/A | 60 | 0/5 | | | | 6 days |

[a]Relative to virus exposure.
[b]During the 21 days observation period.

TABLE 38

In vivo mouse efficacy data for representative compounds of Formula (I) Effects of intraperitoneal administration once with MD345, MD373, Zanamivir or saline, 1 hr before lethal challenge of influenza A/PR/8 (H1N1) virus

| Compound | Time of treatment (hours)[a] | Survivors/Total | Maximum mice weight loss[b] | | | |
|---|---|---|---|---|---|---|
| MD345 | −1 | 5/5 | 10% 1/5 | 12% 1/5 | 18% 1/5 | 22% 2/5 |
| MD373 | −1 | 5/5 | 10% 1/5 | 12% 1/5 | 20% 1/5 | 23% 2/5 |
| Zanamivir | −1 | 0/5[c] | | | | |
| Saline | −1 | 0/5[d] | | | | |

[a]Relative to virus exposure,
[b]During the 14 days observation period,
[c]Mean day of death 7 days,
[d]Mean day of death 5 days

TABLE 39

Anti-influenza virus activity in CPE assay for representative compounds of Formula (I) (EC50 ng/ml/nM)

| Flu virus | MD185 | MD356 | MD357 | MD358 | MD359 | MD371 | MD021 |
|---|---|---|---|---|---|---|---|
| A/Sydney/250/99 | 0.18/0.097 | 0.01/0.0054 | 0.02/0.0108 | 0.27/0.139 | 0.16/0.074 | n/a | 0.27/0.217 |
| A/Soloman Island/3/06 | 0.06/0.032 | 0.03/0.016 | 0.04/0.021 | 0.09/0.046 | 0.05/0.023 | n/a | 0.06/0.048 |
| A/Townsville/74/2011 | <0.03/<0.016 | 0.03/0.016 | 0.03/0.016 | 0.03/0.0154 | 0.01/0.0046 | n/a | 0.03/0.024 |
| A/Mississippi/03/01/WT | 0.08/0.043 | 0.06/0.032 | 0.06/0.032 | 0.185/0.095 | 0.06/0.0278 | 0.06/0.035 | 0.06/0.048 |
| A/Mississippi/03/01/H274Y | 0.18/0.097 | 0.06/0.032 | 0.133/0.086 | 0.03/0.0154 | 0.06/0.0278 | 0.02/0.0116 | 0.06/0.048 |
| A/Perth/261/2009 | 0.09/0.048 | n/a | n/a | 0.0065/0.0033 | 0.03/0.0139 | 0.009/0.0052 | 0.03/0.024 |
| A/Victoria/170/2012 | 0.27/0.145 | 0.27/0.145 | 1.20/0.647 | n/a | n/a | 0.27/0.157 | 0.27/0.217 |
| A/Sydney/5/97 | 0.13/0.070 | 0.06/0.032 | 0.18/0.097 | 0.09/0.046 | 0.16/0.074 | n/a | 0.27/0.217 |
| B/Townsville/2/2011 | 5.07/2.73 | 0.28/0.151 | 2.5/1.348 | 2.5/1.28 | 2.5/1.158 | n/a | 2.5/2.01 |

TABLE 40

Anti-influenza virus activity in CPE assay for representative compounds of Formula (I) at different viral titres ($EC_{50}$ ng/ml/nM)

| Flu virus | MD185 | MD356 | MD358 | MD359 | MD371 | MD345 | MD021 |
|---|---|---|---|---|---|---|---|
| A/Townsville/74/2011 ($1 \times 10^{-5}$/ml) | <0.03/<0.016 | 0.03/0.016 | 0.03/0.0154 | 0.01/0.0046 | n/a | 0.03/0.0136 | 0.03/0.24 |
| A/Townsville/74/2011 ($5 \times 10^{-5}$/ml) | 66/35.6 | 0.8/0.43 | 48/24.7 | 66/30.5 | 66/38.6 | 158/71.7 | No inhibition at 197 |

Example 8: ADME Toxicology for Representative Compounds of Formula (I)

Two compounds of Formula (I), MD185 and MD317, were tested in an hERG $IC_{50}$ (hERG-CHO, automated patch-clamp) assay. The $IC_{50}$ value of MD185 was not calculable. Concentration-response curve for MD317 showed less than 25% effect at the highest validated testing concentration, i.e. $IC_{50}$>100 nM.

Results indicated that MD185 and MD317 were safe on cardiac toxicity.

Example 9: KINOME Scan Profiling for Representative Compounds of Formula (I)

Two compounds of Formula (I), MD185 and MD317, were tested according to the following protocol for kinase assays.

For most assays, kinase-tagged T7 phage strains were grown in parallel in 24-well blocks in an *E. coli* host derived from the BL21 strain. *E. coli* were grown to log-phase and infected with T7 phase from a frozen stock (multiplicity of infection=0.4) and incubated with shaking at 32° C. until lysis (90-150 minutes). The lysates were centrifuged (6,000×g) and filtered (0.2 μm) to remove cell debris. The remaining kinases were produced in HEK-293 cells and subsequently tagged with DNA for qPCR detection. Streptavidin-coated magnetic beads were treated with biotinylated small molecule ligands for 30 minutes at room temperature to generate affinity resins for kinase assays. The liganded beads were blocked with excess biotin and washed with blocking buffer (SeaBlock(pierce), 1% BSA, 0.05% Tween20, 1 mMDTT) to remove unbound ligand and to reduce non-specific phage binding. Binding reactions were assembled by combining kinases, liganded affinity beads, and test compounds in 1× binding buffer (20% SeaBlock, 0.17×PBS, 0.05% Tween20, 6 mMDTT). Test compounds were prepared as 40× stocks in 100% DMSO and directly diluted into the assay. All reactions were performed in polypropylene 384-well plates in a final volume of 0.04 ml. The assay plates were incubated at room temperature with shaking for 1 hour and the affinity beads were washed with buffer (1×PBS, 0.05% Tween 20). The beads were then resuspended in elution buffer (1×PBS, 0.05% Tween 20, 0.5 μM non-biotinylated affinity ligand) and incubated at room temperature with shaking for 30 minutes. The kinase concentration in the eluates was measured by qPCR There were no significant interaction between compounds and kinases at 100 nM. Results are summarized in Table 41.

TABLE 41

Selectivity score table

| Compound Name | Selectivity Score Type | Number of Hits | Number of Non-Mutant Kinases | Screening Conc. (nM) | Selectivity Score |
|---|---|---|---|---|---|
| MD185 | S(35) | 0 | 395 | 100 | 0 |
| MD185 | S(10) | 0 | 395 | 100 | 0 |
| MD185 | S(1) | 0 | 395 | 100 | 0 |
| MD317 | S(35) | 0 | 395 | 100 | 0 |
| MD317 | S(10) | 0 | 395 | 100 | 0 |
| MD317 | S(1) | 0 | 395 | 100 | 0 |

Preparation of Representative Compounds of the Invention

For convenience, many chemical moieties are represented using well known abbreviations, including but not limited to, methyl (Me), ethyl (Et), n-propyl (nPr), isopropyl (iPr), n-butyl (nBu), tert-butyl (tBu), n-hexyl (nHex), cyclohexyl (cHex), phenyl (Ph), methoxy (MeO), ethoxy (EtO), trimethylsilyl (TMS), tert-butyloxycarbonyl (Boc), and acetyl (Ac).

For convenience, many chemical compounds are represented using well known abbreviations, including but not limited to, methanol (MeOH), ethanol (EtOH), diethyl ether (Et2O), ethyl acetate (EtOAc), triethylamine (TEA), dichloromethane (methylene chloride, DCM, $CH_2Cl_2$), trifluoroacetic acid (TFA), trifluoroethanol (TFE), dimethylformamide (DMF), sodium sulphate ($Na_2SO_4$), tetrahydrofuran (THF), meta-chloroperoxybenzoic acid (mCPBA), hexamethyldisilazane sodium salt (NaHMDS), O-(7-azabenzotriazol-1-yl)-N,N,N',N'-tetramethyluronium hexafluorophosphate (HATU), O-(benzotriazol-1-yl)-N,N,N',N'-bis(tetramethylene)uronium hexafluorophosphate (HBTU), dimethylsulfoxide (DMSO), magnesium sulphate ($MgSO_4$), sodium hydrogen carbonate ($NaHCO_3$), tert-butanol (t-BuOH), 1-ethyl-3-(3-dimethylaminopropyl) carbodiimide hydrochloride salt (EDCl.HCl), tetra-n-butylammonium fluoride (TBAF), N,N-diisopropylethylamine (DIPEA), tert-butyldimethylsilyl (TBDMS), 1-hydroxybenzotriazole (HOBt), trans-dichlorobis(triphenylphosphine)palladium(II) ($PdCl_2(PPh_3)_2$), tetrakis(triphenylphosphine)palladium(0) ($Pd(PPh_3)_4$) tris(dibenzylideneacetone) dipalladium(0) ($Pd_2(dba)_3$), tri-t-butyl phosphonium tetrafluoroborate (t-$Bu_3PH.BF_4$), 4,5-bis(diphenylphosphino)-9,9-dimethylxanthene (Xantphos), triphenylphosphine ($PPh_3$), diisopropyl azodicarboxylate (DIAD), pyridinium chlorochromate (PCC), borane dimethylsulfide (BMS), titanium isopropoxide ($TiOiPr_4$), sodium triacetoxyborohydride ($NaBH(OAc)_3$), sodium cyanoborohydride ($NaBH_3(CN)$), sodium borohydride ($NaBH_4$), ammonium chloride ($NH_4Cl$), chloroform ($CHCl_3$), manganese dioxide ($MnO_2$), potassium carbonate ($K_2CO_3$), 1,2-dichloroethane (DCE), sodium azide ($NaN_3$), sodium nitrite ($NaNO_2$) di-tert-butyl dicarbonate ($Boc_2O$), and S-Acetamidomethyl (Acm).

General synthesis of compounds of Formula (I) is summarised in Scheme 1 below:

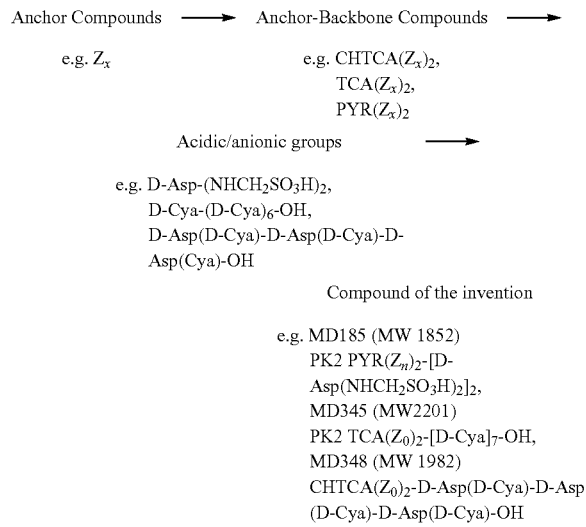

Scheme 1: General synthesis of compounds of Formula (I)

Anchor Compounds ⟶ Anchor-Backbone Compounds ⟶ e.g. $Z_x$      e.g. $CHTCA(Z_x)_2$,
                $TCA(Z_x)_2$,
                $PYR(Z_x)_2$

Acidic/anionic groups ⟶ e.g. D-Asp-(NHCH$_2$SO$_3$H)$_2$,
D-Cya-(D-Cya)$_6$-OH,
D-Asp(D-Cya)-D-Asp(D-Cya)-D-Asp(Cya)-OH

Compound of the invention e.g. MD185 (MW 1852)
PK2 PYR($Z_n$)$_2$-[D-Asp(NHCH$_2$SO$_3$H)$_2$]$_2$,
MD345 (MW2201)
PK2 TCA($Z_0$)$_2$-[D-Cya]$_7$-OH,
MD348 (MW 1982)
CHTCA($Z_0$)$_2$-D-Asp(D-Cya)-D-Asp(D-Cya)-D-Asp(D-Cya)-OH

Example 10: Preparation of N-Boc-1,9-diaminononane 1,9-Diaminononane (1 g, 6.329 mmoles) was dissolved in a mixture of 50 ml ethanol and 50 ml water, then was added di-t-butyldicarbonate (1.38 g, 6.329 mmoles) at R.T. The whole mixture was stirred at R.T. for 16 hrs to afford a white suspension. This suspension was filtered off. The solid was di-Boc-1,9-diaminononane 488 mg (1.36 mmoles, 21.53% yd.) after air dried. The filtrate was extracted with dichloromethane (150 ml, 100 ml). The aqueous layer containing unreacted 1,9-diaminononane (289 mg, 1.83 mmoles) can be recycled into next batch of preparation. The organic extracts were combined and washed with 50 ml of water, then stirred with 10 g anhydrous Na$_2$SO$_4$ at R.T. overnight. The organic suspension was filtered. The filtrate was vacuum evaporated into dryness to afford N-Boc-1,9-diaminononane 809 mg (49.5% yd.) as a colorless solid. MS 295 (M+1).

Example 11: Preparation of Anchoring Compound Zn'

Synthesis is detailed in Scheme 2 below. The following compound reference numbers and synthetic step references relate to Scheme 2.

Step A) Sialic acid (1) (5 g, 16.18 mmoles) and Dowex 50×8(H$^+$) resin (10 g) were stirred in anhydrous methanol (400 mL) at 60-62° C. for 48 hrs. The mixture was filtered off. The filtrate was vacuum evaporated to dryness to afford Compound (2) as a white solid 4.5 g (13.25 mmoles, 82.5% yd.). MS 338 (M+1).

Step B) Compound (2) (4 g, 11.87 mmoles) was stirred with acetic anhydride (40 mL, d 1.08, MW 102.29, 423 mmoles) and sulphuric acid (2 mL). The mixture was then stirred at 32-35° C. for 72 hr in an oil-bath. The reaction mixture was added dropwise to a stirring mixture of Na$_2$CO$_3$ (51 g) in water (280 mL) and ethyl acetate (14 mL) at an ice-bath. Afterwards, the mixture was stirred for additional 1.5 hr in an ice-bath, an subsequently extracted with ethyl acetate (400 mL, 270 mL). The ethyl acetate extracts were combined and washed with 10% NaHCO$_3$ solution (270 mL×2), saturated NaCl solution (270 mL×2), dried over anhydrous Na$_2$SO$_4$ overnight. Filtered off, the filtrate was vacuum evaporated to dryness to afford compound (3) 4.78 g (11.57 mmoles, 97.5% yd.). MS 414 (M+1). The oily residue turned into an off white solid after storage in a desiccator over P$_2$O$_5$ for 3 days.

Step C) Compound (3) (3.47 g, 8.4 mmoles) was dissolved in tert-BuOH (25 mL). To this solution was added azidotrimethylsilane (1.81 mL, 13.63 mmoles). The whole mixture was stirred at 80-82° C. under argon for 24 hrs. The reaction mixture was diluted with ethyl acetate (100 mL), then stirred with 0.9 g NaNO$_2$ in 25 mL of water, and adjusted to pH 2 with 5N HCl over a period of 1 hr at room temperature. The two phase mixture was separated, the aqueous layer was extracted with ethyl acetate (50 mL). The organic extracts were combined and washed successively with water (25 mL×2), 6% NaHCO$_3$ solution (25 mL), water (25 mL×3), then dried over Na$_2$SO$_4$. The filtrate was vacuum evaporated to dryness to afford Compound (4) 3.17 g (6.95 mmoles, 82.7% yd.) as an oily substance. MS 457 (M+1), 479 (M+Na), 925 (2M+Na).

Step D) Compound (4) (3.15 g, 6.91 mmoles) was dissolved in methanol (100 mL) and toluene (70 mL). The solution was placed under vacuum to remove air (oxygen), then backfilled with argon. To this mixture was added Pd/C (10%) (616 mg), then placed under vacuum to evacuate argon which was subsequently replaced with hydrogen (H$_2$). The hydrogenation was carried out at room temperature for 2 hr and the catalyst was subsequently filtered off. The filtrate was vacuum evaporated to dryness to afford compound (5) 2.82 g (6.55 mmoles, 94.7% yd.) as an off white solid. MS 431 (M+1).

Step E) Compound (5) (2.80 g, 6.51 mmoles) was dissolved in anhydrous acetonitrile (15 mL). To this solution was added N,N'-Di-Boc-1H-pyrazole-1-carboxamidine [Bis(Boc)PCH] (3.03 g, 9.76 mmoles). The whole mixture was stirred under argon at room temperature for 40 hr. The reaction mixture was vacuum evaporated to dryness. The residue was dissolved in ethyl acetate (4 mL), then diluted with hexane (4 mL), applied on flash column chromatography, washed with hexane (150 mL), then with solvent (ethyl acetate:hexane 1:1) (150 mL), finally eluted with solvent (ethyl acetate:hexane 1:1) Vacuum evaporation of the collected fractions gave the product Compound (6), 3.23 g (4.8 mmoles, 73.7% yd.) as a white solid. MS 673 (M+1).

Step F) Compound (6) (2.8715 g, 4.273 mmoles) was dissolved in anhydrous methanol (22 mL). To this solution was added NaOCH$_3$ (4.9134 mg, 0.2136 mmoles) under argon. The whole mixture was stirred under argon at R.T. for 2.5 hr, then adjusted to pH 6.5 with Dowex50×8(H$^+$) resin, which was subsequently filtered off. The filtrate was vacuum evaporated to dryness to give compound (7) 2.2024 g (4.0337 mmoles, 94.4% yd.) as a white solid. MS 547 (M+1).

Step G) Compound (7) (2 g, 3.66 mmoles) was dissolved in anhydrous acetonitrile. To this solution was added 1,1'-carbonyldiimidazole (714 mg, 4.403 mmoles). The whole mixture was stirred under argon at 20-30° C. for 18 hr. It was vacuum evaporated to dryness, then the residue was subjected to flash column chromatography, firstly washed with hexane (150 mL), then developed with solvent (ethyl acetate:hexane 2:1). The fractions at R$_f$ value of 0.5 (ethyl acetate:hexane 2:1) were combined and vacuum evaporated to dryness to afford Compound (8) 1.35 g (2.36 mmoles, 64.5% yd.) as a white solid. MS 573 (M+1).

Step H) Compound (8) (1.3 g, 2.27 mmoles) was dissolved in anhydrous pyridine (12.5 mL). To this solution were added p-nitrophenyl chloroformate (503.3 mg, 2.497 mmoles), 4-dimethylamino-pyridine (808.5 mg, 6.62 mmoles). The whole mixture was stirred at 30° C. under argon for 7 hr. To this reaction mixture was added a solution of N-Boc-1,9-diaminononane (690 mg, 2.67 mmoles) and 4-dimethylamino pyridine (166 mg, 1.36 mmoles) in anhydrous pyridine (4 mL). The reaction mixture was stirred under argon at 30° C. for 16 hr, then vacuum evaporated to remove pyridine. The residue was partitioned between ethyl acetate (300 mL) and water (50 mL) containing 2.45 mL of 5 NHCl, washed successively with water (50 mL×2), 2% NaHCO$_3$ solution (50 mL×6), water (50 mL×2), dried over anhydrous Na$_2$SO$_4$, and filtered. The filtrate was vacuum evaporated to dryness to give 2.25 g of an oily substance. It was subjected to flash column chromatography (ethyl acetate:hexane 1.5:1 as eluent). The fractions (at a Rf value of 0.27 TLC, ethyl acetate:hexane 1.5:1 as developing solvent) were combined and vacuum evaporated to dryness to afford compound (9) 1.057 g (1.234 mmole, 54.4% yd.) as a white solid. MS 857 (M+1), 879 (M+Na). $^1$H-NMR (DMSO-d$_6$) δ(ppm) 11.42 (1H, s, guanidine NHBoc), 8.25 (1H, d, NH-4), 7.95 (1H, H-3), 4.92 (2H, m, H-7, H-8), 4.75 (1H, m, H-4), 4.31-4.62 (4H, m, H-5, H-6, H-9, H-9), 3.74 (3H, s, COOCH$_3$), 2.90 (4H, m, NHCH$_2$(CH$_2$)$_7$CH$_2$NH), 1.86 (3H, s, NHCOCH$_3$), 1.49 (9H, s, Boc), 1.38 (18H, s, Boc), 1.2-1.6 (14H, m, NHCH$_2$(CH$_2$)$_7$CH$_2$NH).

Step I) Compound (9) (1 g, 1.168 mmoles) was dissolved in a mixture of trifluoro acetic acid (TFA) (36 ml) and methyl phenyl ether (Anisole) (3.9 ml) in dichloromethane (CH$_2$Cl$_2$) (36 ml). The whole mixture was stirred at 25° C. for 2 hr and 40 min, then it was vacuum evaporated at 35° C. for 2 hrs. The residue was stirred in hexane (100 ml) at R.T. overnight, the hexane was decanted and fresh hexane (60 ml) was added, and stirring was continued for 4 hrs at R.T. The hexane was then removed. The residue was dissolved in CH$_2$Cl$_2$ (10 ml) and evaporated to dryness at 35-40° C. The residue was dissolved in water (25 ml). The aqueous solution was freeze dried to afford compound (10) 1.026 g (1.143 mmoles, 97.8% yd.) as a white foam of TFA$_3$Z$_n'$ salt. MS 557 (M+1) [MW of Z$_n'$=556, TFA$_3$Z$_n'$=898].

Scheme 2: Preparation of Anchoring compound Zn'

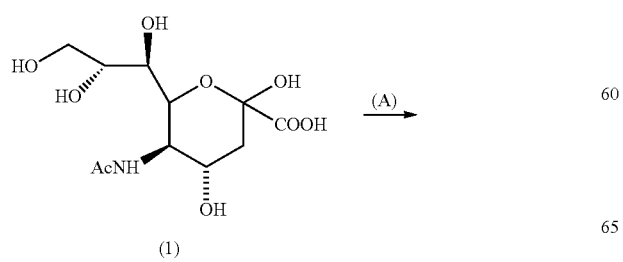

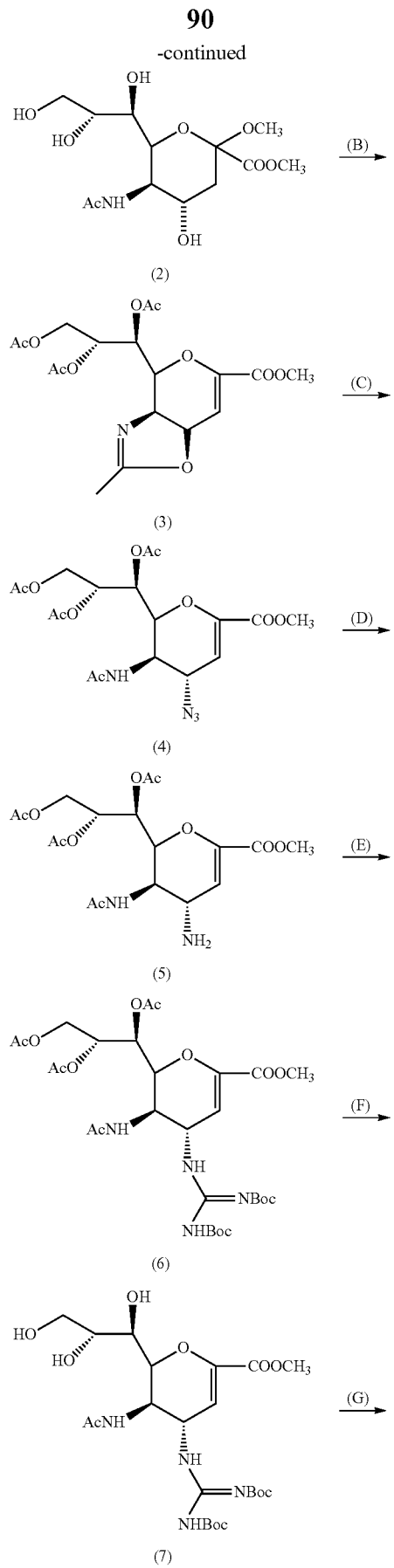

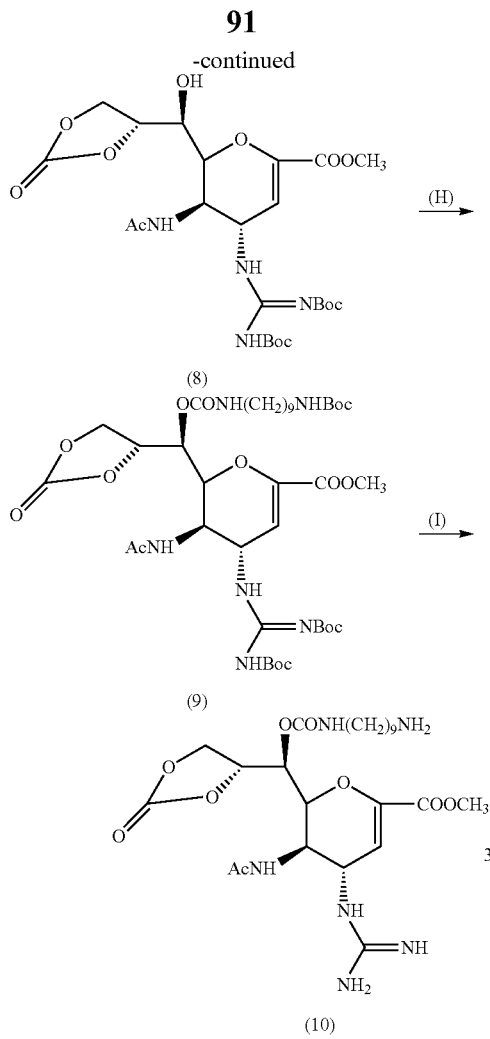

(8)

(9)

(10)

Example 12: Preparation of Anchor-Backbone Compounds PYR($Z_{n'}$)$_2$

Synthesis is detailed in Scheme 3 below. The following compound reference numbers relates to Scheme 3.

To a solution of pyromellitic dianhydride (11) (27.25 mg, 0.125 mmoles) in anhydrous DMF (2 ml) were added $Z_{n'}$ (10) (224.5 mg, 0.25 mmoles) and diisopropylethylamine (DIPEA) (130.64 μl, 0.75 mmoles) at room temperature. The whole reaction mixture was allowed to stir under argon at 25° C. for 36 hrs, then treated with ether:petroleum ether 1:1 (100 ml). The precipitate was filtered, washed with ether, and air dried to afford an off-white solid (197 mg), which was then subjected to HPLC separation and purification.

HPLC Analytical: Pep1 Gradient

Column: Gemini C18 column 100A 5 μm 150×3.00 mm. Wavelength: 220/280 nm. Flow rate: 0.7 ml/min. Solvent A=0.1% Trifluoroacetic acid. Solvent B=100% Acetonitrile. Temperature: 30° C. Gradient: 0-50% B, 15 minutes. Retention time: PK1PYR($Z_{n'}$)$_2$ (12) at 14.35 minutes, PK2PYR ($Z_{n'}$)$_2$ (13) at 14.53 minutes.

HPLC Preparative:

Column: Water Xterra C18 prep MS Column 19×50 mm, 5 μm. Wavelength: 220/280 nm. Flow rate: 8 ml/min. Solvent A=0.1% Trifluoroacetic acid. Solvent B=100% Acetonitrile. Temperature: 30° C. Gradient: 10-100% B, 80 minutes. Pure fractions of PK1PYR($Z_{n'}$)$_2$ and PK2PYR ($Z_{n'}$)$_2$ (13) were collected and freeze dried separately to afford PK1PYR($Z_{n'}$)$_2$ (12) 49 mg, and PK2PYR($Z_{n'}$)$_2$ (13) 42 mg, respectively.

PK1PYR($Z_{n'}$)$_2$ (12) MS indicated ESI +ve 10V 1331.5 ion. $^1$H-NMR (D$_2$O) δ (ppm): 8.00 (2H, s, aromatic para H×2), 6.00 (2H, d, H-3×2), 5.20-5.50 (4H, m, H-7×2, H-8×2), 4.35-4.90 (8H, m, H-4×2, H-5×2, H-6×2, H-9×2), 4.15 (2H, dd, H-9'×2), 3.80 (6H, s, COOCH$_3$×2), 3.25-3.45 (4H, m, OCONHCH$_2$×2), 2.90-3.20 (4H, m, NHCH$_2$×2), 1.95 (6H, s, CH$_3$CO×2), 1.20-1.70 (28H, m, (CH$_2$)$_7$×2).

PK2PYR($Z_{n'}$)$_2$ (13) MS indicated ESI +ve 10V 1331.5 ion. $^1$H-NMR (D$_2$O) δ (ppm) 8.35 (1H, s, aromatic H×1), 7.50 (1H, s, aromatic H×1), 6.00 (2H, d, H-3×2), 5.20-5.50 (4H, m, H-7×2, H-8×2), 4.35-4.90 (8H, m, H-4×2, H-5×2, H-6×2, H-9×2), 4.15 (2H, dd, H-9'×2), 3.80 (6H, s, COOCH$_3$×2), 3.25-3.45 (4H, m, OCONHCH$_2$×2), 2.90-3.20 (4H, m, NHCH$_2$×2), 1.95 (6H, CH$_3$CO×2), 1.20-1.70 (28H, m, (CH$_2$)$_7$×2).

Scheme 3: Preparation of Anchor-Backbone Compounds PYR($Z_{n'}$)$_2$

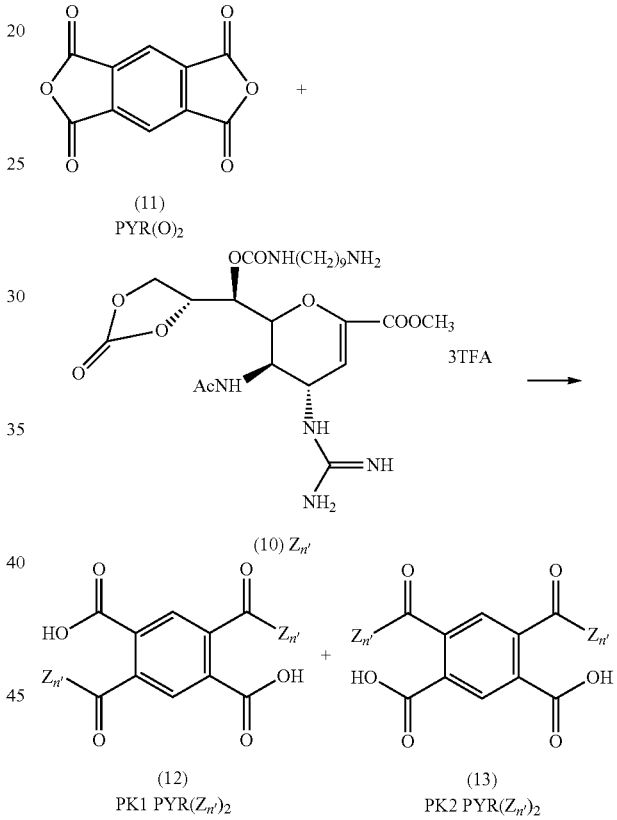

(11) PYR(O)$_2$

(10) $Z_{n'}$

(12) PK1 PYR($Z_{n'}$)$_2$

(13) PK2 PYR($Z_{n'}$)$_2$

Example 13: Preparation of Acidic/Anionic Group D-Asp(NHCH$_2$SO$_3$H)$_2$

Synthesis is detailed in Scheme 4 below. The following compound reference numbers relate to Scheme 4.

Boc-D-Aspatic acid (14) (233 mg, 1 mmole) and HBTU [O-(benzotriazol-1-yl)-N,N,N',N'-bis(tetramethylene)uronium hexafluorophosphate] (758 mg, 2 mmoles) were dissolved in DMF (10 ml). To this solution was added DIPEA (diisopropylethylamine) (349 μl, 2 mmoles). The solution was stirred at room temperature for 10 minutes, then combined with a solution of sodium aminomethanesulfonate (332 mg, 2.5 mmoles) in DMF (3 ml). The resulting solution was allowed to stir at room temperature overnight. The reaction mixture was vacuum evaporated to afford a pale orange solid. It was dissolved in water (20 ml), washed with ethyl acetate (20 ml×3), the aqueous phase was vacuum evaporated to remove organic solvent, then freeze dried to afford crude product (15) 310 mg as a white solid which was subjected to HPLC separation and purification.

HPLC Analytical: Pep1 Gradient

Column: Gemini C18 column 100A 5 μm 150×30 min. Wavelength: 220 nm. Flow rate: 0.7 ml/min. Solvent A=0.1% Trifluoroacetic acid. Solvent B=100% Acetonitrile. Temperature: 30° C. Gradient: 0-50% B, 15 minutes. Retention time: Compound (15) as free acid at 4.669 minutes MS ESI −ve 418 (M−1), solvent peak at 1.658 minutes, aminomethanesulfonic acid at 2.722 minutes, HBTU substance at 5.520 minutes, mono Boc-D-Asp-NHCH$_2$SO$_3$H at 5.802 minutes.

HPLC Preparative

Column: Germini AXIA C18 column, 5 μm 50×21.2 mm Wavelength: 220 min. Flow rate: 8 ml/min; Solvent A=0.1% Trifluoroacetic acid; Solvent B=100% Acetonitrile; Temperature: 30° C. Gradient: 0-100° % B, 100 minutes.

Fraction containing (15) were collected and pooled together, then freeze dried to afford pure product (15) as free acid. MS ESI −ve 418 (M−1). Compound (15) as free acid (200 mg, 0.477 mmoles) was dissolved in trifluoroacetic acid (10 ml) containing Anisole (1 ml). The solution was stirred at room temperature for one hour, then was vacuum evaporated to dryness. The residue was triturated in ether (20 ml×2), filtered off. The solid was air dried, then redissolved in water, freeze dried to afford product (16) 106 mg as a white solid. MS ESI −ve 318 (M−1). The product was dissolved in water (10 ml), then neutralized with two equivalent of sodium hydroxide, freeze dried to give disodium salt of (16) as a white solid.

Scheme 4: Preparation of Acidic/Anionic Group D-Asp(NHCH$_2$SO$_3$H)$_2$

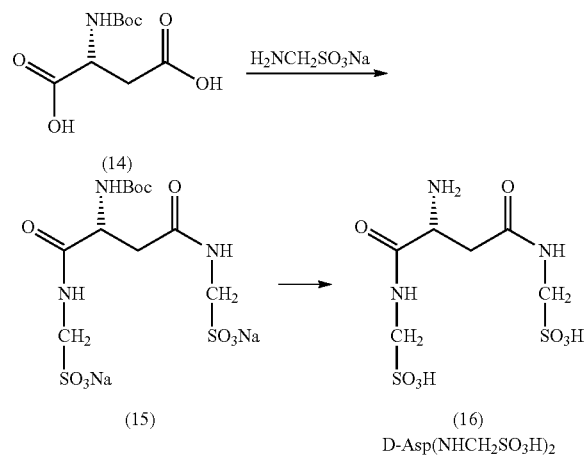

Example 14: Preparation of Compound MD185, PK2PYR(Z$_n$)$_2$[(D-Asp)(NHCH$_2$SO$_3$)$_2$]$_2$ Synthesis is detailed in Scheme 5 below. The following compound reference numbers relate to Scheme 5.

To a solution of PK2PYR(Z$_{n'}$)$_2$ (13) (30 mg, 22.56 μmoles) in dry DMF (5 ml) were added HATU [O-(7-Aza benzotriazol-1-yl)-N,N,N',N'-bis(tetramethylene)uronium hexafluorophosphate] (17.14 mg, 45.11 μmoles) and DIPEA (7.9 μl, 45.31 μmoles). The resulting solution was stirred at room temperature for 10 minutes, then was added disodium salt of (16) [D-Asp(NHCH$_2$SO$_3$Na)$_2$] (33 mg, 91.16 μmoles) in DMF (5 ml). The reaction mixture was stirred at room temperature for 18 hrs, then it was subjected to HPLC separation and purification.

HPLC Analytical: Pep 1 Gradient

Column: Gemini C18 column 100A 5 μm 150×3.00 mm; Wavelength: 220/280 nm; Flow rate: 0.7 ml/min; Solvent A=0.1% Trifluoroacetic acid; Solvent B=100% Acetonitrile; Temperature: 30° C.; Gradient: 0-50% B, 15 minutes; Retention time: The product (17) as free acid at 14.270 minutes. MS ESI +ve +30V 967.5. MS ESI −ve, −25 v 965.4. The other peaks were as follows: the starting material PK2PYR (Z$_{n'}$) (13) at 11.7 minutes, PK2PYR(Z$_{n'}$)$_2$-D-Asp (NHCH$_2$SO$_3$H)$_2$ at 13.6 minutes.

HPLC Preparative

Column: Water Xterra prep MS C18 column 19×50 mm 5 μm; Wavelength: 220/280 nm; Flow rate: 8 ml/min; Solvent A=0.1% Trifluoroacetic acid; Solvent B=100% Acetonitrile; Temperature: 30° C.; Gradient: 0-100% B 100 minutes Product elutes in reverse profile to Gemini analytical. Elution profile between 25-35% acetonitrile. Fractions sampled and tubes with greater than 90% purity were pooled and other material was separated on the Gemini AXIA column.

Product (17) was freeze dried to afford a white fluffy powder. MS ESI −ve −25 v 965.4, indicated the MW of 1932. Compound (17) PK2 PYR(Z$_{n'}$)$_2$[D-Asp (NHCH$_2$SO$_3$H)$_2$]$_2$ (8 mg, 4.14 μmoles) was dissolved in 50% methanol aqueous solution (2 ml), then added triethylamine (40 μl, 287.5 μmoles). The resulting solution was stirred at room temperature. Reaction was monitored by analytical HPLC for peak at 10.848 minutes. After 2 hrs, the reaction mixture was acidified with acetic acid (60 μl, 1049 μmoles) and diluted to 10 ml with water. The solution was purified on the Kinetex column. Pure fractions were combined and freeze dried to afford product (18) PK2 PYR(Z$_n$)$_2$ [D-Asp(NHCH$_2$SO$_3$H)$_2$]$_2$ 6 mg as white powder.

HPLC retention time 10.695 min. MS ESI −ve −30V 925.6.

In order to remove residue of TFA in compound, the pure material was dissolved in 60 ml 4 mM HCl and freeze dried, then dissolved in 60 ml 1mMHCl and freeze dried, finally freeze dried from 60 ml water. Yield. 5.6 mg (18) MD185 MW1852.

Scheme 5: Preparation of Compound MD185, PK2PYR(Z$_n$)$_2$[(D-Asp)(NHCH$_2$SO$_3$)$_2$]$_2$

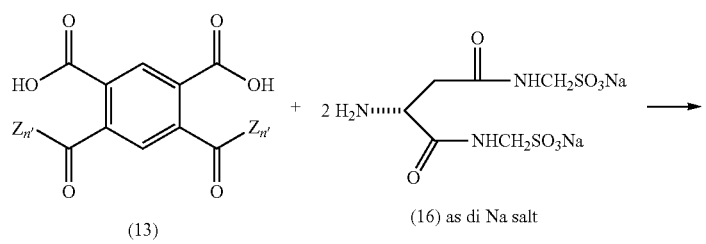

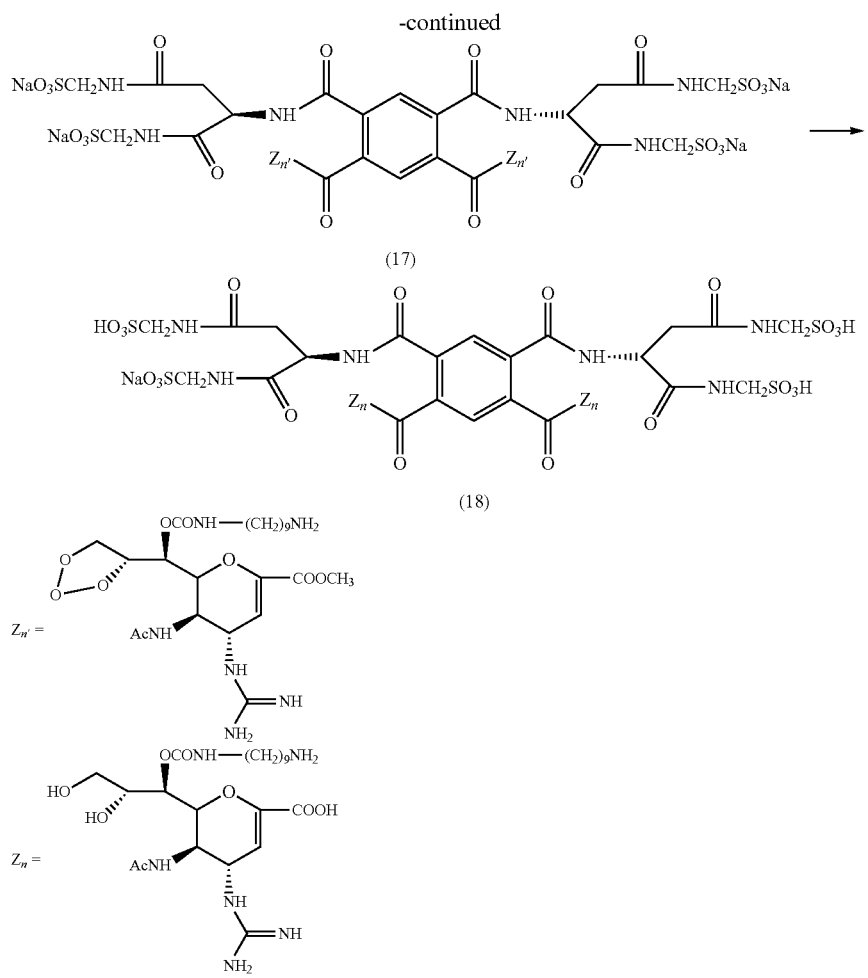

Example 15: Preparation of Anchor Compounds $Z_{0'}$

Synthesis is detailed in Scheme 6 below. Following compound reference numbers and synthetic step references relate to Scheme 6.

According to the procedure (H) and (I) described at Example 11, reaction of compound (8) with p-nitrophenyl chloroformate, then N-Boc-1,8-diaminooctane, after chromatography, afforded compound (19) as a white solid. MS 843 (M+1) Compound (19) was treated with trifluoroacetic acid (TFA), after work-up to give compound (20) $Z_{o'}$ as a white foam of $TFA_3Z_{0'}$ salt MS 543 (M+1) [MW of $Z_{o'}$=542, $TFA_3Z_{0'}$=884].

Scheme 6: Preparation of Anchor Compounds $Z_{0'}$

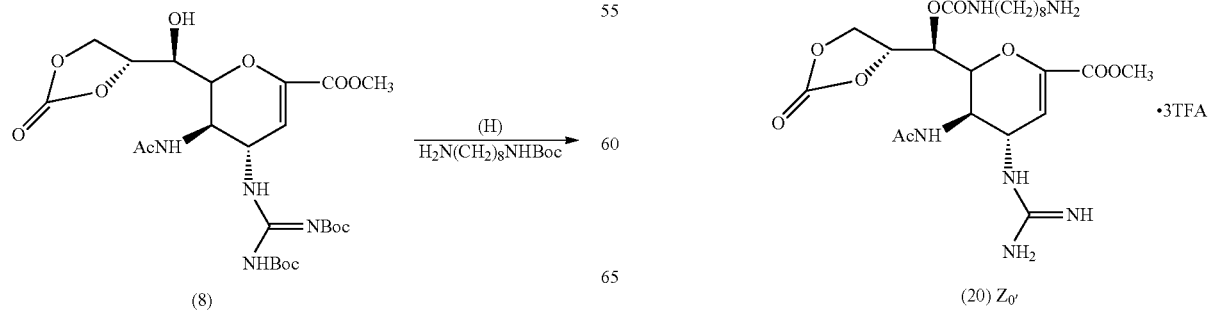

Example 16: Preparation of Anchor-Backbone Compounds PK1 TCA($Z_{0'}$)$_2$ and PK2 TCA($Z_{0'}$)$_2$ Synthesis is detailed in Scheme 7 below. The following compound reference numbers relate to Scheme 7.

To a solution of TCA (21) (3.085 mg, 17.52 µmoles) in DMF (309 µl) were added HATU (13.32 mg, 35.03 µmoles) and DIPEA (6.5 µl, 37.32 µmoles). The whole mixture was stirred at room temperature for 10 minutes, then was added dropwise a solution of $Z_{o'}$, (20) (30.97 mg, 35.03 µmoles) and DIPEA (18.44 µl, 105.9 µmoles) in DMF (600 µl). The reaction mixture was allowed to stir overnight at room temperature. The resulting mixture was subjected to HPLC separation and purification.

HPLC Analytical: Pep1 Gradient

Column: Phenomenex C18 5 µl 110A 150×3 mm Wavelength: 220/280 nm; Flow rate: 0.7 ml/min; Solvent A=0.1% Trifluoroacetic acid; Solvent B=100% Acetonitrile; Temperature: 30° C.; Gradient: 100-50% B 15 minutes Retention time: PK1 TCA($Z_{o'}$)$_2$ (22) 11.100 min and PK2 TCA($Z_{o'}$)$_2$ (23) 11.156 min.

PK1 TCA($Z_{o'}$)$_2$ (22) $^1$H-NMR (D$_2$O) δ ppm at 2.5 ppm (AB symmetric dd, 4H, $C_aH_2=C_bH_2$) indicated its symmetric structure. MS 1225.4 (MW 1224).

PK2 TCA($Z_{o'}$)$_2$ (23) $^1$H-NMR (D$_2$O) δ ppm at 2.35-2.75 ppm (asymmetric, dd, 4H, $C_aH_2 \neq C_bH_2$) indicated its asymmetric structure. MS 1225.4 (MW 1224).

Preparative HPLC

The solution was acidified with a small amount of 1M acetic acid and diluted to 25 ml in water. This was filtered through 0.45 µm syringe filter and pumped onto a Water Xterra prep MS C18 column 19×50 mm at 20% to 80% buffer A. Flow rate 8 ml/min gradient 0-100% B 100 minutes, wavelength 210/280 nm. Elution Profile Void DMF/DIPEA/HATU The PK1 TCA($Z_{o'}$)$_2$ and PK2 TCA($Z_{o'}$)$_2$ were further purified and separated on the Phenomenex Gemini 5 µm C18 110A Axia 50×21.2 mm column in 0.1% TFA buffer.

PK1/PK2 ratio is about 1:2, both MS ESI +30V 1225.4.

Scheme 7: Preparation of Anchor-Backbone Compounds PK1 TCA($Z_{0'}$)$_2$ and PK2 TCA($Z_{0'}$)$_2$

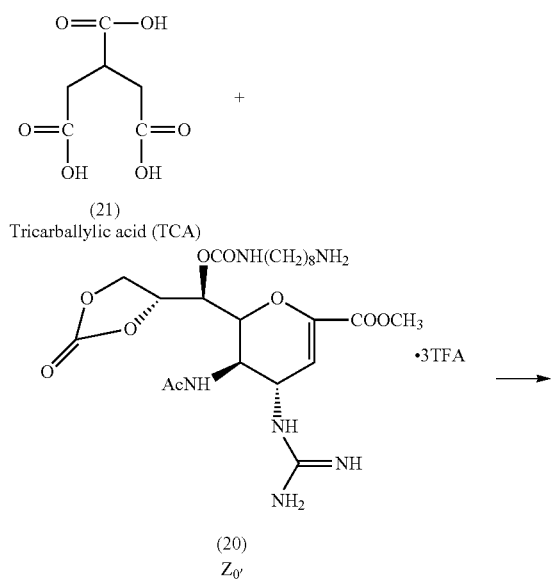

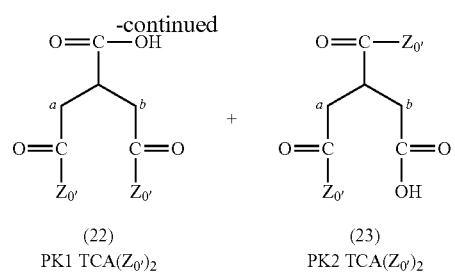

(22)
PK1 TCA($Z_{0'}$)$_2$

(23)
PK2 TCA($Z_{0'}$)$_2$

Example 17: Preparation of Acidic Anionic Group [D-Cya-SO$_3$H]$_7$OH

Synthesis is detailed in Scheme 8 below. The following compound reference numbers relate to Scheme 8.

As detailed in Scheme 8, solid phase synthesis was applied to prepare [D-Cys-SH]$_7$—OH (33), then oxidation of the polycysteine (33) provided [D-CyaSO$_3$H]$_7$—OH (34).

Fmoc-D-Cys(Trt)-OH (24) (2.93 g, 5 mmoles) was dissolved in dry dichloromethane (DCM) (35 ml) in a 50 ml Falcon tube, then was added 2-chlorotrityl chloride resin (25) (5 g), shaken vigorously, diisopropylethylamine (DIPEA) (3.5 ml, 20 mmoles) was added. After 5 min, another portion of DIPEA (1.3 ml, 7.5 mmoles) was added. The whole mixture was shaken for a further 4 hrs. To endcap any remaining reactive 2-chlorotrityl chloride, methanol was added (4 ml). The mixture was shaken for further 30 minutes. The resin was washed successively with DMF (20 ml×3). DCM (20 ml×3), methanol (20 ml×3), then vacuum dried overnight. Yield indicated loading of 0.57 mM/g (26).

For removal of Fmoc group from resin, the resin (26) was pre swollen in DCM (35 ml), then was added 50% piperidine in DMF (30 ml). The whole mixture was placed on a rotator for 30 min. This was repeated with a fresh solution of 50% piperidine in DMF (30 ml) for 60 min. Resin was then washed successively with DMF (20 ml×2), DCM (20 ml×2), DMF (20 ml×3). A positive ninhydrin test was presented. The resin (27) was ready for coupling.

To a solution of Fmoc-D-Cys(Trt)-OH (24) (1758 mg, 3 mmoles) in DMF (6 ml) were added HBTU [O-(Benzotriazol-1-yl)-N,N,N',N'-bis(tetramethylene)uronium hexafluorophosphate] (1140 mg, 3 mmoles) and DIPEA (523 µl, 3 mmoles). The mixture was stirred at room temperature for 10 minutes, then was added resin (27) (2.5 g, 0.57 mM/g, 1.5 mmoles). The reaction mixture was allowed to agitate for 24 hrs. Ninhydrin test negative, the resin was washed with DMF (20 ml×3), then treated with 5% acetic anhydride, 1% DIPEA in DMF (20 ml) for 30 minutes. The resin (28) was then washed with DMF (20 ml×3). DCM (20 ml×3), methanol (20 ml×3). The resin (28) was pre swollen in DCM, and was added 30% piperidine/N-methylpyrollidone in DMF (20 ml). The whole mixture was placed on a rotator for 30 minutes, then with fresh solution of 30% piperidine and N-methylpyrollidone for a further 60 minutes, after washing with DMF (20 ml×2), DCM (20 ml×2), DMF (20 ml×2) to afford resin (29).

The resin (29) was further coupled for 24 hrs. with (24) (1758 mg, 3 mmoles) in DMF (6 ml) preactivated for 10 minutes with HBTU (1140 mg, 3 mmoles) and DIPEA (523 µl, 3 mmoles), after work-up to afford resin (30). Half of which was then following the procedure: deprotected by piperidine/methylpyrollidone, recoupled with (24) preactivated with HBTU/DIPEA, to repeat this procedure for 4 times to produce resin (31).

Resin (31) was washed with DCM (20 ml×5), then was placed in a 50 ml Falcon tube, added 40% acetic acid in DCM (35 ml), on a rotator at room temperature was shaken for 6 hrs. The resin suspension was filtered, the filtrate was vacuum evaporated to a pale yellow foam. The residue was washed with water (100 ml×3), after dried to afford a white solid (32) [D-Cys(Trt)]$_7$-OH.

(32) was stirred in a solution of TFA (20 ml), Triisopropylsilane (1 ml) and water (0.5 ml) for 3 hrs. The resulting suspension was filtered. The filtrate was evaporated to an oily substance which was then triturated with ether (20 ml×4) to give a white solid. It was stirred in 50% acetonitrile aqueous solution (100 ml). The material was sonicated to form a white suspension, which was freeze dried to afford a crude product of (33) [D-Cys-SH]$_7$—OH (380 mg).

HPLC Analytical

Column: Phenomenex Gemini 5 μm C18 110A 150×3.00 mm Solvent A=0.1% Trifluoroacetic acid, Solvent B=100% Acetonitrile, Flow rate: 0.7 ml/min, Wavelength: 210/280 nm, Temperature: 30° C., Gradient: 0-50% B 15 minutes, Retention time: 9.356 minutes.

MS Cone +25V Major peak 740 Cone −25V Major peak 738 Indicated MW of (33) is 739 [D-Cys-SH]$_7$—OH Compound (33) (10 mg, 13.53 μmoles) was added to a performic acid solution (1 ml) prechilled in an ice-salt bath. The whole mixture was stirred in the ice bath for 1 hr, then diluted with 100 ml cold water, freeze dried to afford a pale yellow form (34). This material was purified on a Phenomenex Kinetex 5 μm XB-C18 100A column using isocratic 0.1% TFA as eluent to afford compound (34) [D-Cyst-SO$_3$H]$_7$—OH MW 1075, MS Cone +50V 1076 (M+1) as a colourless powder.

Performic acid was prepared by mixing Formic acid (8.74 ml), water (0.96 ml) and 30% hydrogen peroxide (1 ml), and allowing the mixture to stand at room temperature for 30 minutes in a stopped flask. This peroxide should be freshly made before use.

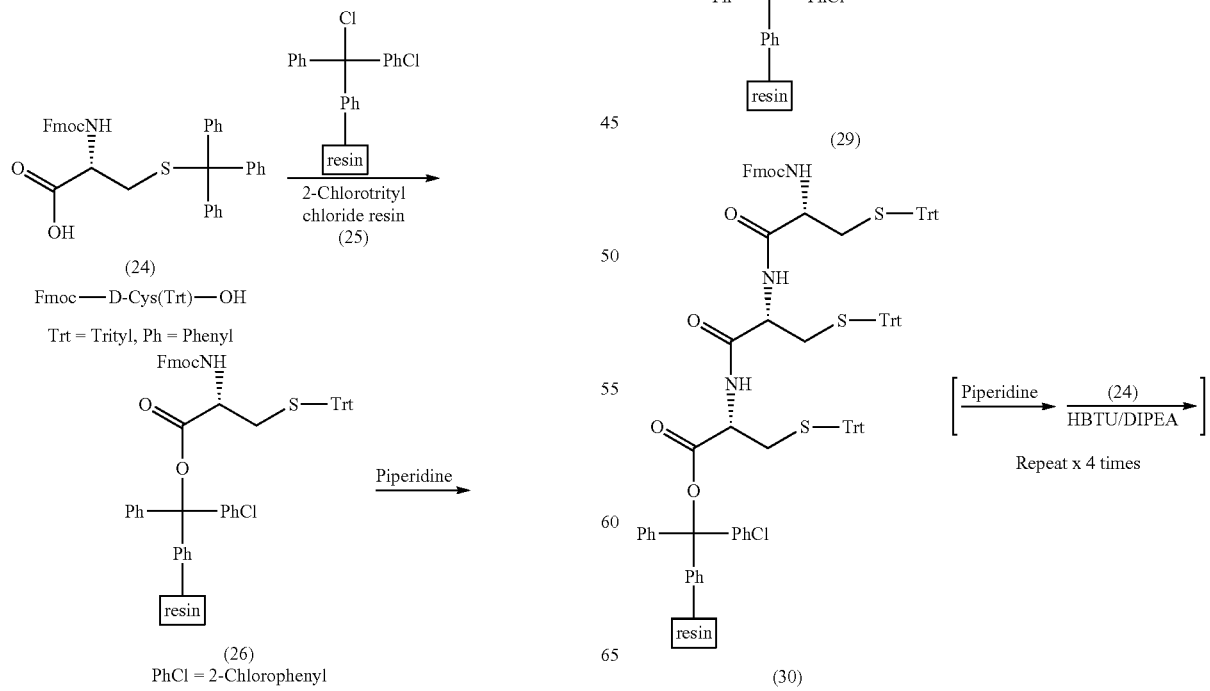

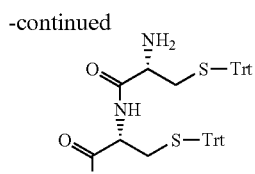

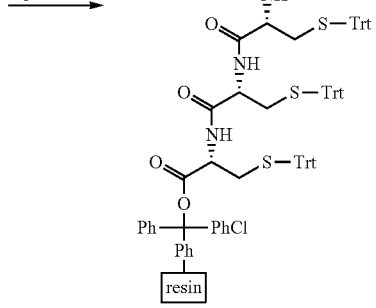

(31)

[D-Cys(Trt)]$_7$—OH $\xrightarrow{\text{TFA}}$ [D-Cys-SH]$_7$—OH $\xrightarrow{\text{HCOOOH}}$

(32)  (33)
MW 739

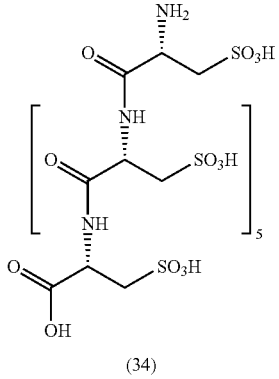

(34)
[D-Cyst-SO$_3$H]$_7$—OH
MW 1075

Example 18: Preparation of Compound MD345, PK2 TCA(Z$_0$)$_2$-[D-Cyst-SO$_3$H]$_7$—OH Synthesis is detailed in Scheme 9 below. The following compound reference numbers relate to Scheme 9.

To a solution of PK2 TCA(Z$_{0'}$)$_2$ (23) (4 mg, 3.268 moles) in anhydrous DMF (2 ml) were added HATU (1.242 mg, 3.268 μmoles) and 2% DIPEA in DMF (30 μl, 3.44 μmoles). The mixture was stirred at room temperature for 10 minutes, then combined with a solution of (34), [D-Cyst-SO$_3$H]$_7$—OH (7.03 mg, 6.54 moles) and DIPEA (9.11 μl, 52.32 μmoles), in DMF (3 ml). The whole reaction mixture was stirred at room temperature overnight. The mixture was diluted to 15 ml with water/methanol 1/1, then subjected to HPLC separation and purification.

HPLC Preparative:

Column: Phenomenex Kinetex 5 μm XB-C18 50×21.2 mm; Wavelength: 220/280 nm; Flow rate: 8 ml/min; Solvent A=0.1% Trifluoroacetic acid (TFA); Solvent B=100% Acetonitrile; Temperature: 30° C.; Gradient: 0-100% B, 80 minutes. Fractions containing (35) free acid (B═H) were combined and freeze dried to afford compound (35) free acid (B═H) 4 mg as a white powder. MS ESI +ve Cone 35V 1142.1 2+ion.

Compound (35) free acid (B═H), PK2 TCA(Z$_{0'}$)$_2$-[D-Cyst-SO$_3$H]$_7$—OH (4 mg, 1.754 μmoles) was dissolved in 50% methanol aqueous solution (800 μl) containing triethylamine (TEA) (20 μl, 146 μmoles). The mixture was stirred at room temperature, monitored by HPLC. It was worked up after 3 hrs. The solution was purified on the Kinetex column. Pure fractions at a retention time of 11.254 min were combined and freeze dried to afford compound (36) 2 mg as a white powder. MS ESI +ve Cone 40V 1102.2 2+ion.

In order to remove the residue of TFA in the compound, compound (36) was dissolved in 4 mM HCl (30 ml) and freeze dried. Then it was dissolved in 1 mM HCl (30 ml) and freeze dried. Finally it was freeze dried from water (30 ml) to afford product (36) 1.1 mg, MD345 PK2 TCA(Z$_0$)$_2$[D-Cyst-SO$_3$H]$_7$—OH MW2201 [MS 2202 (M+1)].

Scheme 9: Preparation of Compound MD345, PK2 TCA(Z$_0$)$_2$-[D-Cyst-SO$_3$H]$_7$-OH MW 2201

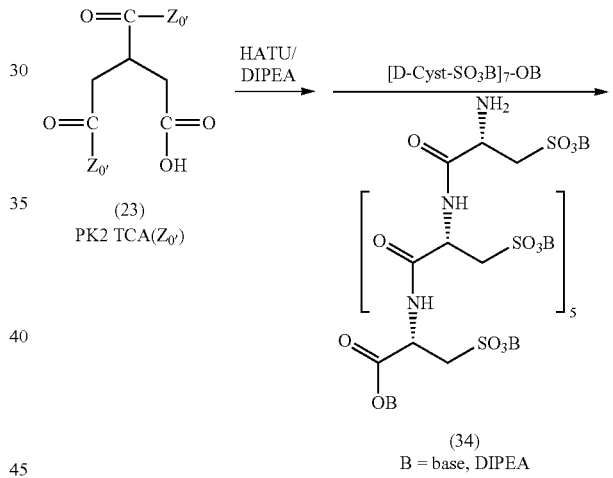

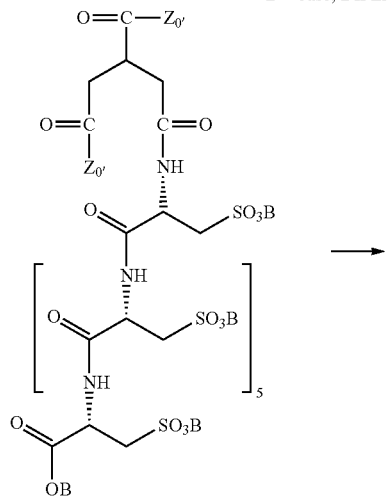

(35)
PK2 TCA(Z$_{0'}$)$_2$-[D-Cyst-So$_3$B]$_7$-OB

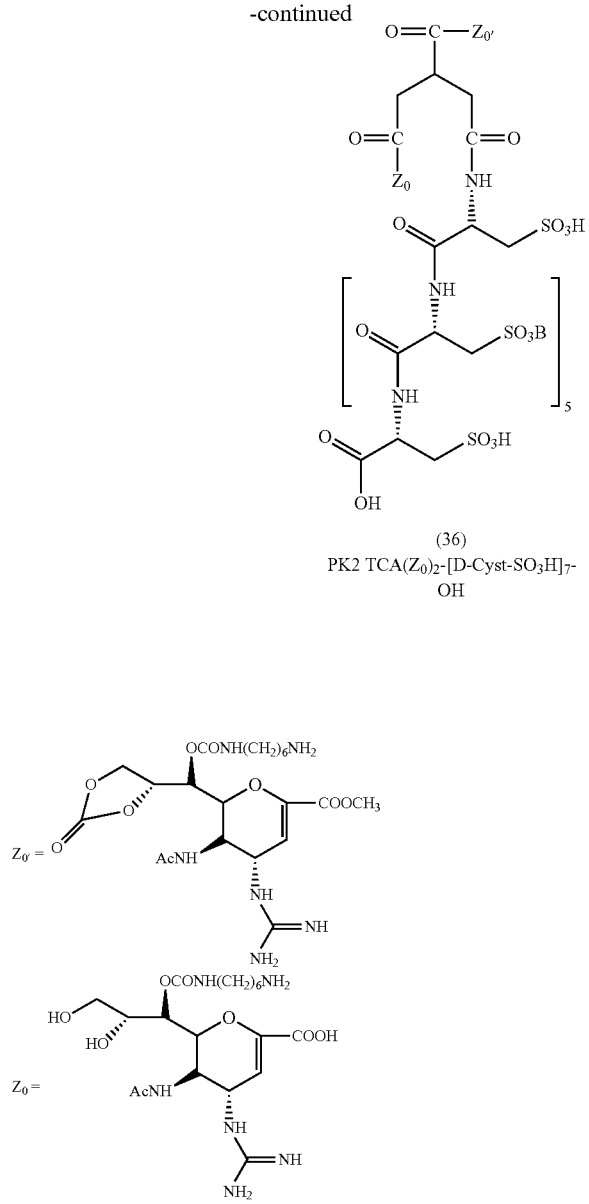

Example 19: Preparation of Anchor Compound Z'

Synthesis is detailed in Scheme 10 below. Following compound reference numbers and synthetic step references relate to Scheme 10.

According to the procedure (H) and (I) described in Example 11, reaction of compound (8) with p-nitrophenyl chloroformate, then N-Boc-1,6-diaminohexane, after chromatography, to afford compound (37) as a white solid, MS 815 (M+1). Compound (37) was treated with trifluoroacetic acid (TFA) and anisole, after work up to give compound (38) Z' as a white form of TFA salt. MS 515 (M+1). [MW of Z'=514. TFA$_3$Z'=856].

Scheme 10: Preparation of Anchor compound Z'

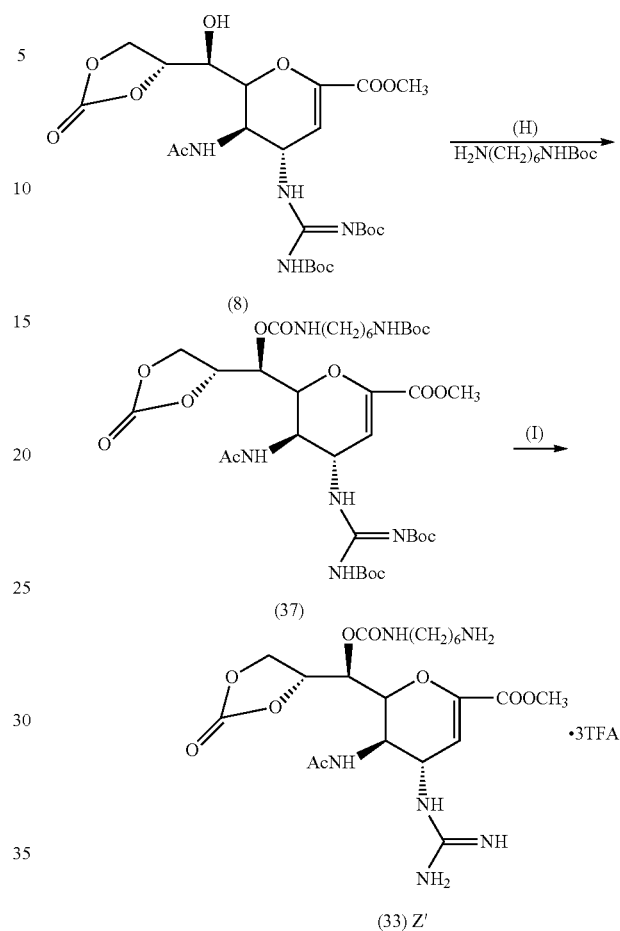

Example 20: Preparation of Anchor-Backbone Compound CHTCA(Z')$_2$

Synthesis is detailed in Scheme 11 below. Following compound reference numbers relate to Scheme 11.

To a solution of CHTCA(39) (4.4 mg, 20 μmoles) in DMF (300 μl) was added HATU (15.2 mg, 40 μmoles) and DIPEA (7.4 μl, 42.4 μmoles). The whole mixture was stirred at room temperature for 10 minutes, then was added dropwise a solution of Z' (38) (34.24 mg, 40 μmoles) and DIPEA (21.06 μl, 120.9 μmoles) in DMF (700 μl). The reaction mixture was allowed to stir overnight at room temperature. The resulting mixture was diluted with 1M HAc (50 μl) and water (25 ml). This was filtered through 0.45 μm syringe filter. The filtrate was subjected to HPLC separation and purification.

Column: Water Xterra prep MS C18 column 19×50 mm; Wavelength: 210/280 nm; Flow rate: 8 ml/min, Solvent A=0.1% TFA Solvent B=100% Acetonitrile; Temperature: 30° C.; Gradient: 0-100% B 100 minutes; Elution Profile Void DMF/DIPEA/HATU.

The fractions containing compound (40) were further purified on the Phenomenex Gemini 5 μm C18 110A AXIA 50×21.2 mm column in 0.1% TFA buffer. The fraction was freeze dried to afford compound (40) CHTCA(Z')$_2$, 15 mg as a white foam. MS ESI +ve, +30 v, 1209 indicated the MW of 1208.

Scheme 11: Preparation of Anchor-backbone compound CHTCA(Z')₂

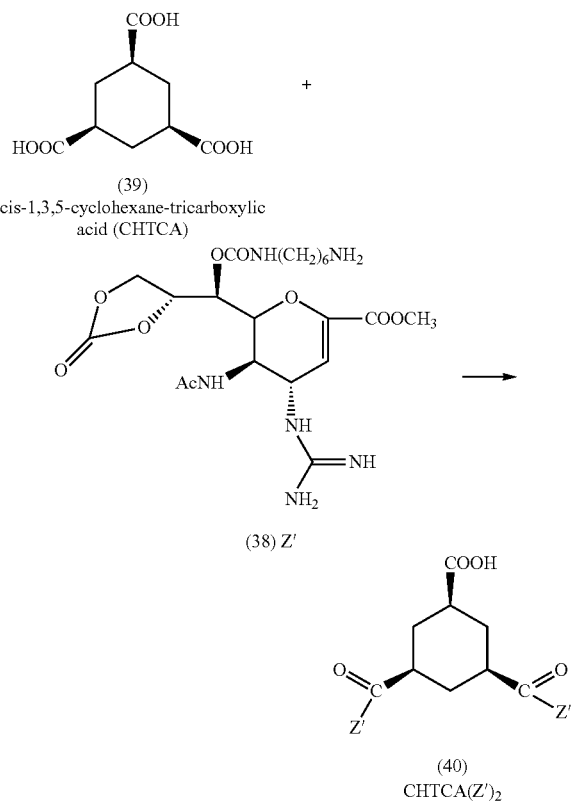

(39)
cis-1,3,5-cyclohexane-tricarboxylic acid (CHTCA)

(38) Z'

(40)
CHTCA(Z')₂

Example 20: Preparation of Anchor Compound S₆

Synthesis is detailed in Scheme 12 below. The following compound reference numbers and synthetic step references relate to Scheme 12.

Step A) Compound (1) was stirred in anhydrous methanol (100 ml) at room temperature for 48 hrs, the mixture was filtered off. The filtrate was vacuum evaporated to dryness to yield compound (41), 1.25 g (6.037 mmoles, 93% Yd.) as a white solid. MS 324 (M+1).

Step B) Compound (41) (1.95 g, 6.037 mmoles) was stirred in acetyl chloride (20 ml, 281 mmoles) at room temperature for 3 days, then vacuum evaporated to dryness to afford compound (42) 3.06 g (6.01 mmoles, 99% Yd.). MS 510.5 (M+1).

Step C) The residue (42) (3.06 g, 6.01 mmoles) was stirred in dichloromethane (DCM) (35 ml), then added KSAc (3.57 g, 31.26 mmoles). The reaction mixture was stirred under argon at room temperature for 40 hrs, diluted with dichloromethane (50 ml), then was partitioned between dichloromethane and water (50 ml). The organic layer was washed with 5% NaCl solution (22 ml×2), and dried over anhydrous Na₂SO₄ overnight, filtered off. The filtrate was evaporated to dryness to yield (43) 2.93 g (5.34 mmoles, 88.8% Yd.) as an off white foam. MS 550 (M+1).

Step D) Compound (43) (200 mg, 0.364 mmoles), and Boc-aminohexane bromide (107.4 mg, 0.385 mmoles) were stirred in DMF (2 ml), into which was added diethylamine (0.81 ml, 7.83 mmoles). The whole mixture was stirred under argon at 25° C. for 2.5 hrs. The reaction mixture was partitioned between ethyl acetate (EA) (80 ml) and saturated NaCl solution. The organic layer was washed with saturated NaCl solution (15 ml×3), water (10 ml×3). The organic layer was dried over Na₂SO₄, filtered, the filtrate was vacuum evaporated to dryness. The residue was subjected to silica gel column chromatography (Toluene:Acetone=2:1). The fractions containing compound (44) were combined and vacuum evaporated to dryness to afford compound (44) 98 mg (0.139 mmoles, 38% Yd.) as a white foam. MS 706 (M+1).

Step E) Compound (44) (95 mg, 0.135 mmoles) was dissolved in anhydrous methanol (1 ml). To this solution was added sodium methoxide (0.16 mg, 6.94 µmoles) under argon, the reaction mixture was stirred at room temperature for 2.5 hrs, then was adjusted with Dowex50×8(H⁺) resin to pH 6.0-6.5, filtered off. The filtrate was evaporated under vacuum to dryness to afford compound (45) 71 mg (0.132 mmoles, 97.9% Yd.) as a white foam. MS 538 (M+1)

Step F) Compound (45) (60 mg, 0.109 mmoles) was stirred under argon in 0.2N NaOH (2 ml, 0.4 mmoles) at room temperature for 2.5 hrs. The solution was adjusted to pH 3-4 with Dowex50×8(H⁺) resin and filtered off. The filtrate was freeze dried to afford compound (46) 56 mg (0.107 mmoles, 98% Yd.) as a white foam. MS 524 (M+1).

Step G) Compound (46) (50 mg, 0.0956 mmoles) was dissolved in a mixture of trifluoroacetic acid (TFA) (2 ml, 25.96 mmoles) and methylphenylether (anisole) (0.2 ml, 1.84 mmoles) in dichloromethane (2 ml). The whole mixture was stirred at 25° C. for 2.5 hrs, then it was vacuum evaporated at 35° C. for 2 hrs. The residue was washed in hexane (10 ml×2) at room temperature overnight, the hexane was decanted. The residue was stirred in ether (10 ml×2) at room temperature, then ether was removed. The residue was dissolved in water (1 ml), and freeze dried to afford compound (47), as a white foam of S₆.TFA salt, 51 mg (0.0949 mmoles, 99% Yd.). MS 424 (M+1) [The MW of S₆=423, S₆.TFA salt=537].

Scheme 12: Preparation of Anchor compound S₆

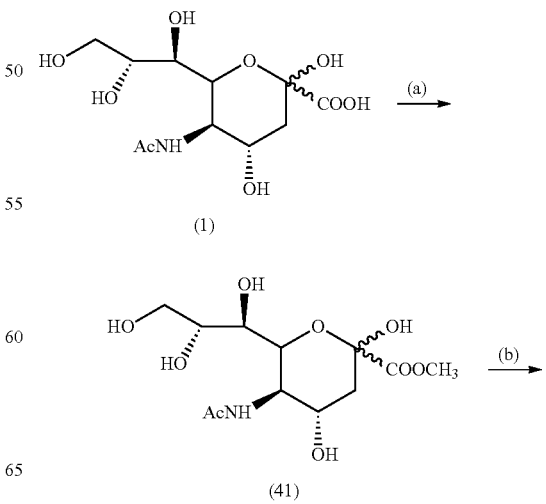

(1)

(41)

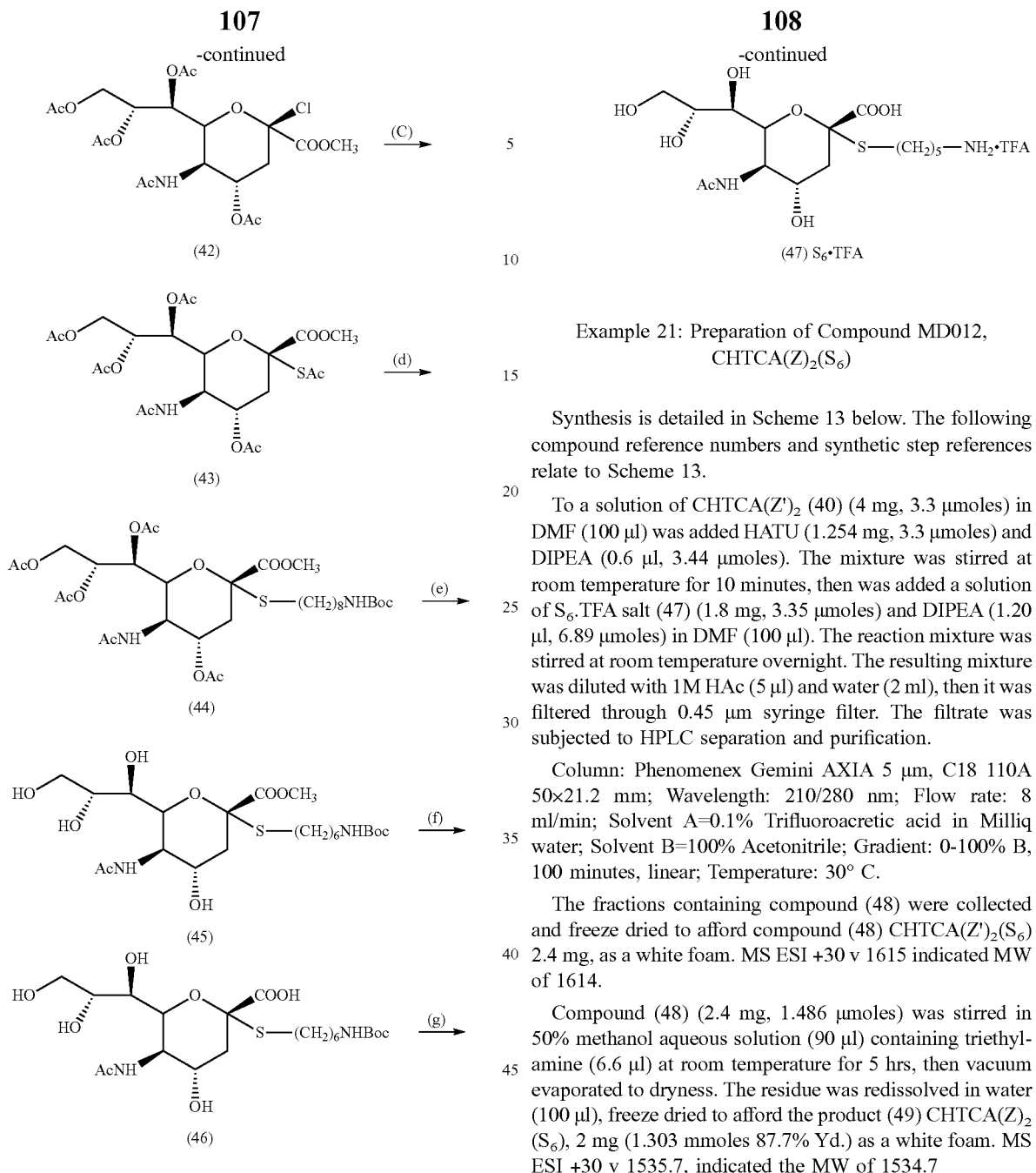

Example 21: Preparation of Compound MD012, CHTCA(Z)₂(S₆)

Synthesis is detailed in Scheme 13 below. The following compound reference numbers and synthetic step references relate to Scheme 13.

To a solution of CHTCA(Z')₂ (40) (4 mg, 3.3 μmoles) in DMF (100 μl) was added HATU (1.254 mg, 3.3 μmoles) and DIPEA (0.6 μl, 3.44 μmoles). The mixture was stirred at room temperature for 10 minutes, then was added a solution of S₆.TFA salt (47) (1.8 mg, 3.35 μmoles) and DIPEA (1.20 μl, 6.89 μmoles) in DMF (100 μl). The reaction mixture was stirred at room temperature overnight. The resulting mixture was diluted with 1M HAc (5 μl) and water (2 ml), then it was filtered through 0.45 μm syringe filter. The filtrate was subjected to HPLC separation and purification.

Column: Phenomenex Gemini AXIA 5 μm, C18 110A 50×21.2 mm; Wavelength: 210/280 nm; Flow rate: 8 ml/min; Solvent A=0.1% Trifluoroacretic acid in Milliq water; Solvent B=100% Acetonitrile; Gradient: 0-100% B, 100 minutes, linear; Temperature: 30° C.

The fractions containing compound (48) were collected and freeze dried to afford compound (48) CHTCA(Z')₂(S₆) 2.4 mg, as a white foam. MS ESI +30 v 1615 indicated MW of 1614.

Compound (48) (2.4 mg, 1.486 μmoles) was stirred in 50% methanol aqueous solution (90 μl) containing triethylamine (6.6 μl) at room temperature for 5 hrs, then vacuum evaporated to dryness. The residue was redissolved in water (100 μl), freeze dried to afford the product (49) CHTCA(Z)₂(S₆), 2 mg (1.303 mmoles 87.7% Yd.) as a white foam. MS ESI +30 v 1535.7, indicated the MW of 1534.7

Scheme 13: Preparation of Compound MD012, CHTCA(Z)₂(S₆)

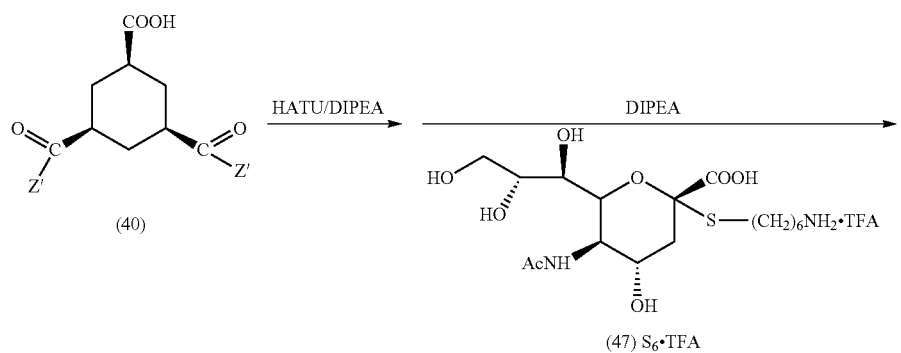

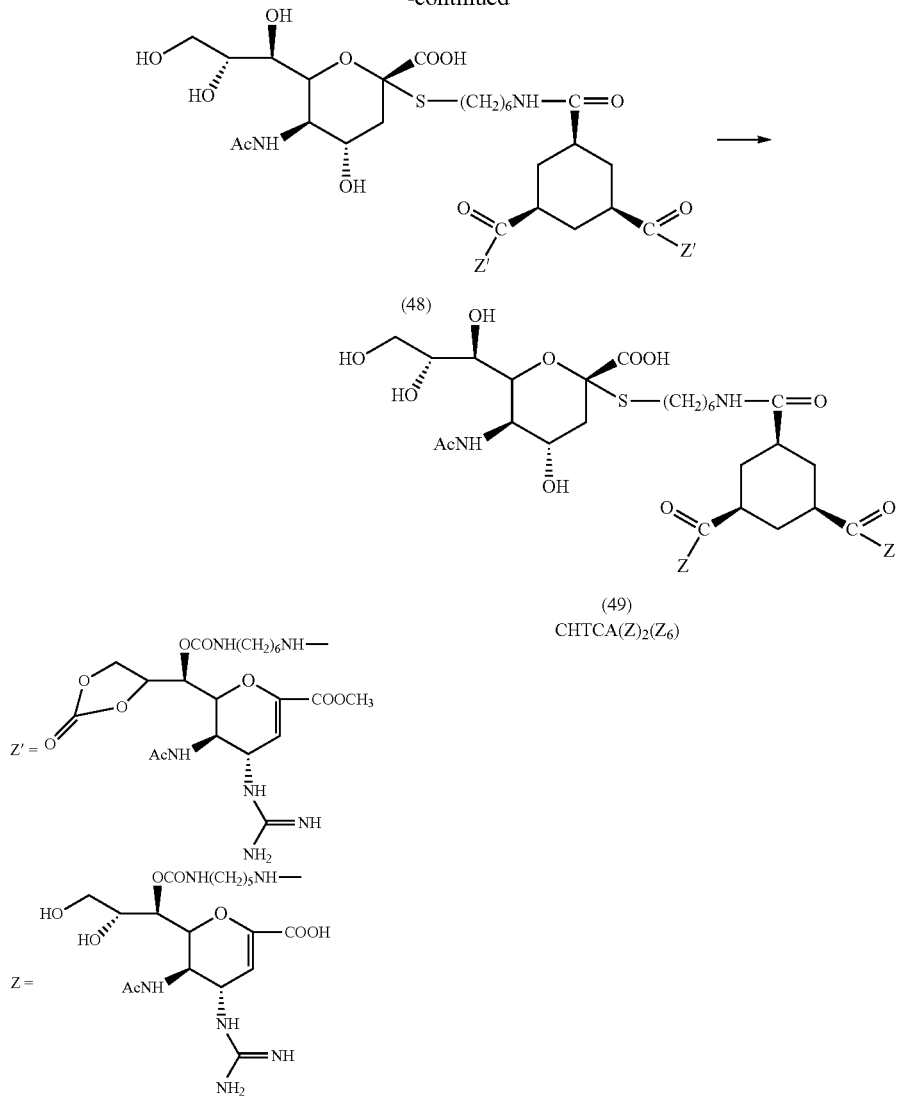

Example 22: Preparation of Anchor-Backbone Compound CHTCA(Z$_{0'}$)$_2$

Synthesis is detailed in Scheme 14 below. The following compound reference numbers relate to Scheme 14.

The preparation of anchor compound (20) Z$_{0'}$ is detailed at Example 15. Anchor-backbone compound (50) CHTCA (Z$_{0'}$)$_2$ was prepared according to the procedure detailed in Example 20. The Anchor-backbone compound (50) CHTCA (Z$_{0'}$)$_2$ was obtained as a white solid. MS ESI +ve, +30 v 1265 indicated the MW of 1264

Scheme 14: Preparation of Anchor-backbone compound CHTCA(Z$_{0'}$)$_2$

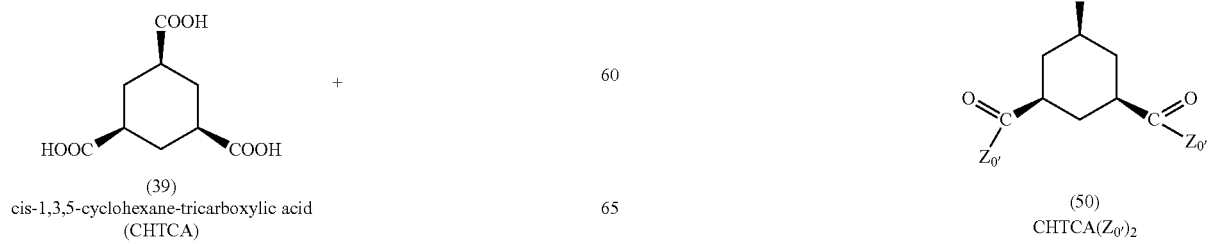

Example 23: Preparation of Acidic/Anionic Group D-Asp(D-Cya)-D-Asp(D-Cya)-D-Asp(D-Cya)-OH Synthesis is detailed in Scheme 15 below. The following compound reference numbers (A) to (1) and synthetic step references relate to Scheme 15.

Boc-D-Cysteine(Acm)methyl ester, [Boc-D-Cys(Acm)-OMe] (1.532 g, 5 mmoles) was dissolved in trifluoroacetic acid (TFA) (10 ml) containing anisole (1 ml), and stirred at room temperature for 30 minutes. The reaction mixture was then evaporated under vacuum to remove TFA to afford an oily substance, which was triturated in ether (100 ml×2) then redissolved in 20% acetonitrile aqueous solution (100 ml), and freeze dried for 72 hrs to give compound TFA.D-Cys(Acm)-OMe, 1.60 g. HPLC/MS indicated the MW of 206.35 (as a free base).

Fmoc-D-Aspartic-α-acid-β-O-t-butyl ester, [Fmoc-D-Asp-Obut], (1.646 g, 4 mmoles) was activated with HBTU (MW 379.25) (1.517 g, 4 mmoles) and DIPEA (MW 129.25) (0.517 g, 4 mmoles) in DMF (20 ml) at room temperature for 10 minutes, then combined with a solution of TFA.D-Cys(Acm)-OMe (1.47 g, 4.2 mmoles) and DIPEA (0.542 g, 4.2 mmoles) in DMF (10 ml). The whole reaction mixture was allowed to stir for 16 hrs at room temperature. The reaction was monitored by HPLC. The mixture was evaporated under vacuum to remove DMF. Then water (5×70 ml) was added to the residue to wash away residual DMF and D-Cys(Acm)OMe to give an off white solid, which was then vacuum dried to yield compound (A), Fmoc-D-Asp[D-Cys(Acm)-OMe]-O-But as a white solid. HPLC/MS indicated MW of 599.7.

Compound (A) (1.2 g, 2 mmoles) was treated with 20% piperidine in acetonitrile (20 ml) for 30 minutes at room temperature, then filtered off. The filtrate was evaporated under vacuum to afford compound (B), D-Asp[D-Cys(Acm)-OMe]-OBut. HPLC/MS indicated MW of 377.4.

Compound (A) (599.7 mg, 1 mmole) was treated with TFA (6 ml) for 1 hr at room temperature. Then it was vacuum evaporated to dryness. The residue was triturated in ether (50 ml×3), then dissolved in 30% acetonitrile aqueous solution (100 ml), and freeze dried to afford compound (C), Fmoc-D-Asp[D-Cys(Acm)-OMe]-OH as a white solid. HPLC/MS indicated MW of 542.7.

Compound (C), Fmoc-D-Asp[D-Cys(Acm)-OMe]-OH (434 mg, 0.8 mmoles) was activated with HBTU (303.4 mg, 0.8 mmole) and DIPEA (103.4 mg, 0.8 mmole) in DMF (8 ml) at room temperature for 10 minutes, then it was added compound (B), D-Asp[D-Cys(Acm)-OMe]-OBut (9332 mg, 0.88 mmoles). The reaction mixture was stirred at room temperature for 16 hrs. The DMF was evaporated under vacuum and the residual DMF was removed by washing the white solid material carefully with water. Then the white solid was dried under vacuum for 24 hrs to afford compound (D), Fmoc-D-Asp[D-Cys(Acm)-OMe]-D-Asp[D-Cys(Acm)-OMe]-OBut, as a white solid. HPLC/MS indicated the MW of 902.19. Compound (D) was treated with TFA (16 ml) at room temperature for 1 hr to remove t-Butyl ester. The TFA was vacuum evaporated to dryness. The residue was washed with water to remove residual TFA and the solid was vacuum dried for 72 hrs to yield Fmoc-D-Asp[D-Cys(Acm)-OMe]-D-Asp[D-Cys(Acm)-OMe]-OH. HPLC/MS indicated the MW of 846.

Fmoc-D-Asp[D-Cys(Acm)-OMe]-D-Asp[D-Cys(Acm)-OMe]-OH (423 mg, 0.5 mmol) was activated with HBTU (189.5 mg, 0.5 mmole) and DIPEA (64.63 mg, 0.5 mmole) in DMF (5 ml) at room temperature for 10 minutes, then was added compound (B), D-Asp[D-Cys(Acm)-OMe]-OBut (317 mg, 0.84 mmole). The whole mixture was stirred at room temperature for 16 hrs. The reaction was checked by HPLC for Completion, and the DMF was removed under vacuum. The white solid obtained was carefully washed with cold water then dried under vacuum for 48 hrs to afford Compound (E), Fmoc-D-Asp[D-Cys(Acm)-OMe]-D-Asp[D-Cys(Acm)-OMe]-D-Asp[D-Cys(Acm)-OMe]-OBut, MW 1206, which was further purified by HPLC.

Analytical HPLC of this material indicated a purity of 70%. The material was dissolved in 50% methanol/water and filtered through 0.2 μm filter for preparative HPLC.

Preparative HPLC

Column: Waters Xterra C18 column 5 μm 19×50 mm in batches of 40 mg; Wavelength: 220/280 nm; Flow rate: 8 ml/min; Solvent A=0.1% Trifluoroacetic acid; Solvent B=100%, Acetonitrile; Gradient: 10-100% B, 100 minutes; Temperature: 30° C.

Compound (E), Fmoc-D-Asp[D-Cys(Acm)-OMe]-D-Asp[D-Cys(Acm)-OMe]-D-Asp[D-Cys(Acm)-OMe]-OBut was then treated with TFA (10 ml) for 1 hr at room temperature and vacuum evaporated to dryness. The residue was dissolved in 40% acetonitrile aqueous solution (100 ml), and freeze dried to afford compound (F), Fmoc-D-Asp[D-Cys(Acm)-OMe]-D-Asp[D-Cys(Acm)-OMe]-D-Asp[D-Cys(Acm)-OMe]-OH, as a white solid. HPLC/MS indicated the MW of 1150.27.

Compound (F), Fmoc-D-Asp[D-Cys(Acm)-OMe]-D-Asp[D-Cys(Acm)-OMe]-D-Asp[D-Cys(Acm)-OMe]-OH (200 mg, 0.1738 mmoles) was treated with 20% piperidine in acetonitrile (10 ml) for 30 minutes with stirred at room temperature and subsequently filtered off. The filtrate was vacuum evaporated. The residue was stirred in 50% water/methanol (20 ml) containing triethylamine (500 μl) at room temperature for 6 hrs, monitored by HPLC to indicate the completion of the reaction. This mixture was vacuum evaporated to dryness to afford compound (G), D-Asp[D-Cys(Acm)-OH]-D-Asp[D-Cys(Acm)-OH]-D-Asp[D-Cys(Acm)-OH]—OH. HPLC/MS indicated the MW of 885.9.

Analytical HPLC indicated 50% purity.

Compound (G) was further purified by preparative HPLC.

Column: Phenomenex Gemini Axia 110A 5 μm 50×21.2 mm C18 HPLC column Wavelength: 210/280 nm; Flow rate: 8 ml/min; Solvent A=0.1% TFA; Solvent B=100% Acetonitrile; Gradient: 0-100% B, 100 s minutes; Temperature: 30° C.

Sample (100 mg) was dissolved in 10% methanol aqueous solution, sonicated, and filtered through a 0.2 μm filter. 20 mg/batches were pumped into the column with a gradient run. Fractions were monitored by analytical RF-HPLC using a Phenomenex Gemini C18 5 μm column. Flow rate 0.7 ml/min; Wavelength 210/280 nm; Gradient 0-50% B 15 minutes; Solvent A=0.1% TFA; Solvent B=100% Acetonitrile.

Fractions with the correct MS great than 90% purity were pooled and freeze dried to afford purified compound (G).

Compound (G), D-Asp [D-Cys(Acm)-OH]-D-Asp-[D-Cys(Acm)-OH]-D-Asp[D-Cys(Acm)-OH]—OH, (21.8 mg, 0.0246 mmoles) was dissolved in TFA (10 ml) containing anisole (200 μl), then was added silver trifluoromethanesulfonate (504 mg, 1.96 mmoles). The reaction mixture was stirred at room temperature for 1 hr. Then it was vacuum evaporated to dryness. The residue was triturated in ether (40 ml×2), the ether washing were decanted. The residue was stirred in 1M acetic acid (20 ml) containing dithiothreitol (403 mg, 2.62 mmoles) at 25° C. for 3 hrs. The suspension was centrifuged in 50 ml falcon tubes for 10 minutes at 4000 rpm. The supernatant was carefully collected, then purified by, HPLC and freeze dried to afford compound (H), D-Asp(D-Cys-SH,—OH)-D-Asp(D-Cys-SH,—OH)-D-Asp(D-Cys-SH,—OH)—OH, HPLC/MS indicated the MW of 672.3.

A mixture of 95% formic acid (7.36 ml), 30% $H_2O_2$ (0.8 ml) and $H_2O$ (0.368 ml) was left at room temperature for 30 minutes, then was stirred at −5° C. ice-bath, to which was added compound (H) (8 mg, 0.0119 mmoles) and stirred for 1 hr, then under vacuum for 10 minutes. The remaining solution was then diluted with water to 200 ml and freeze dried to afford compound (I) 9.5 mg, D-Asp[D-Cya-$SO_3H$,—OH]-D-Asp[D-Cya-$S_3OH$,—OH]-D-Asp[D-Cya-$SO_3H$,—OH]—OH as a white solid, HPLC/MS indicated the MW of 816.78.

This compound was purified by desalting under the following conditions.

Column: Phenomenex Gemini Axia 110A 5 μm 50×21.2 mm C18 HPLC column; Wavelength: 210/280 nm; Flow rate: 8 ml/min; Solvent A=0.1% TFA; Solvent B=100% Acetonitrile; Gradient: 0-100% B, 100 minutes Temperature: 30° C. The compound (I) elutes near the void.

This material was then freeze dried to produce a white powder as pure compound (I). Compound (I) was neutralized with triethylamine (TEA) to form a TEA salt (51) as follows:

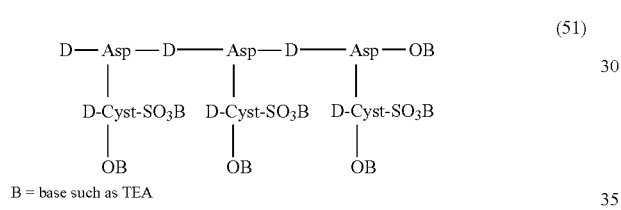

(51)

B = base such as TEA

*HBTU: O-1H-Benzotriazol-1-yl)-N,N,N',N'-tetramethyluranium hexafluorophosphate MW379.24
TFA: Trifluoroacetic acid MW 114.02
DIPEA: Diisopropylethylamine MW 129.25
TEA; Triethylamine MW 101.19
Acm: S-Acetamidomethyl as thio protecting group
OBut: t-Butyl ester Scheme 15: Preparation of Acidic/Anionic Group D-Asp(D-Cyst)-D-Asp(D-Cyst)-D-Asp(D-Cyst)-OH

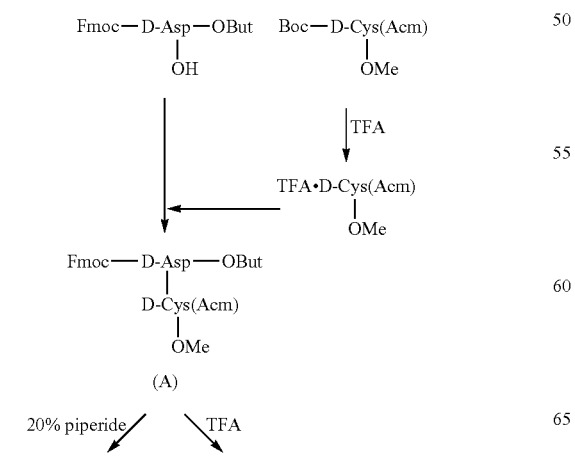

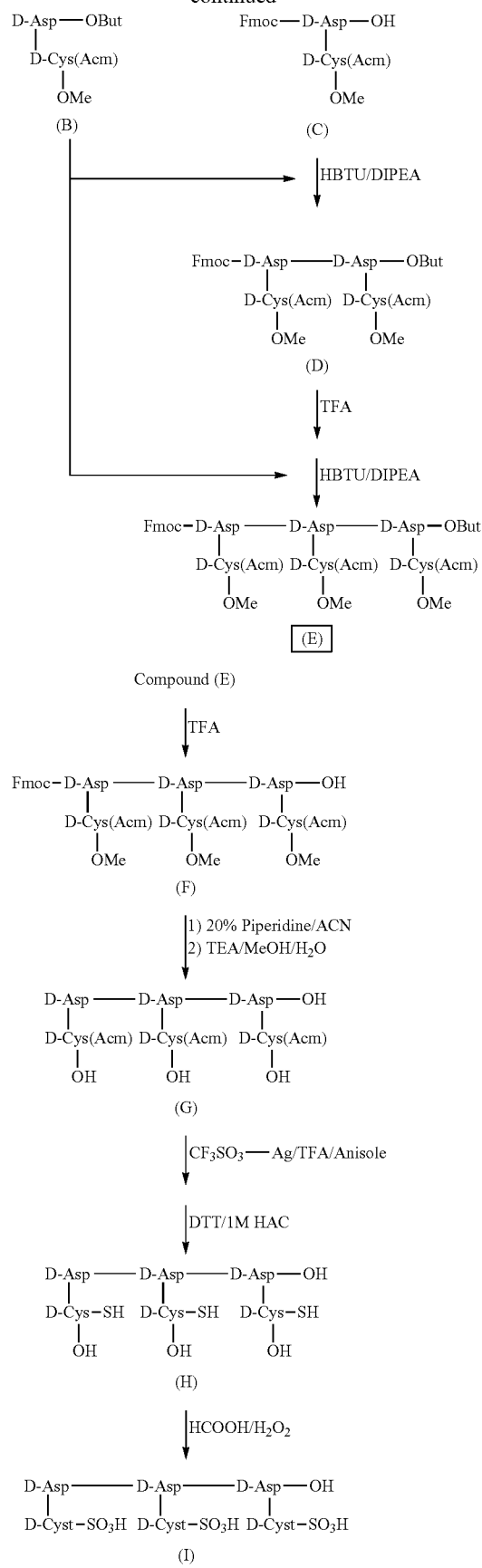

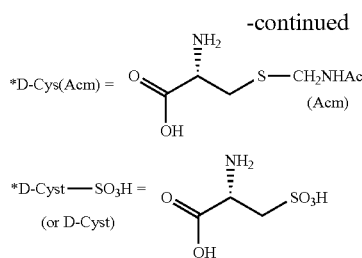

Example 24: Preparation of Compound MD348, CHTCA($Z_0$)$_2$-[D-Asp(D-Cyst)-D-Asp(D-Cyst)-D-Asp(D-Cyst)]-OH Synthesis is detailed in Scheme 16 below. The following compound reference numbers relate to Scheme 16.

Compound (50), CHTCA($Z_0'$)$_2$ from Example 22 (10.744 mg, 8.5 μmoles) was stirred with HATU (3.23 mg, 8.5 μmoles) and DIPEA (1.496 μl, 8.56 μmoles) in DMF (5 ml) at room temperature for 10 minutes, then it was combined with compound (51), D-Asp(D-Cya-SO$_3$B,—OB)-D-Asp-(D-Cya-SO$_3$B,—OB)-D-Asp(D-Cya-SO$_3$B,—OB)—OB, from Example 23 (13.2 mg, 8.67 μmoles) in DMF (5 ml). The whole mixture was stirred at room temperature for 16 hrs. The resulting mixture was monitored by analytical HPLC/MS at retention time Peak 1, 12.903 min. 44% MS ESI +ve, +20 v 1032.3 2+ion, ESI –ve, –40 v 1030.7 2+ion, indicated the MW of 2062 as compound (52) without base, that is, CHTCA($Z_0$)$_2$[D-Asp(D-Cya-SO$_3$H,—OH)-D-Asp(D-Cya-SO$_3$H,—OH)-D-Asp-(D-Cyst-SO$_3$H,—OH)]—OH.

Analytical HPLC:
  Column: Phenomenex Kinetex EVO 5 μm C18 100A 150×4.6 mm; Wavelength: 210/280 nm; Flow rate: 0.7 ml/min; Solvent A=0.1% TFA; Solvent B=100% Acetonitrile; Gradient: 0-50% B, 15 minutes, linear; Temperature: 30° C.

The resulting mixture was acidified with citric acid, diluted to 20 ml with water, and filtered through 0.2 μm filter, then subjected to preparative HPLC for separation and purification.

Preparative HPLC
  Column: Phenomenex Gemini AXIA 5 μm C18 110A 50×21.2 mm; Wavelength: 210/280 nm; Flow rate: 8 ml/min; Solvent A=0.1 TFA; Solvent B=100% Acetonitrile; Gradient: 0-100% B, 100 minutes, linear; Temperature: 30° C.

Major peak with retention time of 31.087 min was the product (52). Fractions containing product were collected and repurified by further HPLC as follows.

Column: Phenomenex Kinetex×B 5 μm C18 100A 50×21.2 mm; Wavelength: 210/280 nm; Flow rate: 8 ml/min; Solvent A=0.1 TFA; Solvent B=100% Acetonitrile; Gradient: 5%-100% B, 80 min, linear; Temperature 30° C.

The purified compound (52) at retention time of 19.597 min was completely separated from the starting material at retention time of 21.714 min.

Compound (52) (3.5 mg, 1.697 μmoles) was dissolved in 50% methanol/water (5 ml) containing triethylamine (TEA) (18 μl, 129 μmoles). It was stirred at room temperature for 3 hrs. HPLC indicated the incompletion of the reaction, therefore, an additional 11 μl of TEA was added. The mixture was stirred for another 60 minutes by then HPLC indicated the completion of the reaction. The reaction solution was then neutralized to pH 6 with 1M acetic acid. The solution was then diluted to 20 ml with water. The mixture was subjected to HPLC.

Analytical HPLC
  Column: Phenomenex Kinetex Evo 5 μm C18 100A 150×3 mm; Wavelength: 210/280 nm Flow rate: 0.7 ml/min; Solvent A=20 mM NaHPO$_4$ pH 7.0 buffer; Solvent B=10 mM NaHPO$_4$ pH 7.0 buffer+50% Acetonitrile; Gradient: 0-100% B, 30 minutes, linear; Temperature: 30° C.

Preparative HPLC
  Column: Phenomenex Kinetex XB 5 μm C18 100A 50×21.2 mm; Wavelength: 210/280 nm Flow rate: 8 ml/min; Solvent A=0.1% TFA Solvent B=100% Acetonitrile Gradient: 0-100% B, 80 min, linear; Temperature: 30° C.

The product (53) was eluted at a retention time of 16.431 min.

Pure fractions were combined and freeze dried, then using HCl exchange to remove the residual TFA. Freeze drying afforded the product (53) CHTCA($Z_0$)$_2$[D-Asp(D-Cya)-D-Asp(D-Cya)-D-Asp(D-Cya]-OH at purity >99% as a white solid. MS ESI cone –20 v, 990.5 2+ion indicated the MW of 1982.

Scheme 16: Preparation of Compound MD348, CHTA($Z_0$)$_2$-[D-Asp(D-Cyst)-D-Asp(D-Cyst)-D-Asp(D-Cyst)]-OH

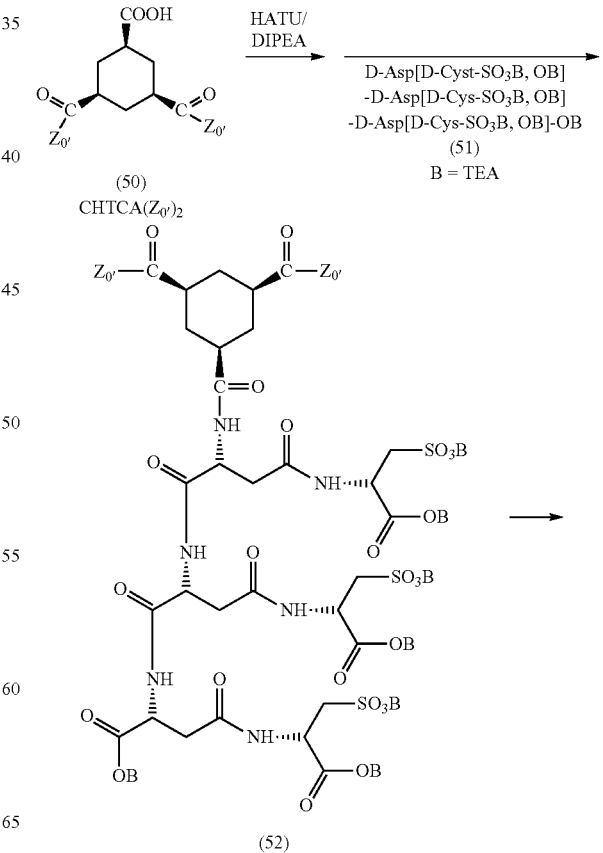

(53)
MD348 CHTCA($Z_0$)$_2$-[D-Asp(D-Cyst)-D-Asp(D-Cyst)-D-Asp(D-Cyst)]-OH
MW 1982

REFERENCES

1) WHO: influenza (seasonal), 2009, accessed at: http://www.who.intimediacentre/factsheets/fs211/en.
2) Metersky M L, Masterton R G, Lode H, File T M Jr, Babinchak T: Epidemiology, microbiology, and treatment considerations for bacterial pneumonia complicating influenza. *Int J infect Dis.,* 2012 16:e 321-331.
3) Hale B G, Albrecht R A, Garcia-Sastre A: Innate immune evasion strategies of influenza viruses. *Future Microbiol,* 2010, 5:23-41.
4) Palese P, Shaw M L; orthomyxoviridae: the viruses and their replication, In *Fields Virology,* 5 edition. Edited by: Knipe D M, Howley P M, Philadelphia, Pa.: Lippincott Williams 2007:1647-'689.
5) Salomon R. et al.: The influenza virus enigma. *Cell,* 136 (3), 402-410 (2009).
6) Gao R et al.: Human infection with a novel avian-origin influenza A (H7N9) virus. N. Engl. J. Med. 368 (2Q): 1888-1897 (2013).
7) Imal M. et al. Experimental adaptation of an influenza H5 HA confers respiratory droplet transmission to reassortant H5 HA/H1N1 virus in ferrets. *Nature.* 486 (7403): 420-428 (2012).
8) Herfst S. et al.: Airborne transmission of influenza A/H5N1 virus between ferrets. *Science.* 336 (6088):1534-1541 (2012).
9) Russell C A. et al.: The potential for respiratory droplet-transmissible A/H5N1 influenza virus to evolve in a mammalian host. *Science.* 336 (6088): 1541-1547 (2012).
10) Hu Y, et al.: Association between adverse clinical outcome in human diseases caused by novel influenza A H7N9 virus and sustained viral shedding and emergences of antiviral resistance. *Lancet.* 381 (9885): 2273-2279 (2013).
11) Bat M, et al.: Emergence of Oseltainivir-resistant pandemic H1N1 virus during prophylaxis. *N. Engl. J Med.,* 361 (23): 2296-2297 (2009).
12) Hayden F: Developing new antiviral agents for influenza treatment: what does the future hold? *Clinical Infectious Diseases.* 48:S3-13 (2009).
13) Das K, et al.: Structures of influenza A proteins and insights into antiviral drug targets. *Nature Structural & Molecular Biology. Vol.* 17, No. 5, 530-538 (2010).
14) Hayden F.: Newer influenza antivirals, biotherapeutics and combinations. Influenza and Other *Respiratory Viruses* 7 (Suppl. 1), 63-75 (2012).
15) Wathen M W, et al.: Antivirals in seasonal and pandemic influenza-future perspectives. *Influenza and Other Respiratory Virus,* 7 (Suppl. 1), 76-80 (2012).
16) Novel antiviral therapies for influenza and other respiratory viruses: Bench to Bedside. The 4th ISIRV-AVG Conference, 2-4 Jun. 2015, University of Texas at Austin USA.
17) Chen, W. et al. A novel influenza A virus mitochondrial protein that induces cell death. *Nat. Med.* 7, 1306-1312 (2001).
18) Rebel, J. J. & Wiley, D. C. Receptor binding and membrane fusion in virus entry; the influenza hemagglutinin. *Annu. Rev. Biochem.* 69, 531-569 (2000).
19) Wu. W. W. & Pante, N. The directionality of the nuclear transport of the influenza A genome is driven by selective exposure of nuclear localization sequences on nucleoprotein. *Virol. J.,* 6, 68 (2009).
20) Ulmanen I., Broni. B. A. & Krug, R. M. The role of two of the influenza virus core P proteins in recognizing cap 1 structures (m$^7$GpppNm) on RNAs and in initiating viral RNA transcription. *Proc. Natl. Acad. Sci. USA,* 78, 7355-7359 (1981).
21) Plotch, S. J., Bouloy. M., Uhranen, I. & Krug, R. M. A unique cap(m7GpppXm)-dependent influenza virion endonuclease cleaves capped RNAs to generate the primers that initiate viral RNA transcription. *Cell,* 23, 847-858 (1981).
22) Hagen, M., Chung, T. D. Y., Butcher, A. & Krystal, M. Recombinant influenza virus polymerase: requirement of both 5' and 3' viral ends for endonuclease activity. *J. Virol.,* 68, 1509-1515 (1994).
23) Shimizu. K., Iguchi, A., Gomyou. R. & Ono, Y. Influenza virus inhibits cleavage of the HSP70 pre-mRNAs at the polyadenylation site. *Virology,* 254, 213-219 (1999).
24) Nemeroff, M. E., Barabino, S. M., Li, Y., Keller, W. & Krug, R. M. Influenza virus NS1 protein interacts with the cellular 30 kDa subunit of CPSF and inhibits 3' end formation of cellular premRNAs. Mol. Cell 1, 991-1000 (1998).
25) Newcomb, L. L. et al. Interaction of the influenza a virus nucleocapsid protein with the viral RNA polymerase potentiates unprimed viral RNA replication. *J. Virol.,* 83, 29-36 (2009).
26) Neumann, G., Hughes, M. T. & Kawaoka, Y. Influenza A virus NS2 protein mediates vRNP nuclear export through NES-independent interaction with hCRM1. *EMBO J.,* 19, 6751-6758 (2000).
27) Nayak, D. P., Hui, E. K. & Barman, S. Assembly and budding of influenza virus. *Virus Res.* 106, 147-165 (2004).
28) Rennie P., Bowell P. et al.: Low pH intranasal sprays inactivate influenza viruses in vitro and protect ferrets against influenza infection. *Respiratory Research.* 8, 37 (2007).
29) Anderson I. Proctor D F: Measurement of nasal mucociliary clearance. *Eur. J. Respir. Dis.,* 64, 37-40 (1983).

30) Lande E. A. et al.: A comparative study of the effect of Citric acid, Capsaicin and, Resiniferatoxin on the cough challenge in Guinea-pig and man. *Pulmonary Pharmacology*, 6, 171-175 (1993).
31) Tanaka, M. et al.: Mechanisms of Capsaicin- and Citric-acid-induced cough reflexes in GuineaPig. *J. Pharmacol. Sci.*, 99, 77-82 (2005).
32) Erik De Clercq, Toward improved anti-HIV chemotherapy, therapeutic strategies for intervention with HIV infections. *Med. Chem.*, vol. 38, No. 14, P. 2491 (1995).
33) Abed Y et al.: Generation and Characterization of recombinant influenza A (H1N1) virus harboring amantadine resistance mutation. *Antimicrob. Agents Chemother.* 49: 556-559 (2005).
34) Bright R. et al.: Adamantane resistance around influenza A viruses isolated early during the 2005-2006 influenza season in the United States. *JAMA*, 8: 891-894 (2006).
35) Bright R. et al.: Incidence of adamantane resistance among influenza A (H3N2) viruses isolated worldwide from 1994 to 2005: a cause for concern. *Lancet*, 9492: 1175-1181 (2005).
36) Nelson M. et al.: The origin and global emergence of adamantine resistant A (H3N2) influenza virus. *Virology*, 388: 270-278 (2009).
37) Von Itzstein et al.: Rational Design of Potent Sialidase-based Inhibitors of Influenza Virus Replication. *Nature*, 363, 418-423 (1993).
38) Klumpp, K.: Recent Advances in the Discovery and Development of Anti-influenza Drugs. *Expert Opin. Ther. Pat.*, 14, 1153-1168 (2004).
39) Wang, G.: Recent Advances in the Discovery and Development of Anti-influenza Drugs. *Expert Opin. Ther. Pat.*, 12, 845-861 (2002).
40) Abdel-Magid, A. F. et al.: Synthesis of Influenza Neuraminidase Inhibitors. *Curr. Opin. Drug Discuss. Dev.*, 4, 776-791 (2001).
41) Wang, G. T. et al.: Design, Synthesis, and Structure Analysis of Influenza Neuraminidase Inhibitors Containing Pyrrolidine Cores. *J. Med. Chem.*, 44, 1192-1201 (2001)
42) Babu, Y. S. et al.: Discovery of a Novel, Highly Potent, Orally Active, and Selective Influenza Neuraminidase Inhibitor through Structure-based Drug Design *J. Med. Chem.*, 43, 3482-3486 (2000).
43) Chand, P. et al.: Syntheses and Neuraminidase Inhibitory Activity of Multisubstituted Cyclopentane Amide Derivatives. *J. Med. Chem.*, 47, 1919-1929 (2004).
44) Honda. T. et al.: Synthesis and Anti-influenza Evaluation of Polyvalent Sialidase Inhibitors bearing 4-Guandino-Neu5Ac2en derivatives. *Bioorg. Med Chem. Lett.* 12, 1929-1932 (2002).
45) Honda, T. et al.: Synthesis and Anti-influenza Virus Activity of 7-O-Alkylated derivatives Related to Zanamivir. *Bioorg. Med. Chem. Lett.* 12, 1925-1928 (2002).
46) Del Mar C. et al.: Neuraminidase inhibitors for influenza complications. Lancet 384, 1260 (2014).
47) Jefferson T. et al.: Neuraminidase inhibitors for preventing and treating influenza in healthy adults and children. *Cochrane Database Syst. Rev.*, 4:CD008965 (2014).
48) Nguyen-Van-Tam J S. et al.: Antivirals for influenza where now for clinical practice and pandemic preparedness? *Lancet*. 384: 386-387 (2014).
49) Reece, P. A. et al.: PCT Int Appl. WO98/21243 (1998). CA1998, 12928172.
50) Watson, K. G.; et al.: Highly potent and long-acting trimeric and tetrameric inhibitors of influenza virus neuraminidase. *Bioorg. Med. Chem., Lett.*, 14, 1589 (2004).
51) Demaine, D. A. et al.: Dimeric compounds and their use as anti-viral agents. W003/040138. Chem. Abstr., 138: 354175 (2003).
52) Macdonald, S. J. F. et al.: Potent and long-acting dimeric inhibitors of influenza virus neuraminidase are effective at a one-weekly dosing regimen. *Antimicrob. Agents and Chemoth.*, 48, 4542 (2004).
53) Macdonald, S. J. F.; et al.: Dimer zanamivir conjugates with various linking group are potent, long-lasting inhibitors of influenza neuraminidase including H5N1 Avian influenza. *J. Med. Chem.*, 48, 2964 (2005).
54) Fraser B. H. et al.: Synthesis of 1,4-triazole linked zanamivir dimers as highly potent inhibitors of influenza A and B. *Med Chem. Commun.*, 4, 383 (2013).
55) Watanabe W. et al. *J. of Virological Methods*, 48, 257 (1994).

We claim:

1. A compound of Formula (I):

Formula (I)

or a pharmaceutically acceptable salt, solvate, ester or stereoisomer thereof, wherein:

A at each occurrence is an anchoring group selected from the group consisting of zanamivir, laninamivir, oseltamivir, peramivir, and 2,3-difluoro sialic acids or an antibody binding domain which specifically binds neuraminidase;

B is a multivalent backbone group selected from the group consisting of optionally substituted propane-1,2,3-tricarboxylate, prop-1-ene-1,2,3-tricarboxylate, cyclopropane-1,2,3-tricarboxylate, cyclohexane-1,3,5-tricarboxylate, benzene-1,3,5-tricarboxylate, methane tetracarboxylate, 1,2,3,4-butane tetracarboxylate, ethylene-1,1,2,2-tetracarboxylate, cyclohexane-1,2,4,5-tetracarboxylate, and benzene-1,2,4,5-tetracarboxylate;

C at each occurrence is an anionic group of Formula VIII:

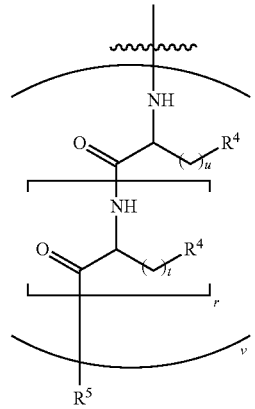

(Formula VIII)

wherein $R^4$ at each occurrence is independently selected from the group consisting of —COOH, —$SO_3H$, —$NHCH_2SO_3H$, —CONH-Cya, -CONN-Asp, —CONH-Asp(-$NHCH_2SO_3H)_w$, and —CONH-Asp(-$NHCH_2PO_3H)_w$, wherein w is an integer 1 or 2;

$R^5$ is selected from the group consisting of —OH and —$NHCH_2SO_3H$;

u is an integer from 0 to 3;

t is an integer from 0 to 3;

r is an integer from 0 to 6; and v is an integer from 1 to 12;

$L^1$ and $L^2$ at each occurrence are divalent linkers;

n is 2 or 3; and p is 1 or 2.

2. The compound of claim 1, wherein the anchoring group is selected from the group consisting of an antibody (Ab) or an antigen binding fragment of an antibody, a single chain antibody fragment (scFV) and a single domain antibody (dAb).

3. The compound of claim 1 or claim 2, wherein $L^1$ and $L^2$ at each occurrence are independently selected from the group consisting of a bond, optionally substituted $C_1$-$C_{12}$ alkylene, —C(O)—NR—, —O—C(O)O—NR—, —C=N—O—, —C=N—NR—, —SO$_2$—NR—, disulfide, —C(O)—NR—(CH$_2$)$_x$—NR—, —(CH$_2$)$_x$—NR—, —(CH$_2$)$_x$—(O—(CH$_2$)$_y$—)$_z$—, optionally substituted-C=N—O—, optionally substituted —C=N—NR-alkylene, optionally substituted alkylene sulfonamide, an optionally substituted alkylene disulfide, wherein R is independently H or $C_1$-$C_6$ alkyl and wherein x, y and z are each integers independently selected from 0, 1, 2, 3 and 4.

4. The compound of any one of claims 1, 2, or 3, wherein B is selected from the group consisting of optionally substituted propane-1,2,3-tricarboxylate, optionally substituted cyclohexane-1,3,5-tricarboxylate, and optionally substituted benzene-1,2,4,5-tetracarboxylate.

5. The compound of claim 1 selected from the group consisting of:

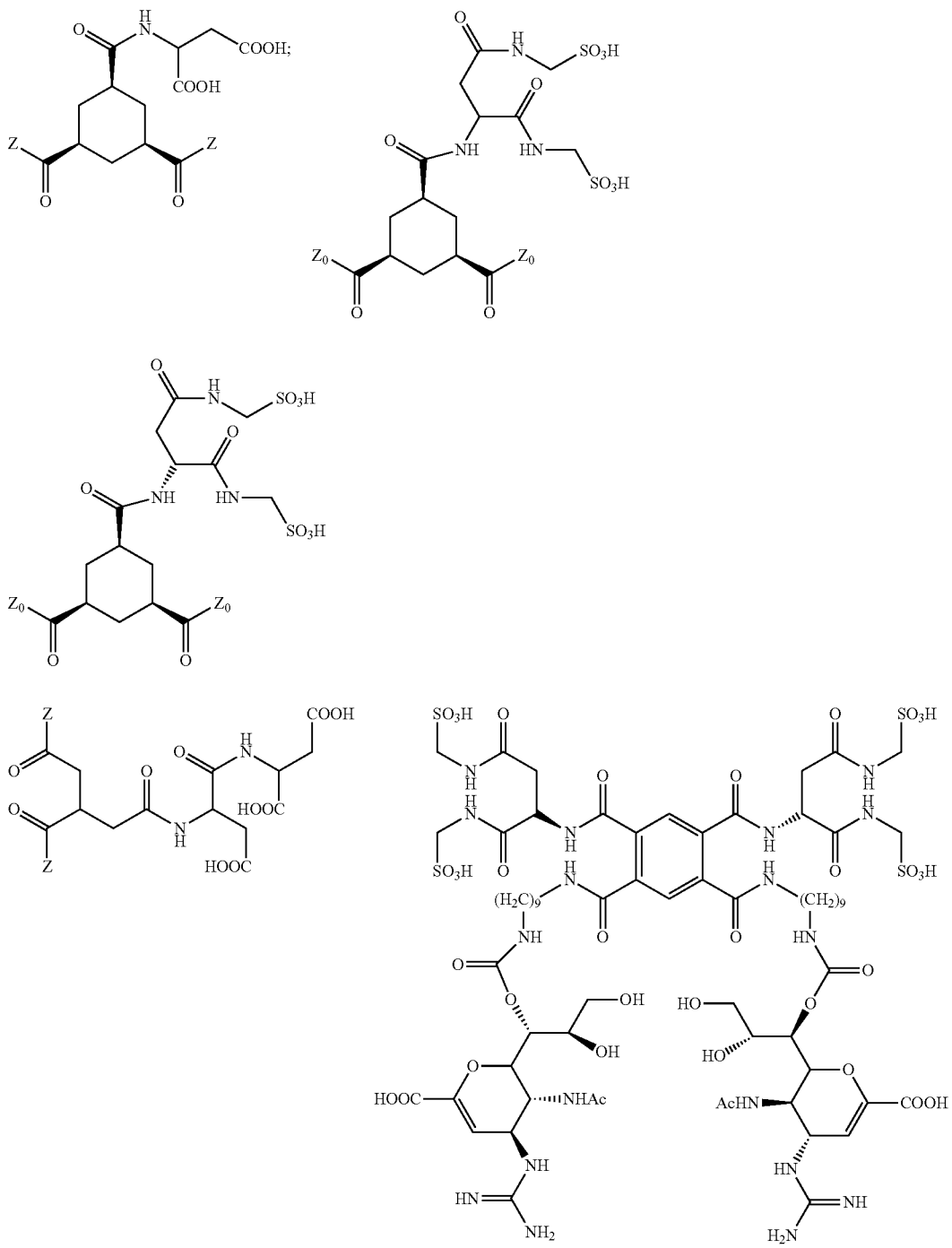

123
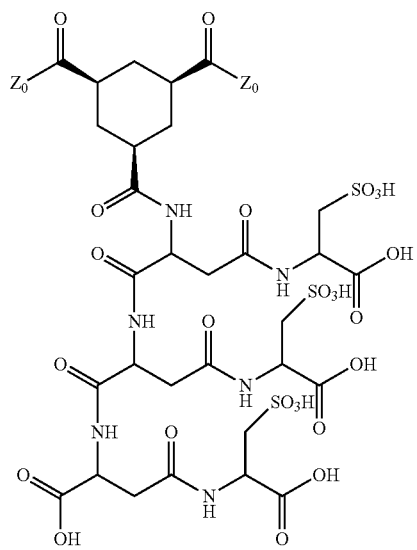
-continued
124
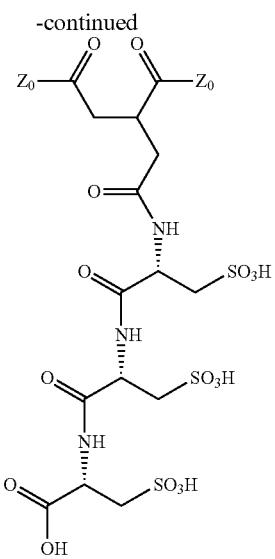
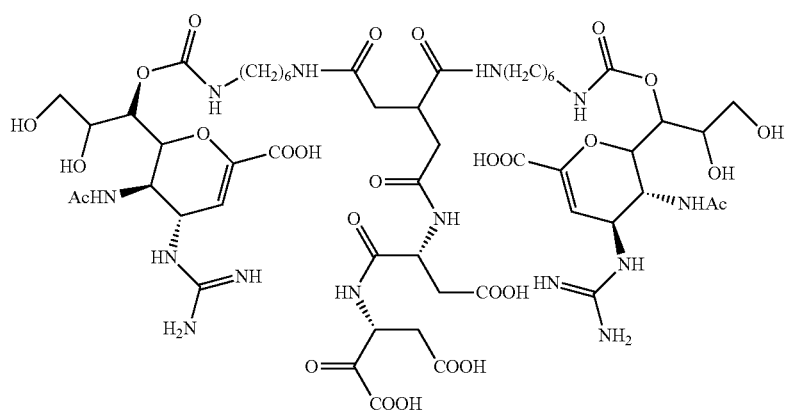
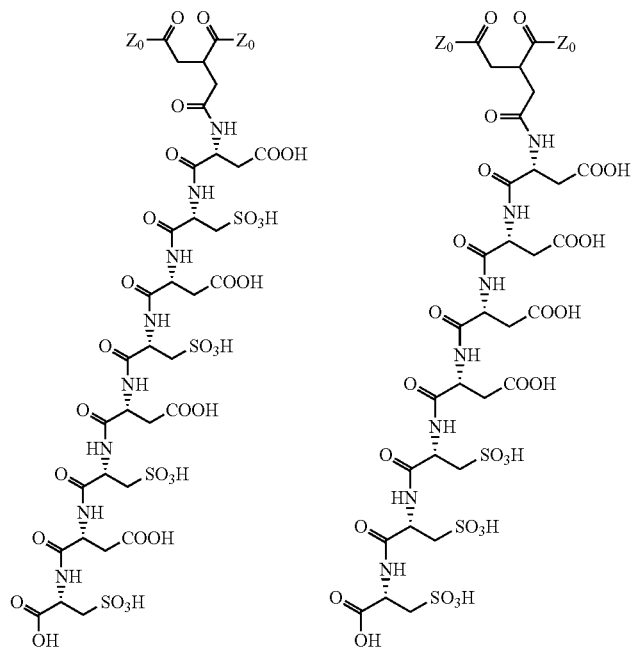

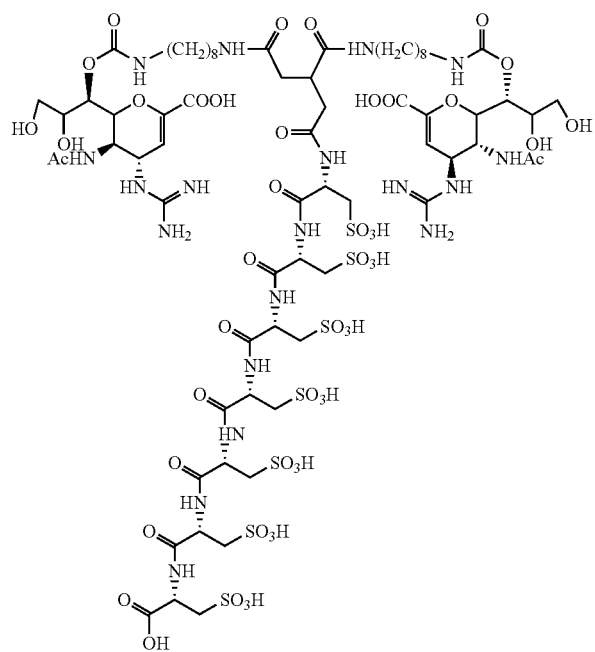
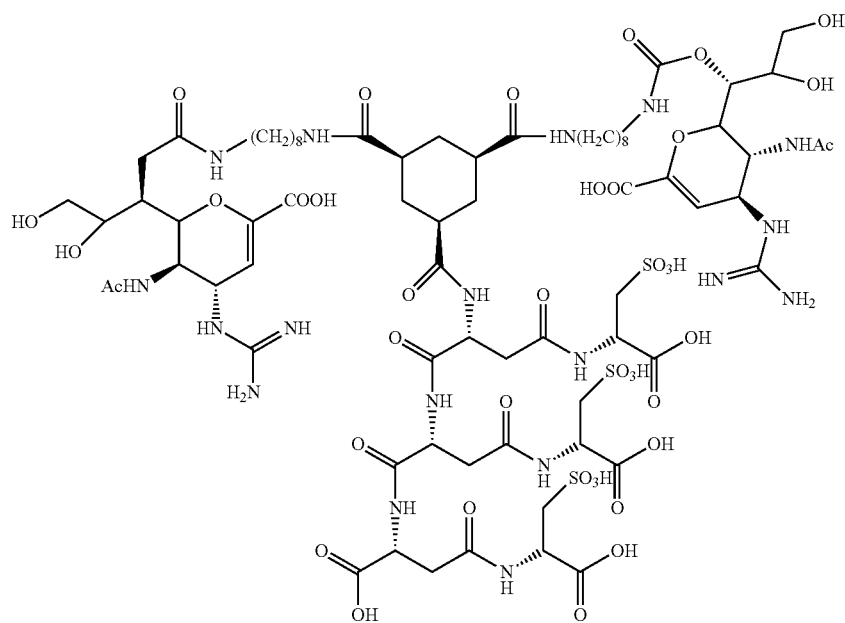

127
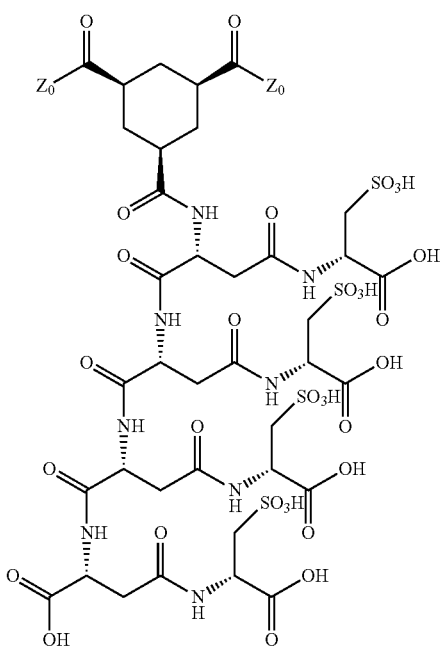
128
-continued
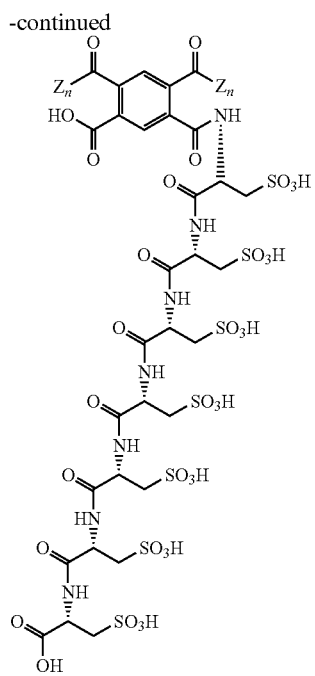
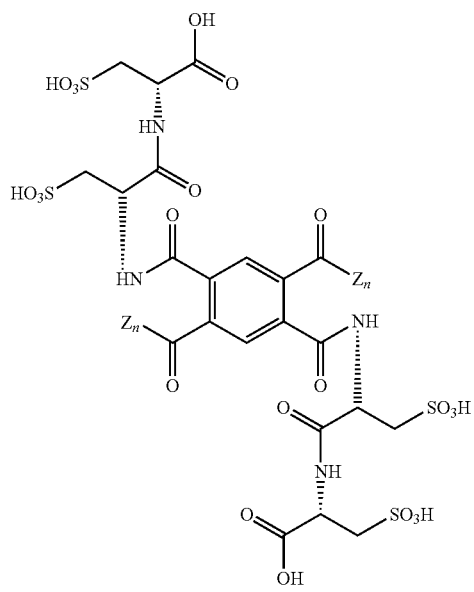
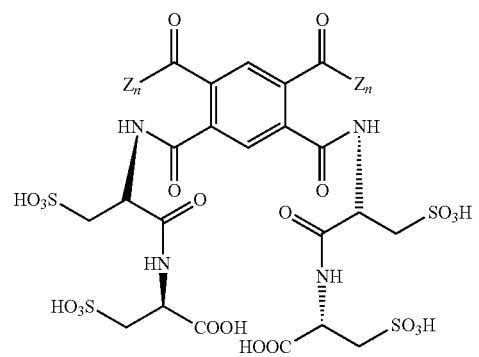

129
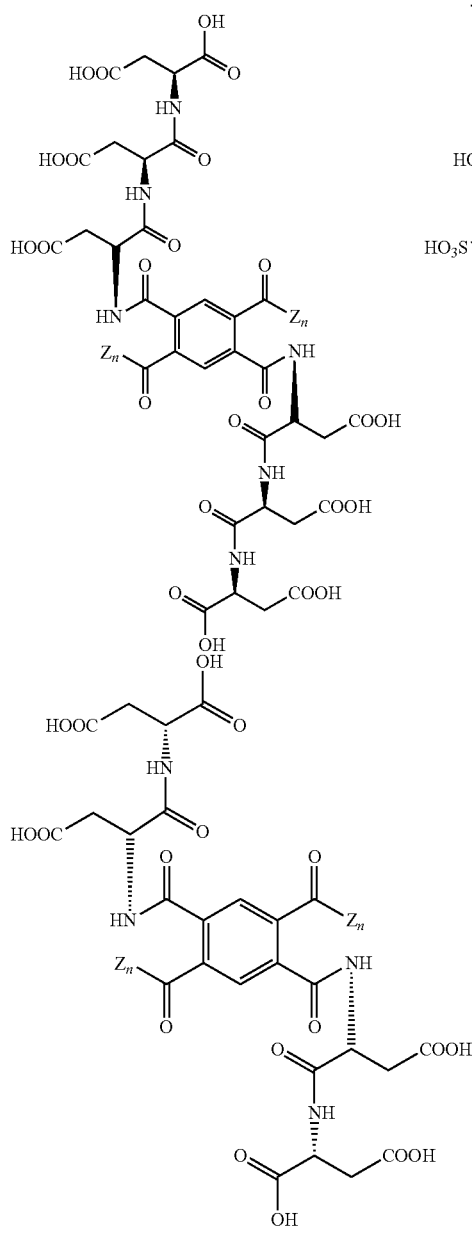
wherein
$Z_0$ is;
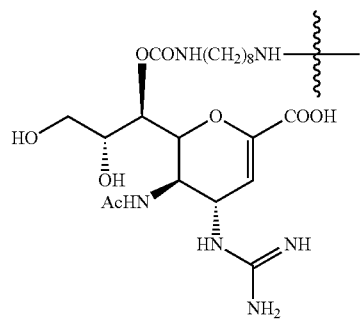
-continued
130
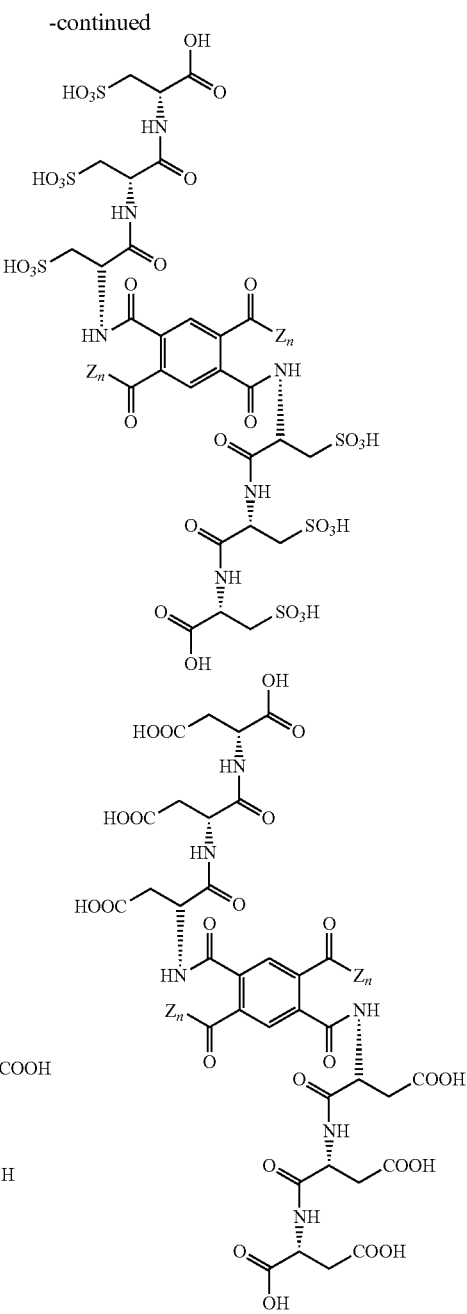
Z is
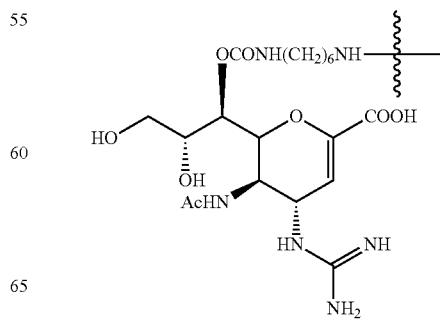

and $Z_n$ is

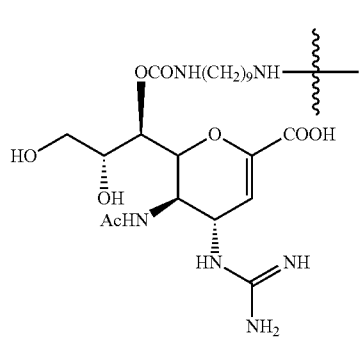

or a pharmaceutically acceptable salt, solvate, ester or stereoisomer thereof.

6. The compound of claim 1, wherein A is zanamivir.

7. The compound of claim 1, wherein B is benzene-1,2,4,5-tetracarboxylate.

8. The compound of claim 1, wherein $R^4$ at each occurrence is COOH and $R^5$ is —OH.

9. The compound of claim 1, wherein $L^2$ at each occurrence, is a bond.

10. The compound of claim 1, wherein [A-$L^1$] at each occurrence, is represented by a group of formula $Z_x$ having the structure:

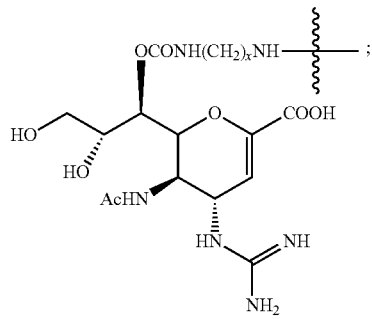

wherein x is an integer from 0-12.

11. The compound of claim 10, wherein $Z_x$ is a group of formula $Z_n$:

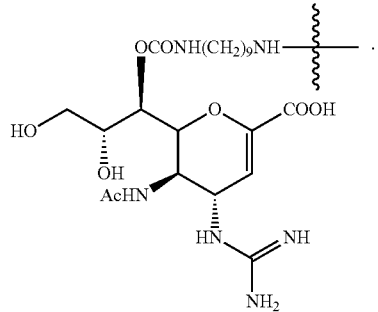

12. The compound of claim 1 of structure:

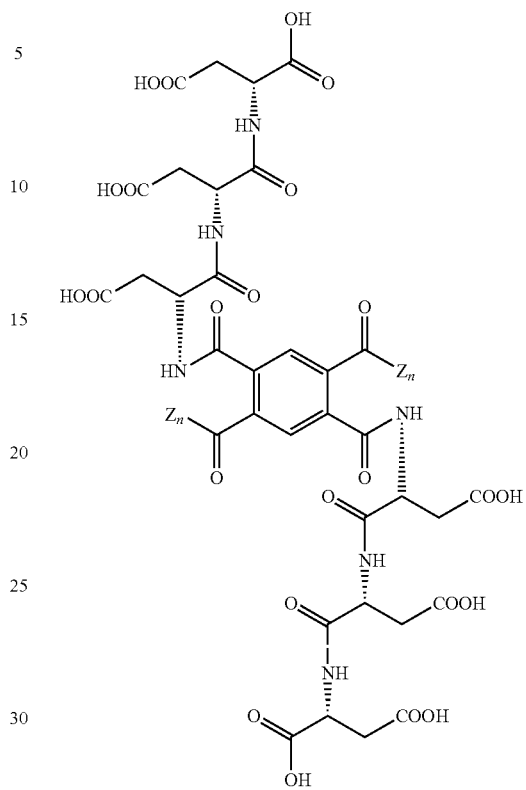

wherein
$Z_n$ is

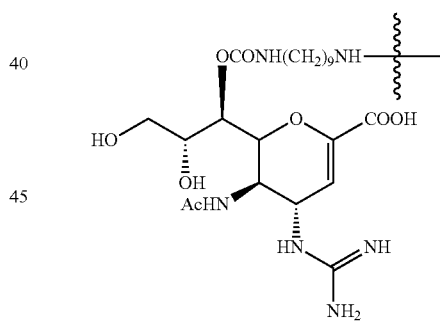

or a pharmaceutically acceptable salt, solvate, ester or stereoisomer thereof.

13. The compound of claim 12, wherein the compound is an alkyl ester.

14. A pharmaceutical composition comprising a compound of claim 1.

15. The pharmaceutical composition of claim 14, wherein the compound is a compound of claim 5.

16. A method of treating or preventing influenza viral infection, comprising administering to a person in need thereof, a therapeutically effective amount of a compound of claim 1.

17. The method of claim 16 wherein the influenza viral infection is influenza A, influenza B, avian flu, or a drug resistant strain of influenza.

18. The method of claim 16 wherein the infection is a respiratory tract infection or a systemic infection.

19. The method of claim 16, wherein the compound is selected from
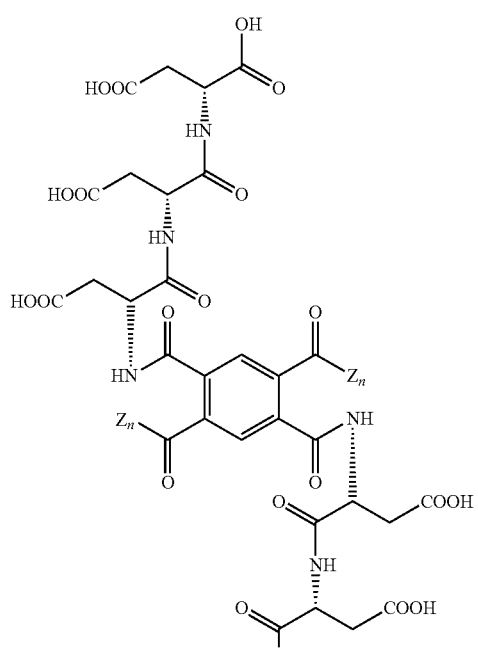
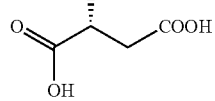
wherein
$Z_n$ is
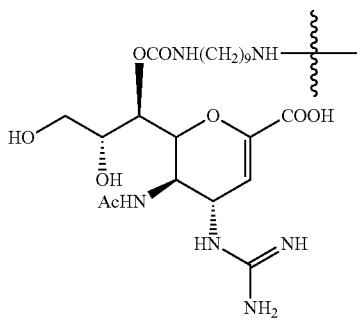
or a pharmaceutically acceptable salt, solvate, ester or stereoisomer thereof.
* * * * *